(12) United States Patent
Cheng et al.

(10) Patent No.: US 7,030,139 B2
(45) Date of Patent: Apr. 18, 2006

(54) COMPOUNDS

(75) Inventors: Yun-Xing Cheng, Montreal (CA); Miroslaw Tomaszewski, Montreal (CA); Christopher Walpole, Montreal (CA); Hua Yang, Montreal (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/474,549

(22) PCT Filed: Apr. 18, 2002

(86) PCT No.: PCT/SE02/00769

§ 371 (c)(1),
(2), (4) Date: Oct. 9, 2003

(87) PCT Pub. No.: WO02/085866

PCT Pub. Date: Oct. 31, 2002

(65) Prior Publication Data

US 2004/0116465 A1 Jun. 17, 2004

(30) Foreign Application Priority Data

Apr. 20, 2001 (SE) .................... 0101387

(51) Int. Cl.
*A61K 31/445* (2006.01)

(52) U.S. Cl. ............... 514/322; 514/338; 514/397; 514/393; 514/394; 514/385; 514/233.8; 514/233.5; 514/311; 548/304.4; 548/304.7; 548/306.1; 548/305.1; 548/307.1; 548/309.7; 548/310.1; 548/204; 546/152; 546/176; 546/199; 546/273.4; 546/273.7

(58) Field of Classification Search ............ 548/304.4, 548/304.7, 306.4, 306.1, 305.1, 307.1, 309.7, 548/310.1, 204; 546/199, 273.4, 273.7, 176, 546/152; 544/139, 111; 514/394, 395, 365, 514/338, 322, 314, 234.5, 397, 393, 385, 514/311, 233.8, 233.5

See application file for complete search history.

(56) References Cited

U.S. PATENT DOCUMENTS 2,945,044 A * 7/1960 Rossi et al. .............. 548/309.7

FOREIGN PATENT DOCUMENTS

| FR | 1481049 A | 4/1967 |
| FR | 1481049 | 5/1967 |
| WO | WO 2004035548 A1 * | 4/2004 |

OTHER PUBLICATIONS

Burke et al. J. Med. Chem. 1984, 27:1570-1574.*
Smith et al. Journal of Combinatorial Chemistry. 1999, 1(5):368-370.*
Lecolier, S. et al. "New benzimidazoles with morphine activity", Chim. Ther., 1967, pp. 16-24, vol. 2, No. 1.
Seki, Teruya et al., "2-Benzimidazolethiol derivatives . . . -5-substituted, benzimidazole", Chem. Abstracts, vol. 71 No. 13, p. 445, The Abstract, No. 61291h, Yakugaku Zasshi 1969, 89 (5), 617-626.
Paglietti, G. et al., "Dialkylaminoalkylbenzimidazoles of pharmacological interest", p. 84, Chemical Abstracts, vol. 78, No. 1, Jan. 8, 1973 The Abstract No. 87u, Studi Sassar., Sez. 1971, 2, 192-203.
Paglietti, G. et al., "Dialkylaminoalkylbenzimidazoles of pharmacological interest. III.", p. 479, Chemical Abstracts, vol. 77, No. 7, Aug 14, 1972, The Abstract No. 48338h, Farmaco, Ed. Sci. 1972, 27 (4), 333-342.
Lecolier, Serge et al., "New benzimidazoles with morphine activity", pp. 16-24, Chim. Ther., vol. 2, No. 1, 1967.

* cited by examiner

*Primary Examiner*—Amelia A. Owens
(74) *Attorney, Agent, or Firm*—Jianzhong Shen

(57) ABSTRACT

Compounds of general formula (I), are disclosed and claimed in the present application, as well as salts and pharmaceutical compositions comprising the novel compounds and their use in therapy, in particular in the management of pain (I)

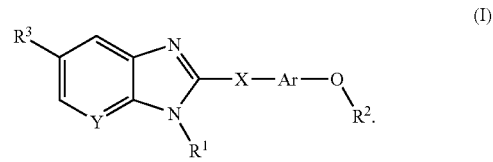

6 Claims, No Drawings

COMPOUNDS

CROSS-REFERENCE TO RELATED APPLICATIONS

This application is a US National Stage of International Application No. PCT/SE02/00769 that was filed on Apr. 18, 2002. The International Application claims priority under 35 U.S.C. § 119(a) to Swedish Application No. 0101387-9 filed Apr. 20, 2001.

FIELD OF THE INVENTION

The present invention is directed to novel compounds and salts thereof which are agonists at the CB2 receptor. The compounds are useful in therapy, in particular for the therapy of pain. The present invention also relates to processes for the manufacture of the novel compounds, to pharmaceutical compositions containing them, and to the use of the compounds in therapy, particularly for the therapy of pain.

BACKGROUND OF THE INVENTION

Two cannabinoid receptors are known: one is expressed predominately in the central nervous system (CB1), whereas the other is located in the periphery and is primarily restricted to cells and tissues derived from the immune system (CB2). (Abood and Martin *Int. Rev. of Neurobio.* 39, 197–221, (1996).

While agonists at the CB1 receptor, and mixed agonists, are highly effective in anti-nociception models in animals, it has not proved possible to separate the desired analgesic actions from the undesired CNS side-effects to any great degree. These undesired CNS side-effects are known to be mediated by the CB1 receptor.

A number of reports indicate an important role for CB2 in pathophysiology. In particular, Munro et. al. [*Nature* 365 61–65 (1993)] have found that the expression of the CB2 receptor is induced under conditions of immune cell activation. Hanus et. al [*PNAS* 96, 14228–14233 (1999)] have recently provided evidence that a CB2 agonist elicits anti-inflammatory and peripheral analgesic activity. Moreover, Mazzari et. al. [*Soc. Neurosci. Abstr.* 23 652 (1995)] have shown that CB2 activation inhibits mechanical hyperalgesia associated with nerve injury. These results indicate that the CB2 receptor is an interesting target for the discovery of novel analgesics which would be expected to be devoid of CB1 mediated side-effects associated with conventional cannabinoid agonists, e.g., tetrahydrocannabinol (THC). Moreover, as the CB2 receptors are limited to the periphery, selective CB2 agonists may be expected to reduce pain without the psychoactive side effects and the commonly perceived abuse potential of centrally acting cannabimimetic (CB1) or opiate drugs.

Analgesics that have been identified and are existing in the prior art have many disadvantages among which are poor pharmacokinetics and loss of analgesic activity when administered by systemic routes.

DETAILED DESCRIPTION OF THE INVENTION

The compounds according to the present invention are defined by the formula L and a pharmaceutically acceptable salt thereof, and diasteriomers, and enantiomers and mixtures thereof:

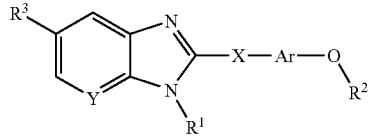

wherein $R^1$ is selected from the group consisting of —($C_1$–$C_8$)alkyl, —($C_2$–$C_8$)alkenyl, $R^4{}_2N(C_1$–$C_6)$alkyl-, $R^4{}_2NC(=O)(C_1$–$C_6)$alkyl-, $R^4O(C_1$–$C_6)$alkyl-, $R^4OC(=O)(C_1$–$C_6)$alkyl-, $R^4C(=O)(C_1$–$C_6)$alkyl-, $R^4C(=O)NR^4(C_1$–$C_6)$alkyl-, $R^4{}_2NSO_2(C_1$–$C_6)$alkyl-, $R^4CSO_2NR^4(C_1$–$C_6)$alkyl-, $R^4{}_2NC(=O)NR^4(C_1$–$C_6)$alkyl-, $R^4{}_2NSO_2NR^4(C_1$–$C_6)$alkyl-, aryl($C_1$–$C_6$)alkyl-, aroyl($C_1$–$C_6$)alkyl, heteroaryl($C_1$–$C_6$)alkyl, heteroaroyl($C_1$–$C_6$)alkyl, heterocycloalkyl($C_1$–$C_6$)alkyl, bicyclic heteroaryl($C_1$–$C_6$)alkyl and bicyclic heteroaroyl($C_1$–$C_6$)alkyl;

$R^1$ moieties comprise unsubstituted —($C_2$–$C_8$)alkenyl, and —($C_1$–$C_8$)alkyl unsubstituted or substituted by one or more moieties independently selected from the group consisting of halogen, cyano, acetoxymethyl, and nitro;

Ar is an optionally substituted aryl moiety;

$R^2$ is —($C_1$–$C_6$)alkyl, unsubstituted or substituted (on 1–6 carbons) by one or more fluorine substituents, or ($C_3$–$C_6$) cycloalkyl;

$R^3$ is selected from the group consisting of:

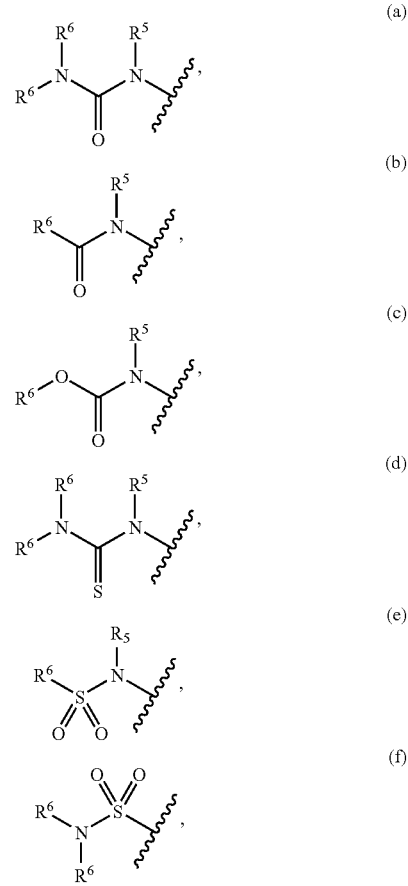

-continued

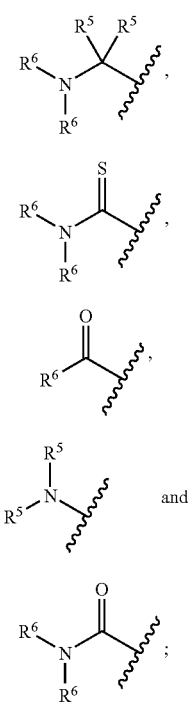

R[4] is a moiety independently selected from the group consisting of —H, —$(C_1-C_6)$alkyl, —$(C_2-C_6)$alkenyl and —$(C_2-C_6)$alkynyl;

NR[4]$_2$ comprises compounds wherein NR[4]$_2$ forms a heterocyclyl ring system, e.g., pyrrole, piperidine, piperazine, or pyrrolidinone;

R[5] moieties are independently selected from the group consisting of —H, —$(C_1-C_6)$alkyl, —$(C_2-C_6)$alkenyl and heterocyclyl;

NR[5]$_2$ comprises compounds wherein NR[5]$_2$ forms a heterocyclyl ring system, e.g., pyrrole, piperidine, piperazine, or pyrrolidinone;

R[6] moieties are independently selected from the group consisting of: —H, —$(C_1-C_6)$alkyl, —$(C_2-C_6)$alkenyl and —$(C_1-C_6)$alkanoyl, heterocyclyl, heterocyclyl$(C_1-C_3)$ alkyl, aryl, aryl$(C_1-C_3)$alkyl, heteroaryl, heteroaryl$(C_1-C_3)$ alkyl, bicyclic heteroaryl, and bicyclic heteroaryl$(C_1-C_3)$ alkyl;

R[5] and R[6] may combine to form a 5–7 membered heterocycle, e.g., pyrrole, piperidine, piperazine, pyrrolidinone, homopiperazine, or hexamethyleneimine;

X is selected from the group consisting of —C(R[5])$_2$—, —NR[5]—, C(=O)—, —CH$_2$—CH$_2$—, —CH=CH—, —O—, —C(R)(R')—, and —S(O)$_n$— (where n=0, 1 or 2), where R and R'=$(C_1-C_6)$alkyl, OR", or H, and R"=H or $(C_1-C_6)$alkyl; and Y is C or N.

The term alkyl, when used herein includes straight chain, branched chain and cyclic substituents, for example, methyl, ethyl, n-propyl, isopropyl, n-butyl, isobutyl, t-butyl, cyclopropylmethyl and cyclopentyl, and moieties on alkyl chains may be anywhere on the chain, such that amino$(C_1-C_6)$alkyl includes 1-aminopropyl and 2-aminopropyl.

The term halogen, when used herein comprises fluorine, chlorine, bromine and iodine.

The term aryl moiety includes aromatic carbocycles, five-membered heteroaromatic ring systems, six-membered heteroaromatic ring systems and bicyclic heteroaromatic ring systems.

Aromatic carbocycle includes phenyl and naphthyl.

A five-membered heteroaromatic ring system is a monocyclic aromatic ring system having five ring atoms wherein 1, 2 or 3 ring atoms are independently selected from N, O and S.

Preferably, five-membered heteroaromatic ring systems are selected from the group consisting of thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

A six-membered heteroaromatic ring system is a monocyclic aromatic ring system having six ring atoms wherein 1, 2 or 3 ring atoms are N.

Preferably, six-membered heteroaromatic ring systems are selected from the group consisting of pyridyl, pyrazinyl, pyrimidinyl, triazinyl and pyridazinyl.

A bicyclic heteroaromatic ring system is a ring system having two five- or six-membered heteroaromatic rings, or a phenyl and a five- or six-membered heteroaromatic ring, or a phenyl and a heterocyclyl ring, or a five- or six-membered heteroaromatic ring and a heterocyclyl ring; connected by a ring fusion, said bicyclic heteroaromatic ring system comprising 8 to 12 ring atoms wherein 1, 2 or 3 of the ring atoms are independently selected from N, O and S.

Bicyclic heteroaromatic ring systems are preferably selected from the group consisting of indole, indoline, quinoline, tetrahydroquinoline, isoquinoline, tetrahydroisoquinoline, 1,4-benzodioxan, coumarin, dihydrocoumarin, benzofuran, 2,3-dihydrobenzofuran, 1,2-benzisoxazole, benzothiophene, benzoxazole, benzthiazole, benzimidazole, benztriazole, pyrolizidine, and quinolizidine.

A heterocyclyl or heterocyclic moiety is a saturated or partially saturated ring system having 3 to 7 ring atoms wherein 1, 2 or 3 ring atoms are independently selected from N, O and S.

Heterocyclyl moieties are preferably selected from the group consisting of aziridine, oxirane, thiirane, azetidine, oxetane, thietane, pyrrolidine, pyrroline, imidazolidine, pyrazolidine, dioxolane, sulfolane 2,3-dihydrofuranyl, 2,5-dihydrofuranyl, tetrahydrofuranyl, thiophanyl, piperidine, piperazine, morpholine, 2,3-dihydropyranyl, tetrahydropyranyl, 1,4-dihydropyridinyl, 1,4-dioxanyl, 1,3-dioxanyl, dioxanyl, homopiperidinyl, homopiperazinyl, 1,3-dioxepane, 4,7-dihydro-1,3-dioxepin, and hexamethylene oxide.

Aromatic, heteroaromatic, heterocyclyl, and bicyclic heteroaromatic moieties are unsubstituted or substituted on ring carbons preferably by moieties independently selected from the group consisting of halogen, trifluoromethyl, cyano, nitro, hydroxy, —NR[4]$_2$, —C(=O)OR[4], —C(=O)R[4], —C(=O)NR[4]$_2$, —NR[4]C(=O)R[4], —$(C_1-C_6)$alkyl, —$(C_2-C_6)$alkenyl, —$(C_2-C_6)$alkynyl, —OR[4], —SR[4], —SO$_2$R$_4$, oxo (=O), imino (=NR[4]), thio (=S), and oximino (=N—OR[4]).

Ring nitrogen atoms, of five-membered heteroaromatic, heterocyclyl or bicyclic heteroaromatic ring systems are unsubstituted or substituted, if such substitution is chemically possible without quaternization of said ring nitrogen, preferably with moieties independently selected from the group consisting of —$(C_1-C_6)$alkyl, and —C(=OR[4].

Substituents —$(C_1-C_6)$alkyl, —$(C_2-C_6)$alkenyl and —$(C_1-C_6)$alkanoyl are unsubstituted or substituted on one or more carbons by moieties independently selected from the group consisting halogen, hydroxy, —$OR^4$ and —$NR^4_2$.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I which acts as a CB2 agonist. The synthesis of optically active forms may be carried out by standard techniques of organic chemistry well known in the art, for example by chiral chromatographic separation of a racemate, by synthesis from optically active starting materials or by asymmetric synthesis.

It will also be appreciated that certain compounds of the present invention may exist as geometrical isomers, for example E and Z isomers of alkenes. The present invention includes any geometrical isomer of a compound of Formula I which acts as a CB2 agonist. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I which act as CB2 agonists.

In preferred embodiments of formula I, if $R_1$ represents $R^4_2N(C_1-C_6)$alkyl-, wherein to both occurrences of $R_4$ represent —$(C_1-C_6)$alkyl, then $R_3$ is selected from the moieties (as set forth above) (a), (c), (d), (e), (f), (g), (h), and (k), and optionally (b) and (i) (except where $R_6$ is —$(C_1-C_6)$alkyl (especially methyl, e.g., $R_3$ represents acetyl or acetamido)) and (j) (except where $R_5$ is H for both occurrences, e.g., $R_3$ represents a primary amine).

Preferred compounds of the present invention are those of Formula I wherein;

$R^1$ is selected from the group consisting of —$(C_1-C_8)$ alkyl —$(C_2-C_8)$alkenyl, aryl$(C_1-C_6)$alkyl, $R^4_2N(C_1-C_6)$ alkyl-, $R^4O(C_1-C_6)$alkyl-, -heterocycloalkyl$(C_1-C_6)$alkyl (4- to 8-membered), and heteroaryl$(C_1-C_6)$alkyl;

wherein aryl and heteroaryl $R^1$ moieties are unsubstituted or substituted by —$(C_1-C_6)$alkyl, acetoxymethyl, or halogen;

$R^2$ is selected from the group consisting of —$CH_3$, —$CH_2CH_3$, —$CH(CH_3)_2$, $(C_3-C_5)$cycloalkyl, and $CF_3$;

$R^3$ is selected from the group consisting of:

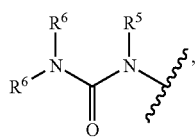

(a)

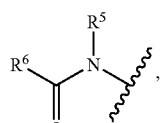

(b)

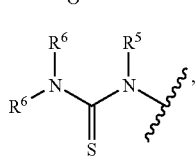

(d)

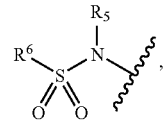

(e)

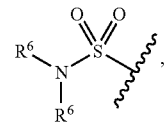

(f)

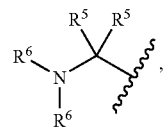

(g)

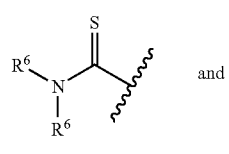

(h)

and

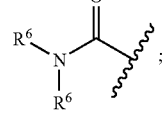

(k)

;

Ar is an aryl moiety; unsubstituted or substituted by one or more moieties independently selected from the group consisting of $(C_1-C_6)$alkyl, halogen, trifluoromethyl, cyano, nitro, hydroxy and —$OR^4$;

X is selected from the group consisting of —$CH_2$—, —$CH_2CH_2$—, —$C(=O)$—, —S—, —O—, —$C(R)(R')$—, and —$N(R)$—, where R and R'=$(C_1-C_6)$alkyl, OR", or H, and R"=H or $(C_1-C_6)$alkyl;

when Ar is a phenyl or six-membered heteroaromatic ring system, X is positioned on ring Ar in a 1,4 relationship with respect to the —O—$R^2$ group;

when Ar is a 5-membered heteroaromatic ring system, X is positioned on ring Ar in a 1,3 relationship with respect to the —O—$R^2$ group;

$R^4$ is independently selected from the group consisting of —H and —$(C_1-C_6)$alkyl;

$R^5$ is independently selected from the group consisting of —H, —$(C_1-C_6)$alkyl and —$(C_2-C_6)$alkenyl; and $R^6$ is independently selected from the group consisting of —H, —$(C_1-C_6)$alkyl, —$(C_2-C_6)$alkenyl, and heteroaryl;

wherein said heteroaryl is unsubstituted or substituted by —$(C_1-C_6)$alkyl.

More preferred compounds of the present invention are those of Formula I wherein;

$R^1$ is selected from the group consisting of cyclopropylmethyl, ethyl, propyl, allyl, isopentyl, benzyl, methoxyethyl, dinmethylaminoethyl, 4-pyridylmethyl, 2-pyridylmethyl, 1-pyrrolylethyl, 1-morpholinoethyl, cyclohexylmethyl, 2-pyrrolidylmethyl, N-methyl-2-pyrrolidylmethyl, 2-piperidylmethyl, N-methyl-2-piperidylmethyl, 3-thienylmethyl, 2-tetrahydrofuranylmethyl, (2-nitrothiophene-5-yl) methyl, (1-methyl-1H-imidazole-2-yl)methyl, (5-(acetoxymethyl)-2-furanyl)methyl, (2,3-dihydro-1H-isoindole-1-yl)methyl, and 5-(2-methylthiazolyl);

$R^2$ is selected from the group consisting of —$CH_3$, —$CH_2CH_3$, —$CH(CH_3)_2$, and $CF_3$;

$R^4$ is —$(C_1$–$C_6)$alkyl;

$R^5$ is selected from the group consisting of —H, —$CH_3$, —$CH_2CH_3$, —CH=$CH_2$ and —$CH_2$—CH=$CH_2$;

$R^6$ is selected from the group consisting of —$CH_3$, —$CH_2CH_3$, —CH=$CH_2$, —$CH_2$—CH=$CH_2$, —$CH_2$—$CH_2$—CH=$CH_2$, —$CH_2CH(CH_3)_2$ and 5-methyl-3-isoxazole;

Ar is a phenyl or six-membered heteroaromatic ring system, either of which may be unsubstituted or substituted bygone or more moieties independently selected from the group consisting of $(C_1$–$C_6)$alkyl, halogen, trifluoromethyl, cyano, nitro, hydroxy and —$OR^4$;

X is selected from the group consisting of —$CH_2$—, —$CH_2CH_2$—, —S—, —O—, —C(=O)—, —C(R)(R')—, and —N(R)—, where R and R'=$(C_1$–$C_6)$alkyl, OR", or H, and R"=H or $(C_1$–$C_6)$alkyl; and X is positioned on ring Ar in a 1,4 relationship with respect to the —O—$R^2$ group.

Most preferred compounds of the present invention are those of Formula I wherein:

$R^2$ is —$CH_2CH_3$;

Ar is unsubstituted phenyl or pyridyl;

X is selected from the group consisting of —$CH_2$—, —$CH_2CH_2$—, —S—, —O—, —C(R)(R')—, and —N(R)—, where R and R'=$(C_1$–$C_6)$alkyl, OR", or H, and R"=H or $(C_1$–$C_6)$alkyl;

X is positioned on ring Ar in a 1,4 relationship with respect to the —O—$R^2$ group; and $R^4$ is methyl.

In certain preferred compounds, X is selected from the group consisting of $CH(CH_3)$—, —$C(CH_3)_2$—, —CH(OH)—, —NH—, and —$N(CH_3)$—; most preferably $CH(CH_3)$.

We have now found that the compounds of the present invention, exhibit selective activity at the CB2 receptor site, and are useful in the relief of pain, particularly chronic pain, e.g., chronic inflammatory pain, neuropathic pain, back pain, cancer pain and visceral pain. Compounds of the present invention will also be useful in treating acute pain. Additionally, compounds of the present invention are useful in other disease states in which degeneration or dysfunction of CB2 receptors is present or implicated.

Within the scope of the invention are also salts of the compounds of the formula I. Generally, pharmaceutically acceptable salts of compounds of the present invention may be obtained using standard procedures well known in the art, for example by reacting a sufficiently basic compound, for example an ally amine with a: suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

Also within the scope of the present invention is use of compounds of the present invention in therapy.

The novel compounds of the present invention are useful in therapy, especially for the therapy of various pain conditions including, but not limited to: acute pain, chronic pain, neuropathic pain, acute pain, back pain, cancer pain, and visceral pain.

In use for therapy in a warm-blooded animal such as a human, a CB2 agonist will generally be administered in the form of a conventional pharmaceutical composition, and generally the composition may be in a form suitable for oral or sublingual administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general, the above compositions may be prepared in a conventional manner using conventional carriers. The compositions of the present invention are advantageously presented in unit dosage form.

A therapeutically effective amount for the practice of the present invention may be determined, by the use of known criteria including the age, weight and response of the individual patient, and interpreted within the context of the disease which is being treated or which is being prevented, by one of ordinary skill in the art.

Also within the scope of the invention is the use of any compound according to formula I above, for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, acute pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above. The term therapy within the context of the present invention means to administer a an effective amount of a compound of the present invention, to mitigate either a pre-existing disease state, acute or chronic, or a recurring condition. This definition also encompasses prophylactic therapies for prevention of recurring conditions and continued therapy for chronic disorders.

Pharmaceutical Compositions

The novel compounds according to the present invention may be administered orally, sublingually, intramuscularly, subcutaneously, topically, intranasally, intraperitoneally, intrathoracially, intravenously, epidurally, intrathecally, intracerebroventricularly and by injection into the joints.

Preferred routes of administration are orally, intravenously or intramuscularly.

The dosage will depend on the route of administration, the severity of the disease, age and weight of the patient and other factors normally considered by the attending physician, when determining the individual regimen and dosage level as the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Salts include, but are not limited to, pharmaceutically acceptable salts. Examples of pharmaceutically acceptable salts within the scope of the present invention include: acetate, benzenesulfonate, benzoate, bicarbonate, bitartrate, carbonate, citrate, fumarate, gluconate, glutamate, hydrobromide, hydrochloride, lactate, maleate, mandelate, mesylate, phosphate/diphosphate, salicylate, succinate, sulfate, tartrate, choline, diethanolamine, ethylenediamine, meglumine, aluminum, calcium, magnesium, potassium, sodium, and zinc.

Examples of pharmaceutically unacceptable salts within the scope of the present invention include: hydroiodide, perchlorate, tetrafluoroborate, lithium.

Preferred pharmaceutically acceptable salts are hydrochlorides, sulfates and bitartrates.

The hydrochloride and sulfate salts are particularly preferred.

The term composition is intended to include the formulation of the active component with encapsulating material as a carrier providing a capsule in which the active component (with or without other carriers) is surrounded by a carrier which is thus in association with it. Similarly, cachets-are included.

Tablets, powders, cachets, and capsules can be used as solid dosage forms suitable for oral administration.

Liquid from compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical compositions is in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Methods of Preparation

Process A1

Process A1 for manufacture of compounds with the general Formula I

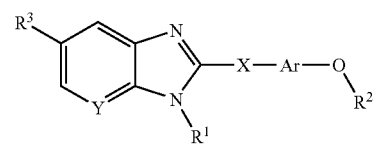

comprises the following steps:

Compounds of the general Formula II

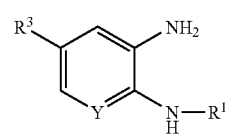

wherein R1, R3 and Y are as defined for Formula I, can be reacted with compounds of the general Formula III;

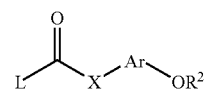

wherein $R^2$, Ar, and X are as defined for Formula I and L is —OH or a leaving group such as a halide, O-tosyl, or O-mesyl. It is convenient to conduct this reaction in an inert solvent such as toluene at ambient temperature for 20 minutes. Following this, a catalytic amount of concentrated HCl is added and the mixture is heated for 12 hours at 85° C. Work-up is by aqueous extraction and purification of the product is by normal or reverse phase chromatography.

Process A2

Process A2 for manufacture of compounds with the general Formula II comprises the following steps:

Compounds of the general Formula IV

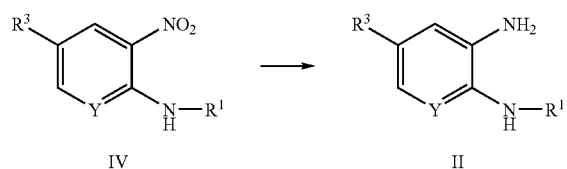

wherein $R^1$, $R^3$ and Y are as defined for Formula I, can be reduced to the corresponding aniline (Formula II) by reaction with hydrogen under a pressure of 10–50 pounds per square inch. It is convenient to conduct this reaction in an inert solvent such as ethanol, methanol or tetrahydrofuran at ambient temperature. The reaction is catalyzed by a transition metal catalyst, conveniently 5–10% palladium on finely divided carbon.

Process A3

Process A3 for manufacture of compounds with the general Formula IV comprises the following steps:

Compounds of the general Formula V:

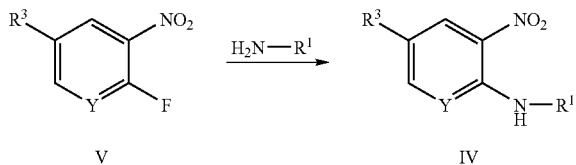

wherein $R^1$, $R^3$ and Y are as defined for Formula I, is reacted with a primary amine. It is convenient to conduct this reaction in a protic solvent such as 80% ethanol at a temperature of 50–100° C. Work-up is conveniently accomplished by aqueous extraction, and purification is conveniently performed by normal phase chromatography.

Process A4

Process A4 for manufacture of compounds with the general Formula III comprises the following steps:

Compounds of the general Formula VI:

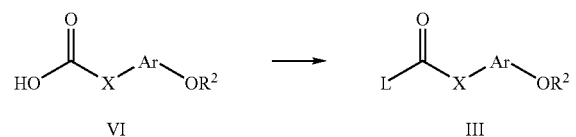

wherein $R^2$, Ar, and X are as defined for Formula I and L is —OH or a leaving group such as a halide, O-tosyl, or O-mesyl, is reacted with a halogenating agent such as thionyl chloride. It is convenient to conduct this reaction in an inert solvent such as benzene or toluene at a temperature of 25–100° C. Work-up is conveniently accomplished by removing the solvent under reduced pressure and purification is conveniently performed by distillation.

Process A5

Process A5 for manufacture of compounds with the general Formula VIII comprises the following steps:

Compounds of the general Formula VII (prepared via process A1)

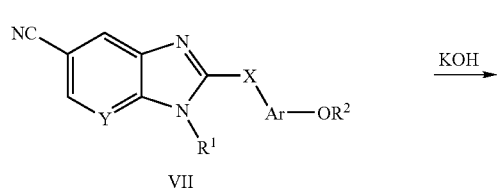

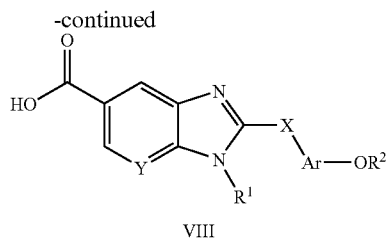

wherein $R^1$, $R^2$, Ar, X and Y are as defined for Formula I and are prepared via general processes described above, are hydrolyzed using KOH. This reaction is conveniently performed in an aqueous solvent mixture such as one to one ethanol/water at reflux temperature. After neutralization, the product is conveniently isolated by filtration of the cooled reaction mixture.

Process A6

Alternately, Process A6 for manufacture of compounds with the general formula VIII comprises the following steps:

Compounds of general formula X (prepared via process A1);

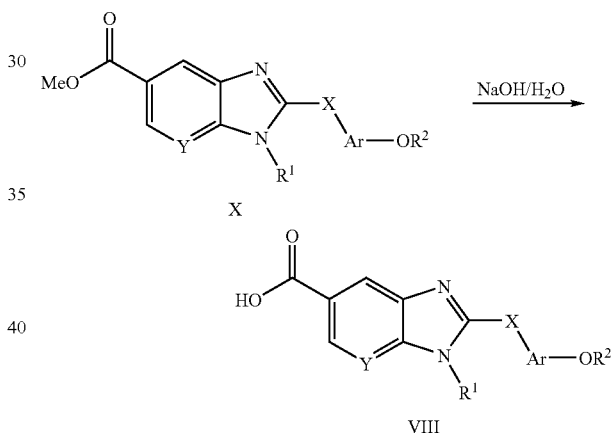

wherein $R^1$, $R^2$, Ar, X and Y are as defined for Formula I and are prepared via general processes described above, are converted to the corresponding carboxylic acid VIII by hydrolysis of the ester X using an aqueous base such as sodium hydroxide to the corresponding carboxylic acid.

Process A7

Process A7 for manufacture of compounds with the general Formula IX comprises the following steps:

Compounds of Formula VIII

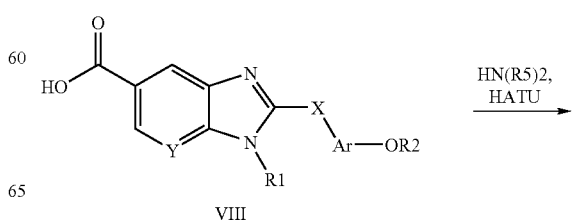

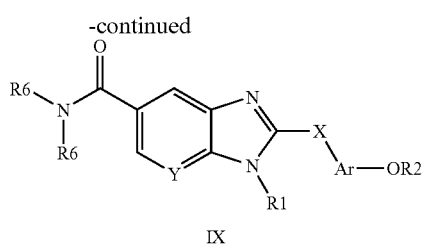

IX wherein $R^1$, $R^2$, Ar, X and Y are as defined for Formula I and are prepared via general processes described above are converted to the corresponding amide by reaction with a primary or secondary amine in the presence of an acid activating agent such as HATU [O-(7-azabenzotriazol-1-yl)-N,N,N',N'-tetramethyluronium hexafluorophosphate], HBTU [O-benzotriazol-1-yl)-N,N,N',N'-tetramethyluronium hexafluorophosphate] or TBTU [O-(1H-Benzotriazol-1-yl)-N,N,N',N'-pentamethylene-uronium tetrafluoroborate]. The reaction is conveniently performed in a polar aprotic solvent such as DMF at ambient temperature in association with a tertiary amine such as triethyl amine or diisopropylethylamine which serves is as an acid scavenger. The product is conveniently isolated by an aqueous extraction and purified by normal phase chromatography.

Process A8

Process A8 for manufacture of compounds with the general Formula XI comprises the following steps:

Compounds of Formula IX (prepared via process A1 or A7);

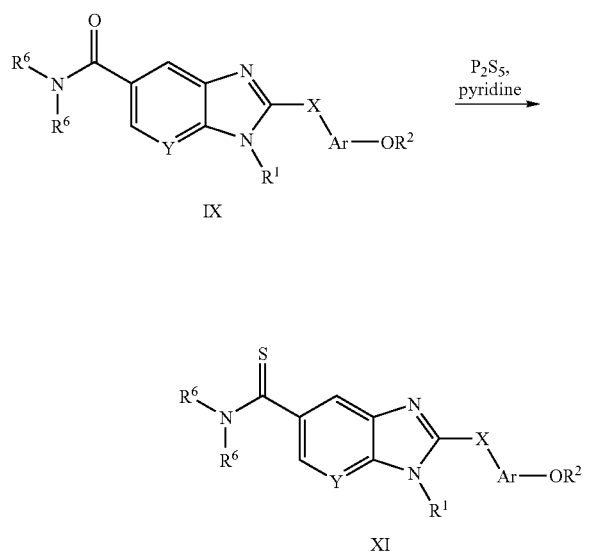

wherein $R^1$, $R^2$, $R^6$, Ar, X and Y are as defined for Formula I and are prepared via general processes described above, are converted to the corresponding thio amide (Formula XI) by reaction with $P_2S_5$. The reaction is conveniently performed in pyridine at a temperature of 100°. The product is conveniently isolated by an aqueous extraction of the decanted portion of the reaction mixture and purified by normal phase chromatography.

Process A9

Process A9 for manufacture of compounds with the general Formula XII comprises the following steps:

Compounds of formula VII (prepared via process A1);

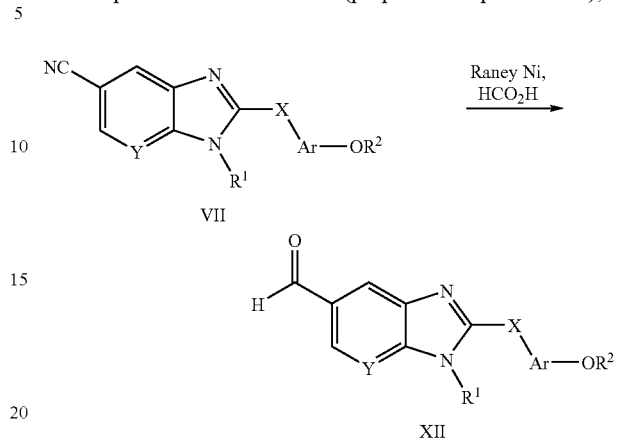

wherein $R^1$, $R^2$, Ar, X and Y are as defined for Formula I and are prepared via general processes described above, are catalytically reduced using a catalytic amount of Raney nickel in 50% aqueous formic acid. This reaction is conveniently performed in an acidic aqueous solvent mixture such as in 50% aqueous formic acid at 90° C. The product is conveniently isolated by filtration of the cooled reaction mixture through a pad of diatomaceous earth, concentration and purification via normal phase chromatography.

Process A10

Process A10 for manufacture of compounds with the general Formula XIII comprises the following steps:

Compounds of Formula XII

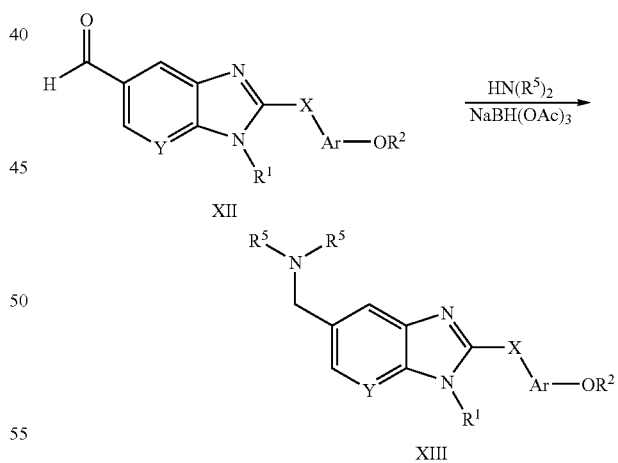

wherein $R^1$, $R^2$, $R^5$, Ar, X and Y are as defined for Formula I and are prepared via general processes described above, are reductively aminated using a primary or secondary amine in the presence of a suitable reducing agent such as sodium triacetoxyborohydride. This reaction is conveniently performed in tetrahydrofuran with 1–1.5 equivalents of acetic acid and 1–1.5 equivalents of sodium triacetoxyborohydride at ambient temperature. The product is conveniently isolated by decomposition of the borate ester intermediate with 1 N HCl followed by an aqueous extraction. Concentration of the organic extract yields the crude product and purification is accomplished via normal phase chromatography.

Process A11

Process A11 for manufacture of compounds with the general Formula XIV comprises the following steps:

Compounds of formula XII

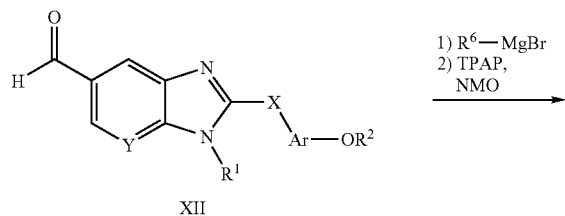

XII

1) R⁶—MgBr
2) TPAP, NMO

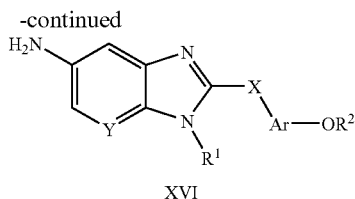

XIV wherein $R^1$, $R^2$, $R^6$, Ar, and X are as defined for Formula I and are prepared via general processes described above, are coupled with an organometellic agent such as a Grignard reagent followed by oxidation of the intermediate alcohol to the ketone. The Grignard reaction is conveniently performed in tetrahydrofuran with six equivalents of an organomagnesium halide such as methyl magnesium bromide at 0° C. The product is conveniently isolated by decomposition of excess organometallic reagent by adding water followed by an aqueous extraction and concentration of the organic extract. Oxidation of this intermediate alcohol is accomplished by reaction with a catalytic amount (about 5 mol %) of tetrapropylammonium perruthenate (TPAP) and 1–1.5 equivalents of N-methylmorpholine-N-oxide (NMO) in the presence of 4 Å molecular sieves. This reaction is conveniently done in dichloromethane at ambient temperature. The product is conveniently isolated by concentration of the reaction mixture and purification via normal phase chromatography.

Process A12

Process A12 for the manufacture of compounds with the general formula XVI comprises the following steps:

Compounds of the formula XV (which are prepared via process A1)

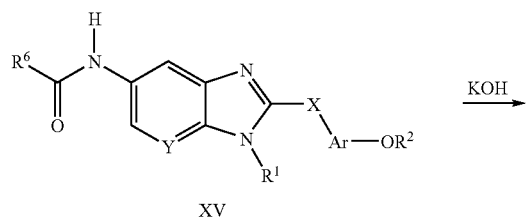

XV

KOH

-continued

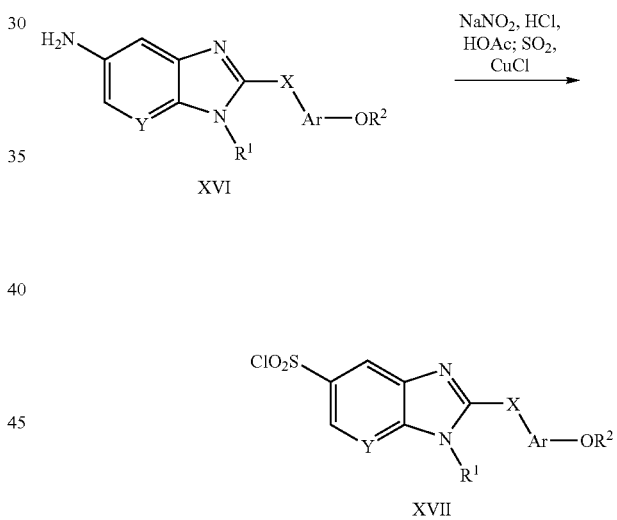

wherein $R^1$, $R^2$, $R^6$, Ar, X and Y are as defined for Formula I and are prepared via general processes described above are converted to the corresponding aniline by hydrolysis using a base such as potassium hydroxide in an aqueous solvent such as 50% aqueous ethanol. The reaction is conveniently performed at reflux temperature over an extended period of time (8–16 hours). The product is conveniently isolated by allowing the reaction mixture to cool to ambient temperature, acidifying the mixture with 1 N HCl and collecting the precipitated product by filtration.

Process A13

Process A13 for the manufacture of compounds with the general formula XVII comprises the following steps:

Compounds of the formula XVI wherein $R^1$, $R^2$, Ar, X and Y are as defined for Formula I and are prepared via general processes described above are converted to the corresponding sulfonyl chloride by reaction with sodium nitrite in aqueous HCl and acetic acid to give the intermediate diazonium salt. This reaction is conveniently performed at <−10° C. This intermediate diazonium salt is immediately converted to the sulfonyl chloride by dropwise addition to a freshly prepared saturated solution of sulfur dioxide in acetic acid in the presence of copper (I) chloride. This reaction is conveniently performed at between −10 and −5° C. The product is conveniently isolated by pouring the reaction mixture into ice water and extracting with dichloromethane and concentrating under vacuum. Sulfonyl chlorides of formula XVII are typically used without further purification.

Process A14

Process A14 for the manufacture of compounds of general formula XVIII comprises the following steps:

Compounds of formula XVII

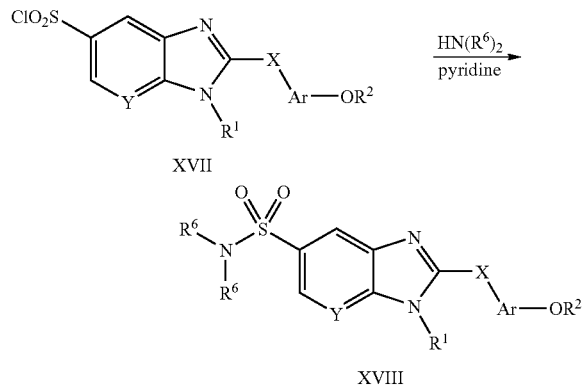

wherein $R^1$, $R^2$, $R^6$, Ar, and X are as defined for Formula I and are prepared via general processes described above are converted to the corresponding sulfonamide by reaction with a primary or secondary amine. The reaction is conveniently performed in a nonpolar solvent such as dichloromethane at ambient temperature in the presence of an acid scavenger such as pyridine. The product is conveniently isolated by an aqueous extraction and purified by normal phase chromatography.

Process A15

Process A15 for the manufacture of compounds of general formula XX comprises the following steps:

Compounds of formula XIX

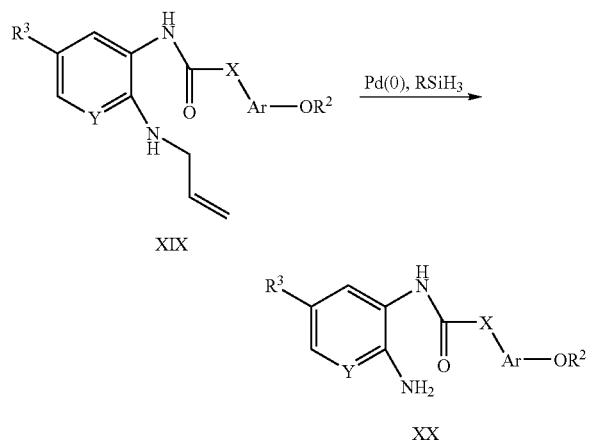

wherein $R^2$, $R^3$, Ar, X and Y are as defined for Formula I and are prepared using the above described Process A1 and are converted to compounds of formula XX by using palladium (0) mediated de-allylation reaction in the presence of a cation-scavenger, such as phenylsilane. The product is conveniently isolated by an aqueous extraction and purified by normal phase chromatography.

Process A16

Process A16 for the manufacture of compounds of general formula XX comprises the following steps:

Compounds of formula XXI

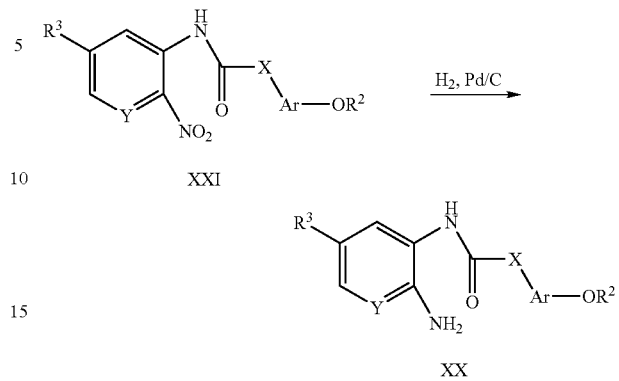

wherein $R^2$, $R^3$, Ar, X and Y are as defined for Formula I and are prepared using the above described Process A2 and are converted to compounds of formula XX under a palladium catalysed hydrogenation condition. The product is conveniently isolated by filtration and purified by normal phase chromatography or used directly without chromatography purification.

Process A17

Process A17 for the manufacture of compounds of general formula I comprises the following steps:

Compounds of formula XX

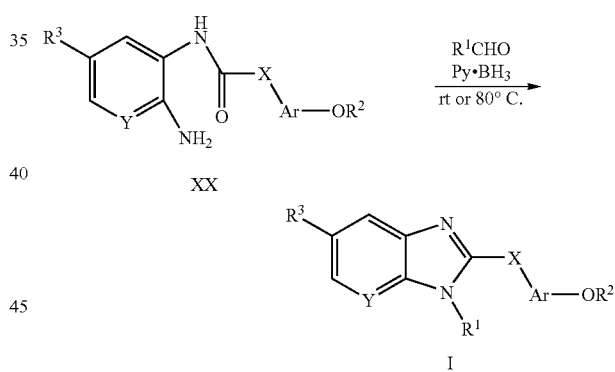

is wherein $R^1$, $R^2$, $R^3$, Ar, X and Y are as defined for Formula I and are converted to the corresponding compounds of general formula I by reacting with an aldehyde followed by borane reduction, in a one-pot fashion. The reaction is conveniently performed in a mixed solvent such as 1,2-dichloroethane and acetic acid at ambient or elevated temperature. The product is conveniently isolated by an aqueous extraction and purified by normal phase chromatography or reverse phase chromatography.

Process A18

A further aspect of the invention is a method for selectively reducing a nitro moiety ortho to an amino substituent on a phenyl or pyridyl ring of a compound in the presence of a nitro moiety para to the amino substituent, comprising treating a solution of the compound in a solvent, preferably a non-polar solvent such as ethyl acetate, with a palladium catalyst, such as Pd/C in the presence of hydrogen, optionally under pressure (e.g., 1–10 atmospheres, preferably 1–5 atmospheres, even more preferably 24 atmospheres of pressure). In certain embodiments, both nitro substituents are located para to the nitrogen of a pyridine ring. See Example 58B below for an exemplary protocol.

A further aspect of the present invention is intermediates of the general formulae VIII, X and XIII, below, and their use in the synthesis of compounds of formula I.

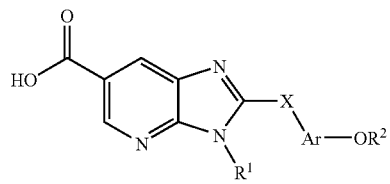

VIII

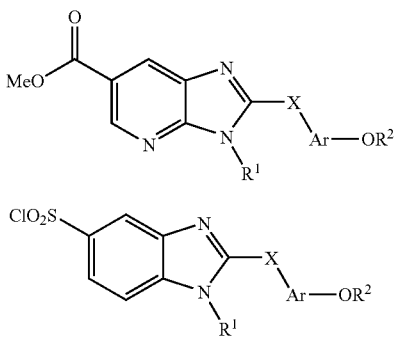

X

XVI

The compounds of the present invention may be synthesized according to the procedures described below in Schemes 1–15 on the following pages.

Scheme 1:
Synthetic route for Examples 2–12 and 14–17

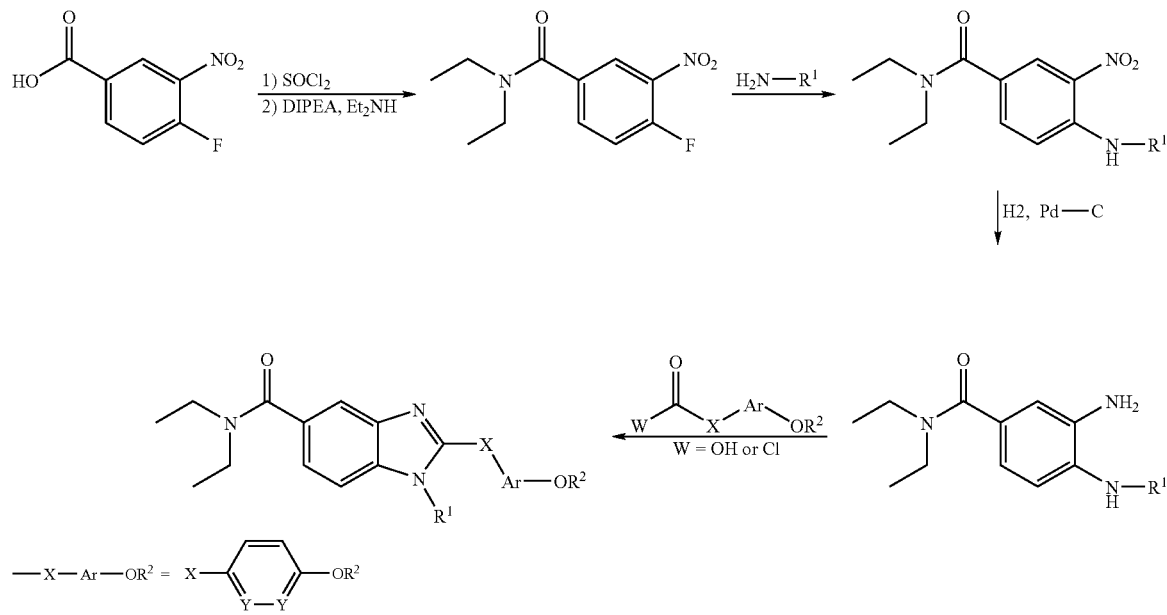

Scheme 2:
Synthetic route for Examples 20–22 and 24–25.

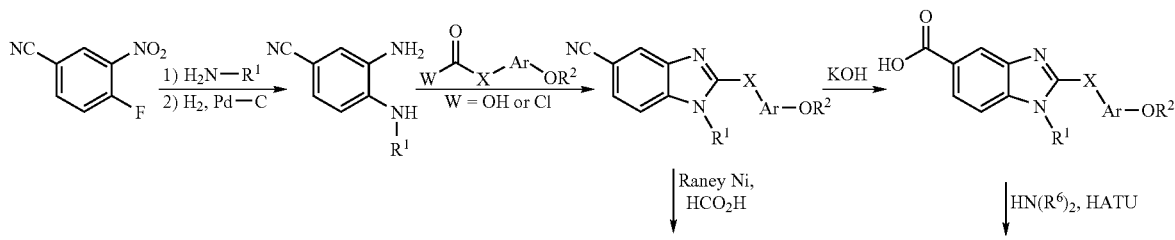

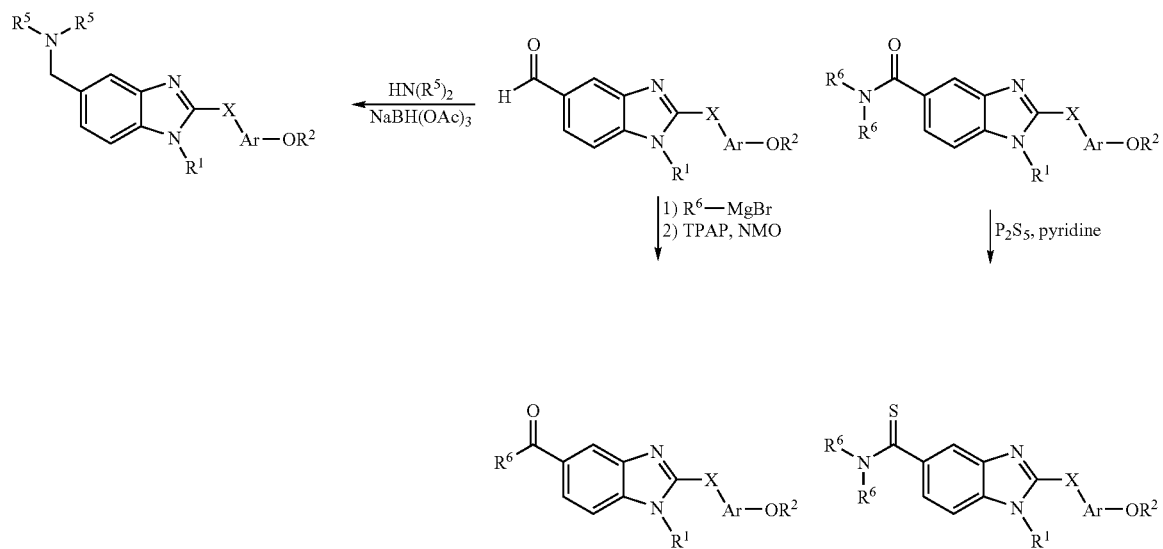
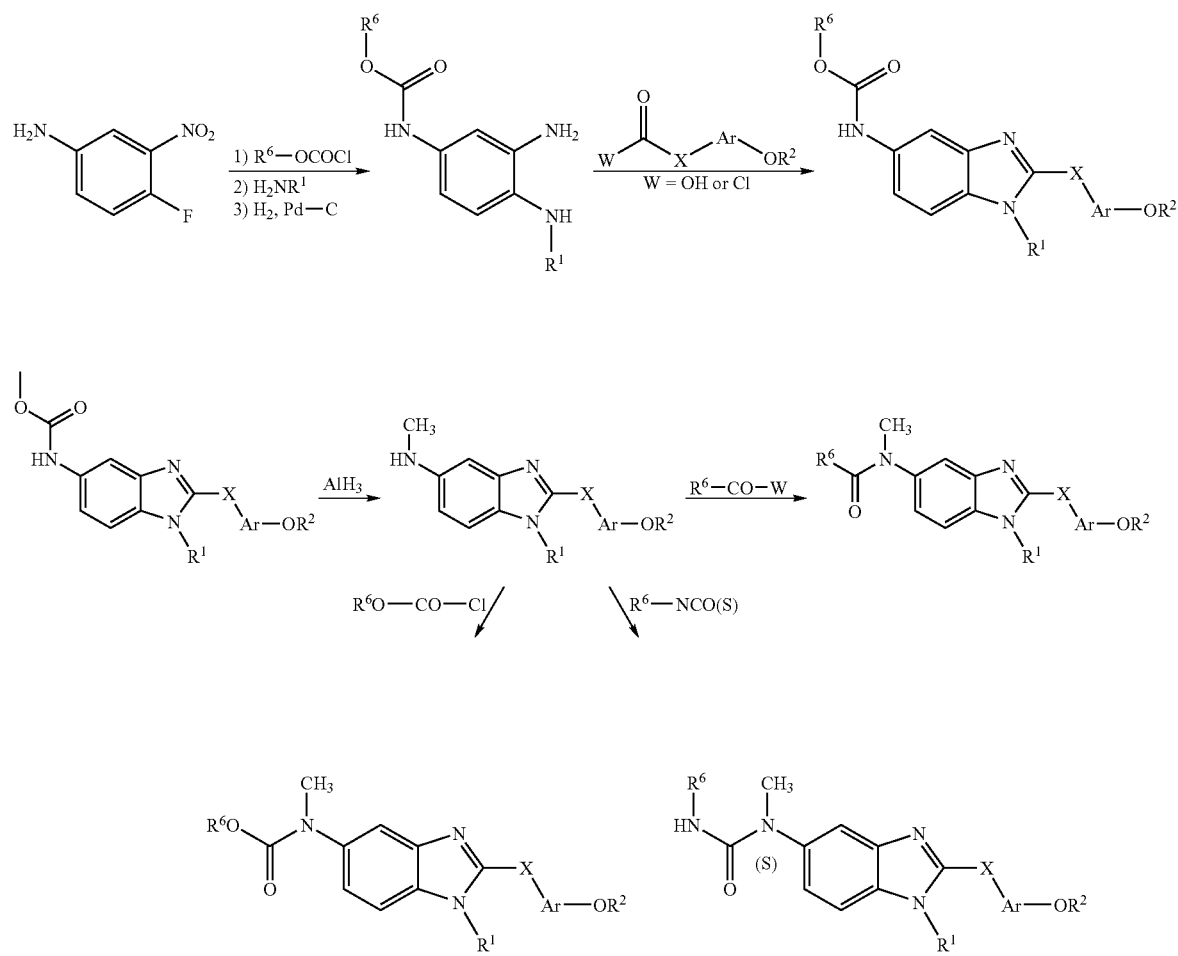
Scheme 3:
Synthetic route for Examples 13, 23, 26–31 and 52–56.

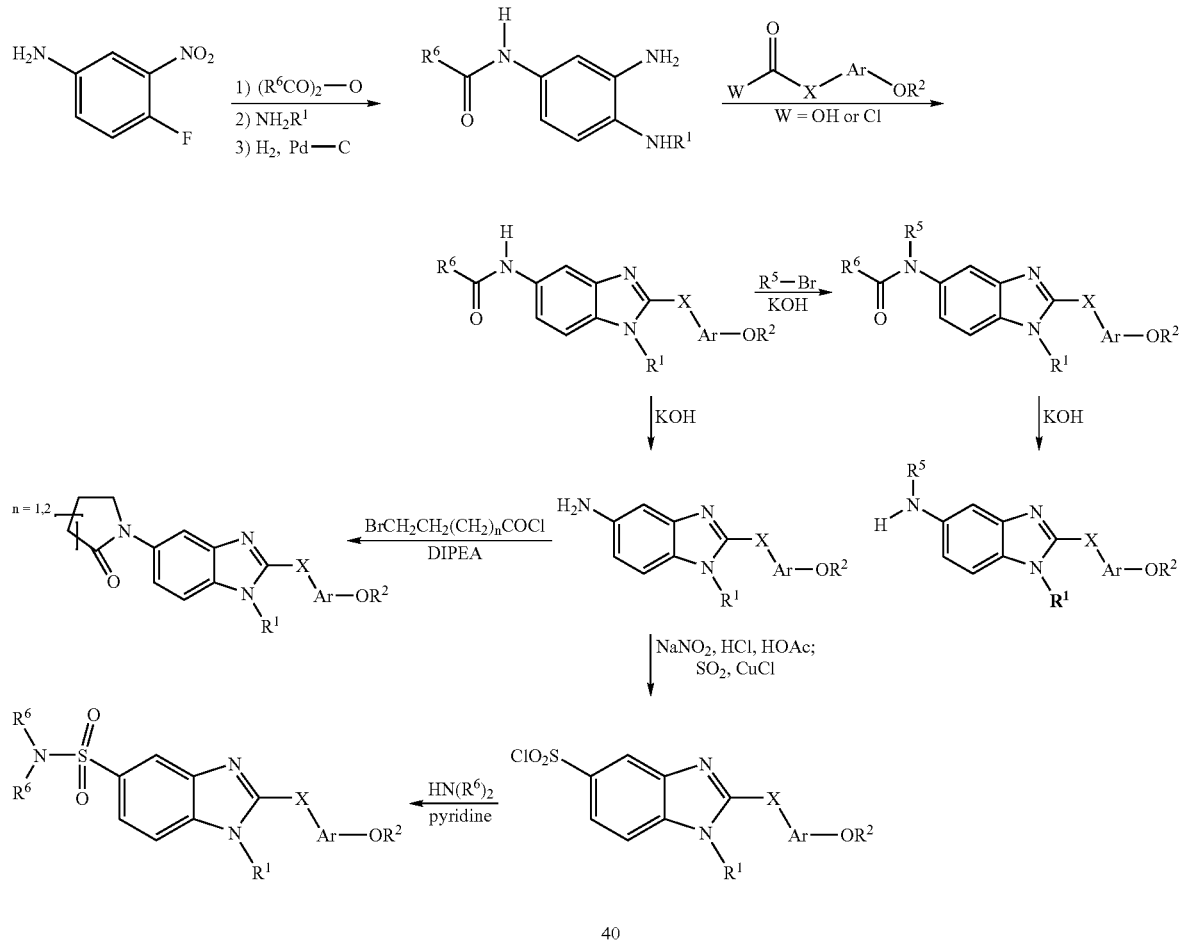
Scheme 4:
Synthetic route for Examples 32–36 and 51.
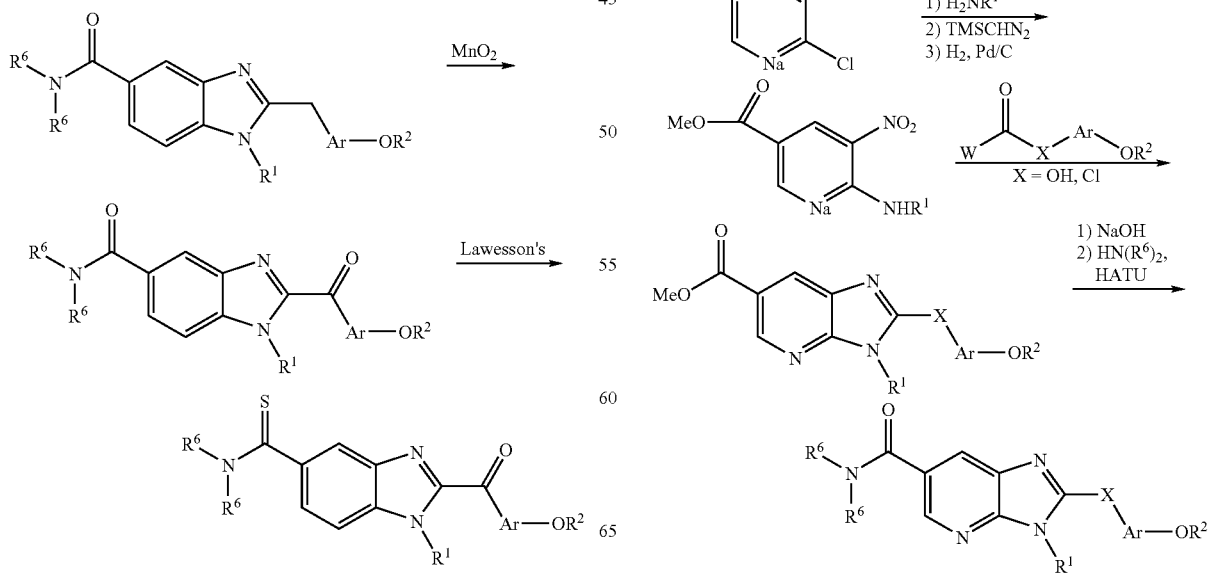
Scheme 5:
Synthetic routes to Examples 18, 19, 35 and 39.

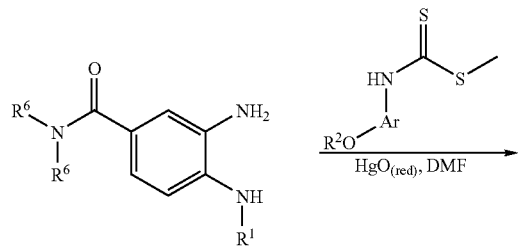
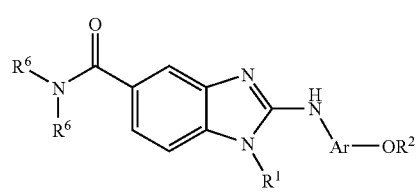
Scheme 6
Synthetic route to Examples 40–42 and 43–45.
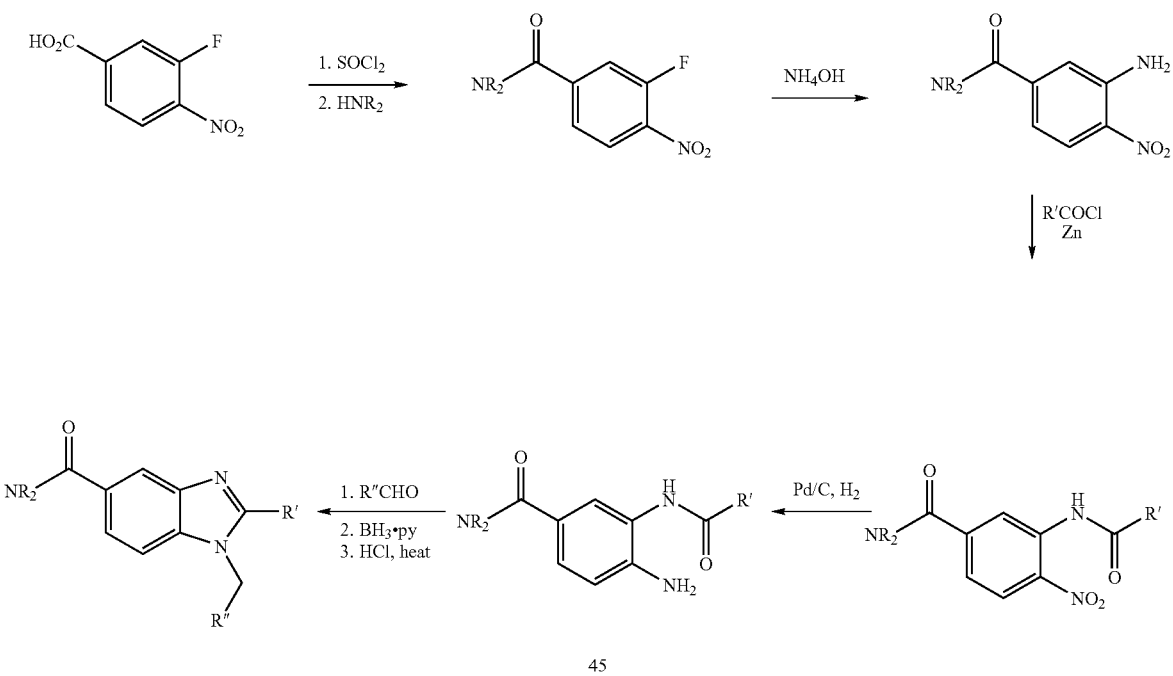
Scheme 7:
Synthetic route to Example 46.
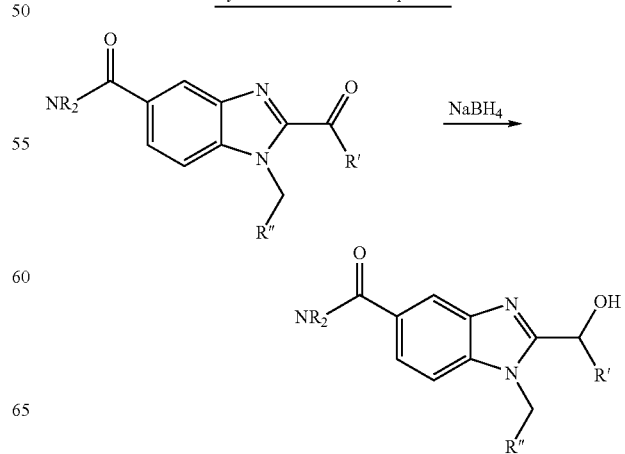

Scheme 8:
Synthetic route to Examples 47–49.
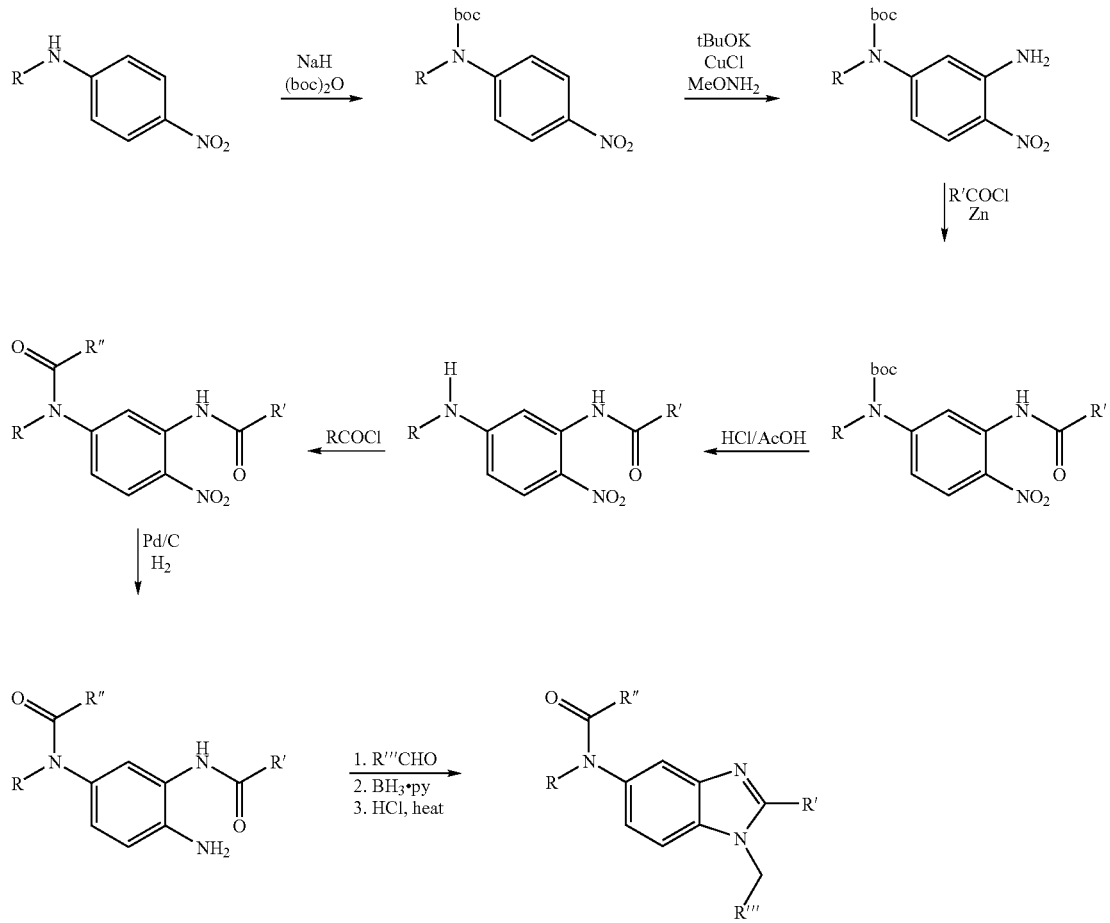
Scheme 9:
Synthetic route to Example 50.
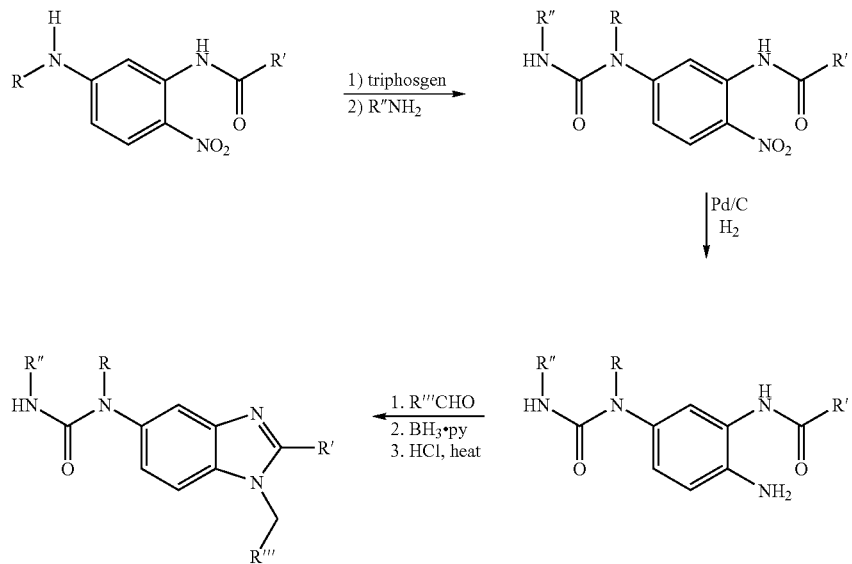

Scheme 10:
Synthetic route to Example 51.
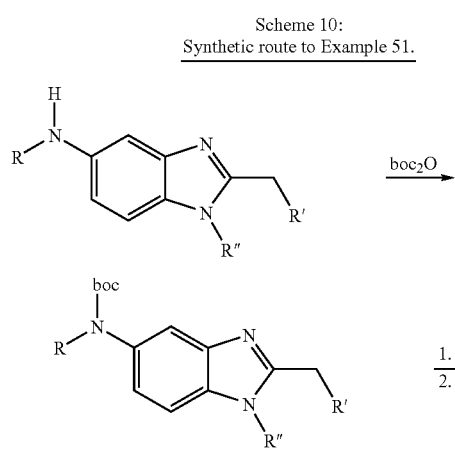
Scheme 11:
Synthetic route to Example 57
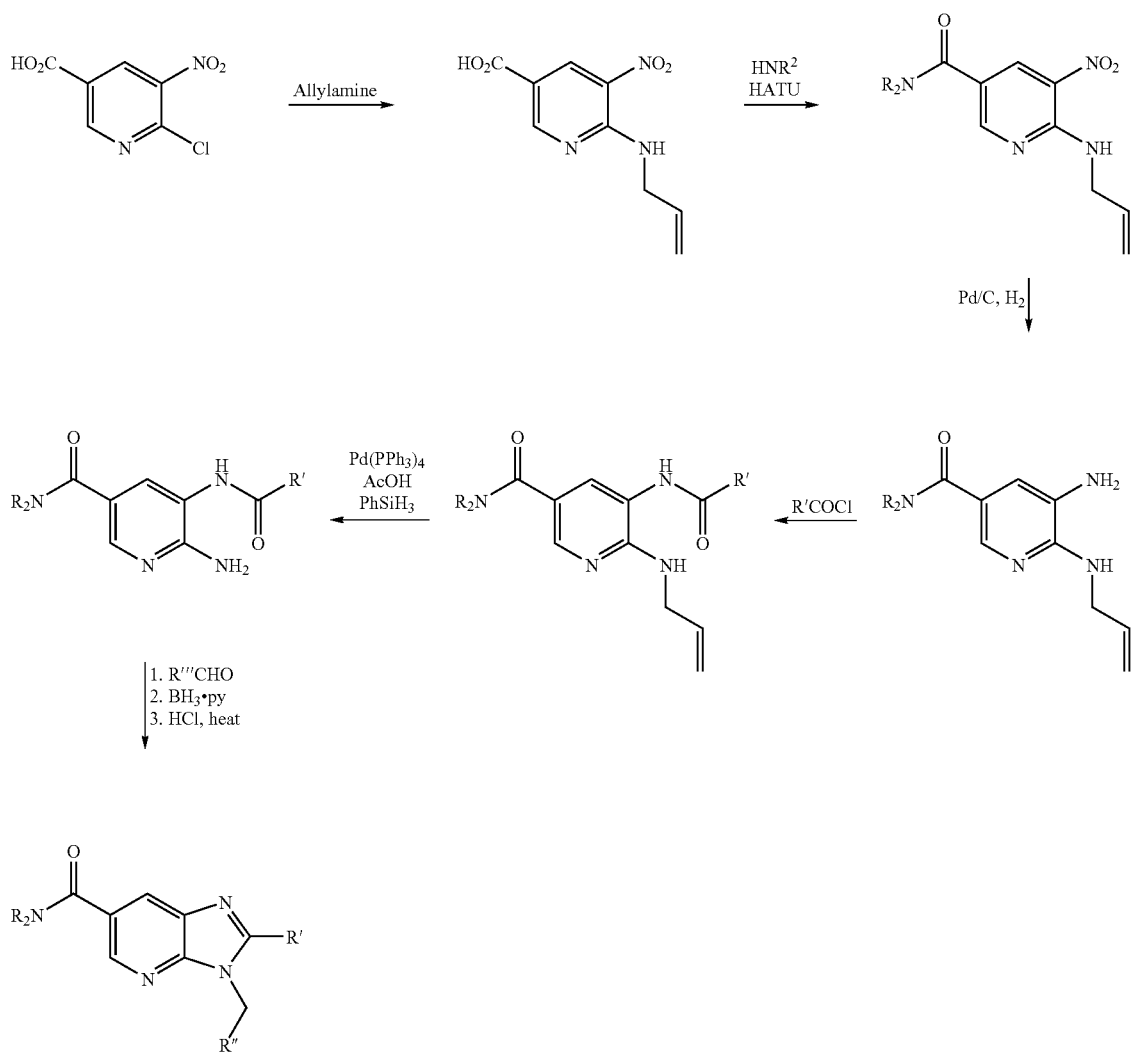

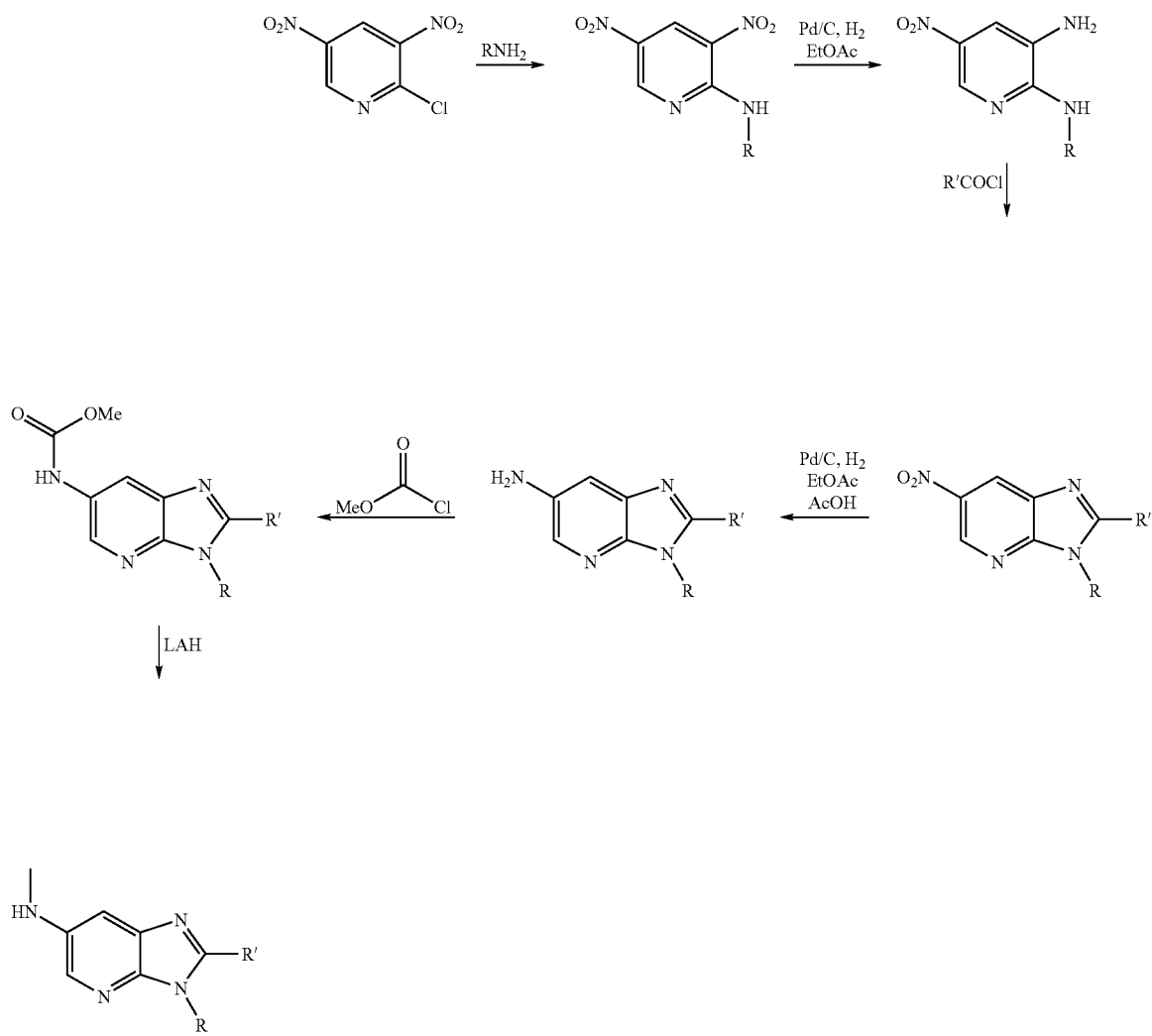
Scheme 12:
Synthetic route to Example 58.
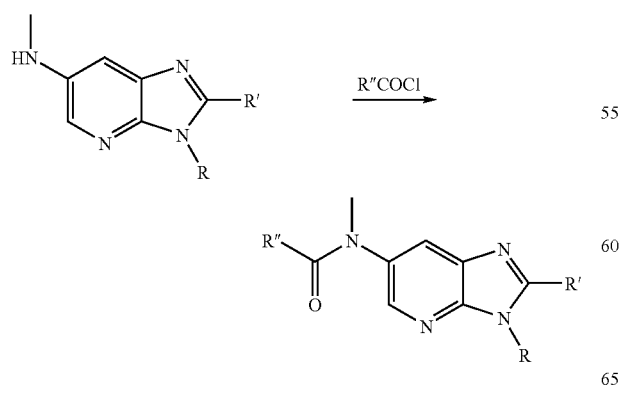
Scheme 13:
Synthetic route to Example 59.
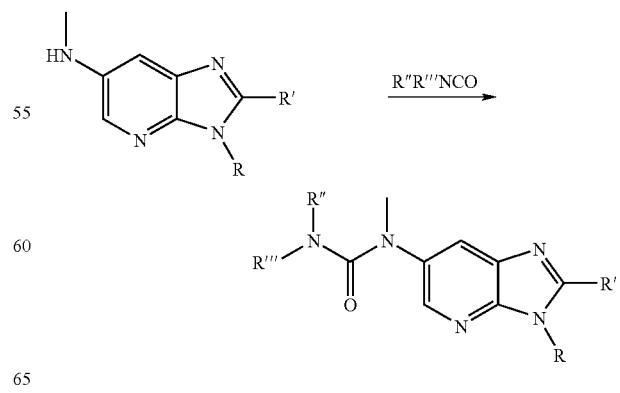
Scheme 14:
Synthetic route to Example 60.

Scheme 15:
Synthetic route to Examples 61 and 62.

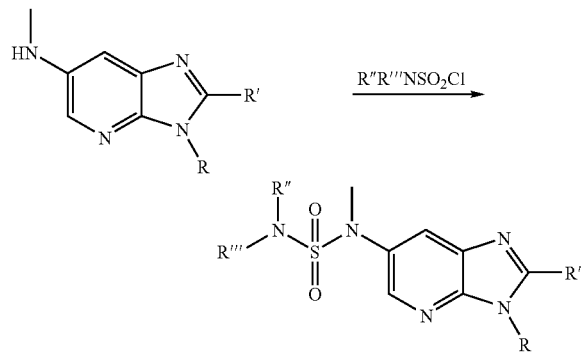

EXAMPLES

The invention will further be described in more detail by the following Examples which describe methods whereby compounds of the present invention may be prepared, purified, analyzed and biologically tested, and which are not to be construed as limiting the invention.

Example 1

Biological Evaluation hCB1 and hCB2 Receptor Binding

Human CB1 (from Receptor Biology) or CB2 (from BioSignal) membranes are thawed at 37° C., passed 3 times through a 25-gauge blunt-end needle, diluted in the cannabinoid binding buffer (50 mM Tris, 2.5 mM EDTA, 5 mM $MgCl_2$, and 0.5 mg/mL BSA fatty acid is free, pH 7.4) and aliquots containing the appropriate amount of protein are distributed in 96-well plates. The $IC_{50}$ of compounds at hCB1 and hCB2 are evaluated from 10-point dose-response curves done with $^3$H-CP55,940 at 20000 to 25000 dpm per well (0.17–0.21 nM) in a final volume of 300 μl. The total and non-specific binding are determined in the absence and presence of 0.2 μM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM $MgCl_2$, 0.5 mg BSA pH 7.0). The filters are dried for 1 hour at 55° C. The radioactivity (cpm) is counted in a TopCount (Packard) after adding 65 μl/well of MS-20 scintillation liquid.

hCB1 and hCB2 GTPγS Binding

Human CB1 (Receptor Biology) or CB2 membranes (BioSignal) are thawed at 37° C., passed 3 times through a 25-gauge blunt-end needle and diluted in the GTPγS binding buffer (50 mM Hepes, 20 mM NaOH, 100 mM NaCl, 1 mM EDTA, 5 mM $MgCl_2$, pH 7.4, 0.1% BSA). The EC50 and Emax of compounds are evaluated from 10-point dose-response curves done in 300 μl with the appropriate amount of membrane protein and 100000–130000 dpm of GTPg$^{35}$S per well (0.11–0.14 nM). The basal and maximal stimulated binding are determined in absence and presence of 1 μM (CB2) or 10 μM (CB1) Win 55,212-2 respectively. The membranes are pre-incubated for 5 minutes with 56.25 μM (CB2) or 112.5 μM (CB1) GDP prior to distribution in plates (15 μM (CB2) or 30 μM (CB1) GDP final). The plates are vortexed and incubated for 60 minutes at room temperature, filtered on Unifilters GF/B (presoaked in water) with the Tomtec or Packard harvester using 3 ml of wash buffer (50 M Tris, 5 nM $MgCl_2$, 50 mM NaCl, pH 7.0). The filters are dried for 1 hour at 55° C.: The radioactivity (cpm) is counted in a TopCount (Packard) after adding 65 μl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist. Biological data for selected compounds is listed in Table 1 below.

TABLE 1

Biological Data for Selected Compounds from Examples 1–39.

| Ex. # | Name | Ki(hCB2) nM | EC50, hCB2; nM (% Emax) |
|---|---|---|---|
| 5 | Methyl 3-[5-[(diethylamino) carbonyl]-2-(4-ethoxybenzyl)-1H-benzimidazol-1-yl]-propanoate | 142 | 65(53%) |
| 7 | 1-{2-[Acetyl(methyl)amino] ethyl}-2-(4-ethoxybenzyl)-N,N-diethyl-1H-benzimidazole-5-carboxamide | 858 | 380(63%) |
| 11 | 1-[2-(Dimethylamino)-1-methylethyl]-2-(4-ethoxy-benzyl)-N,N-diethyl-1H-benzimidazole-5-carboxamide | 751 | 85(64%) |
| 13 | 1-(Cyclopropylmethyl)-2-[(6-ethoxy-3-pyridinyl)methyl]-N,N-diethyl-1H-benzimidazole-5-carboxamide. | 133 | 97(93%) |
| 24 | 1-(Cyclopropylmethyl)-2-(4-ethoxybenzyl)-5-(4-morpholinylmethyl)-1H-benzimidazole | 178 | 81(62%) |
| 26 | Methyl-1-(cyclopropyl-methyl)-2-(4-ethoxybenzyl)-1H-benzimidazol-5-yl carbamate | 430 | 295(41%) |
| 33 | N-Allyl-1-(cyclopropyl-methyl)-2-(4-ethoxybenzyl)-1H-benz-imidazol-5-amine | 308 | 146(54%) |

TABLE 1-continued

Biological Data for Selected Compounds from Examples 1–39.

| Ex. # | Name | Ki(hCB2) nM | EC50, hCB2; nM (% Emax) |
|---|---|---|---|
| 39 | 2-(4-Ethoxyanilino)-N,N-diethyl-1-isopentyl-1H-benzimidazole-5-carboxamide | 98 | 64(64%) |

Example 2

2-(4-Methoxybenzyl)-N,N-diethyl-1-[2-(4-morpholinyl)ethyl]-1H-benzimidazole-5-carboxamide 2A: N,N-diethyl-4-fluoro-3-nitrobenzamide:

A stirred solution of 4-fluoro-3-nitrobenzoic acid (25.0 g, 135 mmol) and thionyl chloride (40.0 mL, 548 mmol) in $CH_2Cl_2$ (40 mL) was refluxed until starting materials were consumed. The solvent was evaporated in vacuo, co-evaporating with toluene (2×20 mL). The acyl chloride thus obtained was dissolved in $CH_2Cl_2$ (60 mL) and cooled to 0° C. before the addition of diisopropylethylamine (DIPEA) (28.2 mL, 162 mmol) and diethylamine (14.0 mL, 135 mmol) under vigorous stirring. After 2 hours at room temperature, the solvent was evaporated in vacuo and the resulting oil was dissolved in $Et_2O$ (200 mL), washed with 5% NaOH (3×100 mL), 5% $KHSO_4$ (100 mL) and brine (100 mL). The organic layer was dried over $MgSO_4$, filtered and evaporated in vacuo. The crude oil was dissolved in EtOAc (10 is mL) and, after overnight (O/N) at −20° C., the bright orange solid was filtered, washed with cold EtOAc (5 mL) and cold hexanes (10 mL) to provide the title compound (19.6 g). The filtrate was evaporated and crystallized similarly in EtOAc (2 mL) to provide another 6.7 g of the title compound (80.5%) as a bright orange solid. $^1$H NMR ($CDCl_3$): δ 8.11 (dd, J=7.6 Hz, J=1.8 Hz, 1H), 7.71–7.67 (m, 1H), 7.36 (dd, J=10.8 Hz, J=8.4 Hz, 1H), 3.56 (br s, 2H), 3.28 (br S, 2H), 1.22 (br s, 6H).

2B: N,N-diethyl-4-{[2-(4-morpholinyl)ethyl]amino}-3-nitrobenzamide.

A mixture of N,N-diethyl-4-fluoro-3-nitrobenzamide (1.00 g, 4.16 mmol), 2-(4-morpholinyl)ethanamine (0.600 mL, 4.58 mmol) in 80% aq. EtOH (50 mL) was refluxed for 4 hours. The reaction was then concentrated in vacuo, and the residue was taken up into EtOAc (40 mL). The organic phase was washed with saturated $NaHCO_3$ (2×10 mL), and the combined aqueous phases were extracted with additional EtOAc (2×20 mL). The combined organic phases were dried over $MgSO_4$, filtered, and concentrated in vacuo to provide the title compound. The crude product was purified by silica gel column chromatography (100% EtOAc to 5% triethylamine/EtOAc) to provide the title compound (1.12 g, 77%) as a bright yellow solid. $^1$H-NMR ($CDCl_3$): δ 8.67 (s, 1H), 8.28 (d, J=1.2 Hz, 1H), 7.56 (dd, J=8.8 Hz, J=1.6 Hz, 1H), 6.85 (d, J=8.8 Hz, 1H), 3.77 (t, J=5.2 Hz, 4H), 3.55–3.20 (br m, 6H), 2.74 (t, J=6.4 Hz, 2H), 2.53 (br s, 4H), 1.22 (t, J=6.8 Hz, 6H). MS (ESI) (M+H)$^+$=351.

2C: 3-amino-N,N-diethyl-4-{[2-(4-morpholinyl)ethyl]amino}benzamide.

A mixture of N,N-diethyl-4-{[2-(4-morpholinyl)ethyl]amino}-3-nitrobenzamide (1.10 g, 3.14 mmol) and 10% Pd/C in MeOH (50 mL) was hydrogenated for 2 hours at 40 psi. After the reaction was complete, the reaction mixture was filtered through diatomaceous earth. Removal of solvent provided the title compound (0.958 g, 95%) which was used without further purification. MS (ESI) (M+H)$^+$=321.

2D: 2-(4-Methoxybenzyl)-N,N-diethyl-1-[2-(4-morpholinyl)ethyl]-1H-benzimidazole-5-carboxamide.

(4-methoxyphenyl)acetyl chloride (0.063 g, 0.343 mmol) was added to 3-amino-N,N-diethyl-4-{[2-(4-morpholinyl)ethyl]amino}benzamide (0.100 g, 0.312 mmol) in acetic acid (2 mL) and the mixture was stirred at 95° C. overnight. The reaction was then concentrated in vacuo, and the residue was taken up into EtOAc (15 mL). The organic phase was washed with 1 N NaOH (2×8 mL) and the combined aqueous phases were extracted with additional EtOAc (2×15 mL). The combined organic phases were dried over $MgSO_4$, filtered, and concentrated in vacuo. The crude product was purified by reverse-phase high pressure liquid chromatography (HPLC) to provide the title compound as a trifluoroacetic acid (TFA) salt (0.132 g, 53%). $^1$H NMR (DMSO-$d_6$): δ 7.74 (d, J=8.0 Hz, 1H), 7.57 (s, 1H), 7.34 (d, J=8.0 Hz, 1H), 7.25 (d, J=8.0 Hz, 2H), 6.91 (d, J=8.0 Hz, 2H), 4.64 (t, J=7.6 Hz 2H), 4.36 (s, 2H) 3.76 (br s, 2H), 3.71 (s, 3H), 3.35 (br s, 4H), 3.20 (br s, 6H), 1.07 (br s, 6H). MS (ESI) (M+H)$^+$=451. Anal. Calcd for $C_{26}H_{34}N_4O_3$+3.0 TFA+0.6$H_2O$: C, 47.84; H, 4.79; N, 6.97. Found: C, 47.83; H, 4.83; N, 6.96.

Example 3

2-(4-Ethoxybenzyl)-N,N-diethyl-1-(2-methoxyethyl)-1H-benzimidazole-5-carboxamide.

3A: N,N-diethyl-4-[(2-methoxyethyl)amino]-3-nitrobenzamide.

Following general procedure 2B: A mixture of N,N-diethyl-4-fluoro-3-nitrobenzamide (0.200 g, 0.833 mmol), 2-methoxyethanamine (0.065 mL, 0.757 mmol) in 80% aq. EtOH (5 mL) was heated at 90° C. overnight: After work-up, the crude product was purified by silica gel column chromatography (33% EtOAc/Hexanes to 50% EtOAc/Hexanes) to provide the title compound (0.191 g, 85%) as a bright yellow solid. $^1$H-NMR ($CDCl_3$): δ 8.34 (s, 1H), 8.28 (d, J=2.8 Hz, 1H), 7.56 (dd, J=8.4 Hz, J=1.6 Hz, 1H), 6.91 (d, J=9.2 Hz, 1H), 3.69 (t, J=5.6 Hz, 2H), 3.53 (q, J=5.6 Hz, 2H), 3.44 (s overlapping with br s, 7H), 1.22 (t, J=6.4 Hz, 6H). MS (ESI) (M+H)$^+$=296

3B: 3-amino-N,N-diethyl-4-[(2-methoxyethyl)amino].

Following general procedure 2C: A mixture of N,N-diethyl-4-[(2-methoxyethyl)amino]-3-nitrobenzamide (0.150 g, 0.508 mmol) and 10% Pd/C in EtOAc (15 mL) was hydrogenated overnight at 40 psi. Usual work-up provided the title compound (0.159 g) which was used without further purification. $^1$H-NMR ($CDCl_3$): δ 6.86 (dd, J=8.4 Hz, J=2.0 Hz, 1H), 6.80 (d, J=1.6 Hz, 1H), 6.60 (d, J=8.0 Hz, 1H), 3.66

(t, J=5.6 Hz, 2H), 3.41 (s overlapping with br s, 7H), 3.31 (t, J=5.6 Hz, 2H), 1.18 (t, J=7.6 Hz, 6H). MS (ESI) (M+H)$^+$ =266.

3C: (4-ethoxyphenyl)acetyl chloride.

To a stirred solution of (4-ethoxyphenyl)acetic acid (10.0 g, 55.5 mmol) in benzene (100 mL) was added thionyl chloride (50 mL, 68.5 mmol) and the reaction mixture was stirred at 80° C. for 2 hours. The solvent was evaporated in vacuo and the crude product was purified by distillation (bp 86° C., 0.4 Torr) to provide the title compound (10.39 g, 94%) as a yellow oil. MS of methyl ester: MS (ESI) (M+H)$^+$=194.

3D: 2-(4-Ethoxybenzyl)-N,N-diethyl-1-(2-methoxyethyl)-1H-benzimidazole-5-carboxamide Following general procedure 2D: (4-ethoxyphenyl)acetyl chloride (0.107 g, 0.539 mmol) was added to 3-amino-N,N-diethyl-4-[(2-methoxyethyl)amino]benzamide (0.130 g, 0.490 mmol) in toluene (2.5 mL). After 20 minutes, one drop of conc. HCl was added and the mixture was heated at 85° C. for 12 hours. After usual work-up, the crude product was purified by reverse-phase HPLC to provide the title compound as a TFA salt (0.120 g, 36%) as an oil. $^1$H NMR (DMSO-d$_6$): δ 7.86 (d, J=9.2 Hz, 1H), 7.63 (s, 1), 7.43 (d, J=8.4 Hz, 1H), 7.25 (d, J=8.4 Hz, 2H), 6.90 (d, J=9.2 Hz, 2H), 4.60 (t, J=4.8 Hz, 2H), 4.47 (s, 2H), 3.97 (q, J=7.6 Hz, 2H), 3.57 (m, 2H), 3.40 (br s, 2H), 3.20 (br s, 2H), 3.15 (s, 3H), 1.28 (t, J=7.6 Hz, 3H), 1.07 (br s, 6H). MS (ESI) (M+H)$^+$=411. Anal. Calcd for C$_{24}$H$_{31}$N$_3$O$_3$+2.2 TFA+ 0.6H$_2$O: C, 50.82; H, 5.17; N, 6.26. Found: C, 50.85; H, 5.30; N, 6.06.

Example 4

1-[2-(Acetylamino)ethyl]-2-(4-ethoxybenzyl)-N,N-diethyl-1H-benzimidazole-5-carboxamide 4A: 4-{[2-(acetylamino)ethyl]amino}-N,N-diethyl-3-nitrobenzamide.

Following general procedure 2B: A mixture of N,N-diethyl-4-fluoro-3-nitrobenzamide (0.200 g, 0.833 mmol), N-(2-aminoethyl)acetamide (0.077 g, 0.757 mmol) in 80% aq. EtOH (5 mL) was heated at 90° C. overnight. After work-up, the crude product was purified by silica gel column chromatography (100% EtOAc to 5% MeOH/EtOAc) to provide the title compound (0.152 g, 63%) as a bright yellow solid. $^1$H-NMR (CDCl$_3$): δ 8.27 (d overlapping with br s, J=2.0 Hz, 2H), 7.55 (dd, J=8.4 Hz, J=2.0 Hz, 1H), 6.99 (d, J=9.2 Hz, 1H), 6.06 (br s, 1H), 3.58–3.50 (m, 4H), 3.44 (br s, 4H), 2.02 (s, 3H), 1.22 (t, J=7.2 Hz, 6H). MS (ESI) (M+H)$^+$=323.

4B: 4-{[2-(acetylamino)ethyl]amino}-3-amino-N,N-diethylbenzamide.

Following general procedure 2C: A mixture of 4-{[2-(acetylamino)ethyl]amino}-N,N-diethyl-3-nitrobenzamide (0.150 g, 0.465 mmol) and 10% Pd/C in EtOAc (15 mL) was hydrogenated overnight at 40 psi. Usual work-up provided the title compound (0.164 g, 100%) which was used without further purification. $^1$H-NMR (CDCl$_3$): δ 6.83 (dd, J=8.0 Hz, J=2.0 Hz, 1H), 6.76 (d, J=2.0 Hz, 1H), 6.53 (d, J=8.4 Hz, 1H), 6.26 (br t, 1H), 3.53 (q, J=5.6 Hz, 2H), 3.43 (br s, 4H), 3.23 (t, J=5.6 Hz, 2H), 1.99 (s, 3H), 1.17 (t, J=6.4 Hz, 6H). MS (ESI) (M+H)$^+$=293.

4C: 1-[2-(Acetylamino)ethyl]-2-(4-ethoxybenzyl)-N,N-diethyl-1H-benzimidazole-5-carboxamide.

Following general procedure 2D: (4-ethoxyphenyl)acetyl chloride (0.097 g, 0.490 mmol) was added to 4-{[2-(acetylamino)ethyl]amino}-3-amino-N,N-diethylbenzamide (0.130 g, 0.445 mmol) in toluene (2.5 mL). After 20 minutes, one drop of HCl conc. was added and the mixture was heated at 85° C. for 12 hours. After usual work-up, the crude product was purified by reverse-phase HPLC to provide the title compound as a TFA salt (0.042 g, 14%) as a tan solid. $^1$H NMR (DMSO-d$_6$): δ 8.01 (t, J=5.6 Hz, 1H), 7.81 (d, J=8.4 Hz, 1H), 7.63 (s, 1), 7.45 (d, J=8.4 Hz, 1H), 7.26 (d, J=8.4 Hz, 2H), 6.90 (d, J=8.4 Hz, 2H), 4.43 (m, 4H), 3.97 (q, J=7.2 Hz, 2H), 3.40 (br s, 2H), 3.38 (t, J=4.8 Hz, 2H), 3.20 (br s, 2H), 3.15 (s, 3H), 1.61 (s, 3H), 1.28 (t, J=7.2 Hz, 3H), 1.06 (br s, 6H). MS (ESI) (M+H)$^+$437. Anal. Calcd for C$_{25}$H$_{32}$N$_4$O$_3$+2.1 TFA+0.8H$_2$O: C, 50.80; H, 5.21; N, 8.11. Found: C, 50.87; H, 5.87; N, 8.09.

Example 5

Methyl 3-[5-[(diethylamino)carbonyl]-2-(4-ethoxybenzyl)-1H-benzimidazol-1-yl]propanoate 5A: Ethyl 3-{4-[(diethylamino)carbonyl]-2-nitroanilino}propanoate.

Following general procedure 2B: A mixture of N,N-diethyl-4-fluoro-3-nitrobenzamide (0.200 g, 0.833 mmol), ethyl 3-aminopropanoate (0.116 g, 0.757 mmol) in 80% aq. EtOH (5 mL) was heated at 90° C. overnight. After work-up, the crude product was purified by silica gel column chromatography (50% EtOAc/Hexanes to 100% EtOAc) to provide the title compound (0.162 g, 63%). $^1$H-NMR (CDCl$_3$): δ 8.34 (br t, J=5.6 Hz, 1H), 8.29 (d, J=2.0 Hz, 1H), 7.58 (dd, J=8.4 Hz, J=2.0 Hz, 1H), 6.92 (d, J=9.2 Hz, 1H), 4.21 (q, J=7.2 Hz, 2H), 3.69 (q, J=6.4 Hz, 2H), 3.44 (br s, 4H), 2.72 (t, J=6.4 Hz, 2H), 1.30 (t, J=6.4 Hz, 3H), 1.22 (t, J=6.8 Hz, 6H). MS (ESI) (M+H)$^+$=338.

5B: Ethyl 3-{2-amino-4-[(diethylamino)carbonyl]anilino}propanoate.

Following general procedure 2C: A mixture of ethyl 3-{4-[(diethylamino)carbonyl]-2-nitroanilino}propanoate (0.150 g, 0.445 mmol) and 10% Pd/C in EtOAc (15 mL) was hydrogenated overnight at 40 psi. Usual work-up provided the title compound (0.158 g) which was used without further purification. $^1$H-NMR (CDCl$_3$): δ 6.86 (dd, J=8.4 Hz, J=2.0 Hz, 1H), 6.80 (d, J=2.0 Hz, 1H), 6.62 (d, J=8.4 Hz, 1H), 4.18 (q, J=7.2 Hz, 2H), 3.46 (t and overlapping br s, J=5.6 Hz, 6H), 2.66 (t, J=6.8 Hz, 2H), 1.28 (t, J=7.2 Hz, 3H), 1.18 (t, J=6.8 Hz, 6H). MS (ESI) (M+H)$^+$=308.

5C: Methyl 3-[5-[(diethylamino)carbonyl]-2-(4-ethoxybenzyl)-1H-benzimidazol-1-yl]propanoate.

Following general procedure 2D: (4-ethoxyphenyl)acetyl chloride (0.092 g, 0.465 mmol) was added to ethyl 3-{2-amino-4-[(diethylamino)carbonyl]anilino}propanoate (0.130 g, 0.423 mmol) in toluene (2.5 mL). After 20 minutes, one drop of HCl conc. was added and the mixture was heated at 85° C. for 12 hours. After work-up, the crude product was purified by reverse-phase HPLC (which was accompanied by trans-esterification with MeOH) to provide the title compound as a TFA salt (0.084 g, 30%) as an oil. $^1$H NMR (DMSO-d$_6$): δ 7.88 (d, J=9.2 Hz, 1H), 7.62 (s, 1H), 7.41 (d, J=8.4 Hz, 1H), 7.25 (d, J=8.0 Hz, 2H), 6.90 (d, J=8.4 Hz, 2H), 4.59 (t, J=6.4 Hz, 2H), 4.49 (s, 2H), 3.97 (q, J=6.4 Hz, 2H), 3.55 (s, 3H), 3.40 (br s, 2H), 3.16 (br s, 2H), 2.77 (t, J=6.4 Hz, 2H), 1.28 (t, J=7.6 Hz, 3H), 1.07 (br s, 6H). MS (ESI) (M+H)$^+$=438. Anal. Calcd for $C_{25}H_{31}N_3O_4$+1.8 TFA+ 0.8H$_2$O: C, 52.27; H, 5.28; N, 6.39. Found: C, 52.31; H, 5.22; N, 6.37.

Example 6

1-(2-Aminoethyl)-2-(4-ethoxybenzyl)-N,N-diethyl-1H-benzimidazole-5-carboxamide 6A: tert-Butyl 2-{4-[(diethylamino)carbonyl]-2-nitroanilino} ethylcarbamate.

Following general procedure 2B: A mixture of N,N-diethyl-4-fluoro-3-nitrobenzamide (0.200 g, 0.833 mmol), tert-butyl 2-aminoethylcarbamate (0.121 g, 0.757 mmol) in 80% aq. EtOH (3 mL) was heated at 85° C. overnight. After work-up, the crude product was purified by recrystallization from EtOAc to provide the title compound (0.165 g, 57%) as a bright yellow solid. $^1$H-NMR (CDCl$_3$): δ 8.31 (br s, 1H), 8.29 (d, J=1.6 Hz, 1H), 7.57 (dd, J=9.6 Hz, J=2.0 Hz, 1H), 6.97 (d, J=9.6 Hz, 1H), 4.83 (br s, 1H), 3.55–3.40 (m, 8H), 1.47 (s, 9H), 1.22 (t, J=7.6 Hz, 6H). MS (ESI) (M+H)$^+$=381.

6B: tert-butyl 2-{2-amino-4-[(diethylamino)carbonyl] anilino}ethylcarbamate.

Following general procedure 2C: A mixture of tert-butyl 2-{4-[(diethylamino)carbonyl]-2-nitroanllino}ethylcarbamate (0.155 g, 0.407 mmol) and 10% Pd/C in EtOAc (15 mL) was hydrogenated overnight at 40 psi. Usual work-up provided the title compound (0.164 g) which was used without further purification. $^1$H-NMR (CDCl$_3$): δ 6.85 (dd, J=8.4 Hz, J=1.6 Hz, 1H), 6.80 (d, J=2.0 Hz, 1H), 6.57 (d, J=7.6 Hz, 1H), 4.87 (br s, 1H), 3.48–3.38 (br s, 6H), 3.27 (t, J=5.6 Hz, 2H), 1.46 (s, 9H), 1.18 (t, J=6.8 Hz, 6H). MS (ESI) (M+H)$^+$=351.

6C: 1-(2-Aminoethyl)-2-(4-ethoxybenzyl)-N,N-diethyl-1H-benzimidazole-5-carboxamide.

Following general procedure 2D: (4-ethoxyphenyl)acetyl chloride (0.085 g, 0.424 mmol) was added to tert-butyl 2-{2-amino-4-[(diethylamino)carbonyl] anilino}ethylcarbamate (0.135 g, 0.385 mmol) in toluene (2.5 mL). After 20 minutes, one drop of HCl conc. was added and the mixture was heated at 85° C. for 12 hours. After work-up, the crude product was purified by reverse-phase HPLC to provide the title compound as a TFA salt (0.123 g, 44%) as a white solid. $^1$H NMR (CD$_3$OD): δ 7.91 (d, J=8.4 Hz, 1H), 7.73 (s, 1H), 7.57 (dd, J=8.4 Hz, J=2.0 Hz, 2H), 7.30 (d, J=8.4 Hz, 2H), 6.97 (d, J=8.4 Hz, 2H), 4.75 (t, J=6.8 Hz, 2H), 4.55 (s, 2H), 4.03 (q, J=6.8 Hz, 2H), 3.58 (br s, 2H), 3.36 (t, J=6.4 Hz, 2H), 3.29 (br s, 2H), 1.37 (t, J=6.4 Hz, 3H), 1.27 (br s, 3H), 1.12 (br s, 3H). MS (ESI) (M+H)$^+$=395. Anal. Calcd for $C_{23}H_{30}N_4O_2$+2.8 TFA+ 0.8H$_2$O: C, 47.17; H, 4.76; N, 7.69. Found: C, 47.16; H, is 4.80; N, 7.52.

Example 7

1-{2-[Acetyl(methyl)amino]ethyl}-2-(4-ethoxybenzyl)-N,N-diethyl-1H-benzimidazole-5 carboxamide To a solution of the product 6C, the TFA salt of 1-(2-aminoethyl)-2-(4-ethoxybenzyl)-N,N-diethyl-1H-benzimidazole-5-Carboxamide (0.085 g, 0.117 mmol), triethylamine (0.070 mL, 0.50 mmol) in CH$_2$Cl$_2$ (3 mL) was added acetyl chloride (0.015 g, 0.200 mmol) and the resulting mixture was stirred at room temperature for 15 minutes. The mixture was washed with saturated aqueous NaHCO$_3$, brine and the organic phase was dried over MgSO$_4$, filtered, and concentrated in vacuo.

The above crude product was dissolved in dimethylformamide (DMF) (2 mL), NaH (60% dispersion in oil, 0.005 g, 0.217 mmol) was added and the mixture was stirred at room temperature for 20 minutes. The solvent was evaporated in vacuo and the residue was taken up into EtOAc. The organic phase was washed with saturated aqueous NaHCO$_3$, brine, dried over MgSO$_4$, filtered, and concentrated in vacuo. The crude product was purified by reverse-phase HPLC to provide the title compound as a TFA salt (0.017 g, 26%) as a white solid. $^1$H NMR (CD$_3$OD): δ 7.97 (d, J=8.4 Hz, 1H), 7.69 (s, 1H), 7.59 (d, J=7.2 Hz, 1H), 7.33 (d, J=8.4 Hz, 2H), 6.96 (d, J=8.4 Hz, 2H), 4.66 (t, J=6.0 Hz, 2H), 4.60 (s, 2H), 4.02 (q, J=7.1 Hz, 2H), 3.72 (t, J=6.0 Hz, 2H), 3.56 (br, 2H), 3.28 (br, 4H), 3.06 (s, 3H), 1.79 (s, 3H), 1.36 (t, J=8.6 Hz, 3H), 1.25 (br, 3H), 1.10 (br, 3H). MS (ESI) (M+H)$^+$=451.

Example 8

2-(4-Ethoxybenzyl)-N,N-diethyl-1-methyl-1H-benzimidazole-5-carboxamide

8A: N,N-diethyl-4-(methylamino)-3-nitrobenzamide.

Following general procedure 2B: A mixture of N,N-diethyl-4-fluoro-3-nitrobenzamide (0.125 g, 0.521 mmol), methylamine hydrochloride (0.035 g, 0.521 mmol) in 80% aq. EtOH (3 mL) was heated at 85° C. for 4 hours. Usual work-up provided the title compound (0.130 g, 100%) which was used without further purification. MS (ESI) (M+H)$^+$=252.

8B: 3-amino-N,N-diethyl-4-(methylamino)benzamide.

Following general procedure 2C: A mixture of N,N-diethyl-4-(methylamino)-3-nitrobenzamide (0.130 g, 0.517 mmol) and 10% Pd/C in EtOAc (10 mL) was hydrogenated at 40 psi. Usual work-up provided the title compound (0.124 g) which was used without further purification. MS (ESI) (M+H)$^+$=222.

8C: 2-(4-Ethoxybenzyl)-N,N-diethyl 1-methyl-1H-benzimidazole-5-Carboxamide.

Following general procedure 2D: (4-ethoxyphenyl)acetyl chloride (0.119 g, 0.596 mmol) was added to 3-amino-N,N-diethyl-4-(methylamino)benzamide (0.120 g, 0.542 mmol) in acetic acid (2 mL) and the mixture was stirred at 90° C. overnight. After work-up, the crude product was purified by reverse-phase HPLC to provide the title compound as a TFA salt (0.087 g, 26%) as a red oil. $^1$H-NMR (DMSO-d$_6$): δ 7.90 (d, J=8.4 Hz, 1H), 7.70 (s, 1H), 7.49 (d, J=8.4 Hz, 1H), 7.29 (d, J=8.4 Hz, 2H), 6.92 (d, J=8.4 Hz, 2H), 4.50 (s, 2H), 3.98 (q, J=7.6 Hz, 2H), 3.93 (s, 3H), 3.42 (brs, 2H), 3.14 (br s, 2H), 1.28 (t, J=6.8 Hz, 3H), 1.11 (br s, 3H), 1.04 (br s, 3H). MS (ESI) (M+H)$^+$=366. Anal. Calcd for $C_{22}H_{27}N_3O_2$+2.1 TFA+0.2H$_2$O: C, 51.71; H, 4.89; N, 6.91. Found: C, 51.73; H, 4.82; N, 6.93.

Example 9

2-(4-Ethoxybenzyl)-N,N-diethyl-1-(2-phenylethyl)-1H-benzimidazole-5-carboxamide

9A: N,N-diethyl-3-nitro-4[(2-phenylethyl)amino]benzamide.

Following general procedure 2B: A mixture of N,N-diethyl-4-fluoro-3-nitrobenzamide (0.125 g, 0.521 mmol), 2-phenylethanamine (0.065 mL, 0.521 mmol) in 80% aq. EtOH (3 mL) was heated at 85° C. for 4 hours. Usual work-up provided the title compound (0.170 g, 96%) which was used without further purification. MS (ESI) (M+H)$^+$ =342.

9B: 3-amino-N,N-diethyl-4-[(2-phenylethyl)amino]benzamide.

Following general procedure 2C: A mixture of N,N-diethyl-3-nitro-4[(2-phenylethyl)amino]benzamide (0.170 g, 0.498 mmol) and 10% Pd/C in EtOAc (10 mL) was hydrogenated at 40 psi. Usual work-up provided the title compound (0.156 g) which was used without further purification. MS (ESI) (M+H)$^+$=312.

9C: 2-(4-Ethoxybenzyl)-N,N-diethyl-1-(2-phenylethyl)-1H-benzimidazole-5-carboxamide Following general procedure 2E: (4-ethoxyphenyl)acetyl chloride (0.105 g, 0.530 mmol) was added to 3-amino-N,N-diethyl-4-[(2-phenylethyl)amino]benzamide (0.150 g, 0.482 mmol) in acetic acid (2 mL) and the mixture was stirred at 90° C. overnight. After work-up, the crude product was purified by reverse-phase HPLC to provide the title compound as a TFA salt (0.100 g, 36%) as a purple solid. $^1$H-NMR (DMSO-4): δ 7.74 (d, J=8.4 Hz, 1H), 7.62 (s, 1H), 7.34 (d, J=7.2 Hz, 1H), 7.24–7.19 (m, 5H), 7.10 (d, J=8.4 Hz, 2H), 6.91 (d, J=8.4 Hz, 2H), 4.56 (t, J=7.2 Hz, 2H), 4.23 (s, 2H), 3.97 (q, J=6.8 Hz, 2H), 3.40 (br s, 2H), 3.19 (br s, 2H), 2.86 (t, J=7.2 Hz, 2H), 1.28 (t, J=6.8 Hz, 3H), 1.08 (br s, 6H). MS (ESI) M+H)$^+$=456. Anal. Calcd for C$_{29}$H$_{33}$N$_3$O$_2$+1.0 TFA+0.2H$_2$O: C, 64.96; H, 6.05; N, 7.33. Found: C, 65.05; H, 6.09; N, 7.29.

Example 10

2-(4-Ethoxybenzyl)-N,N-diethyl-1-[2-(1-piperidinyl)ethyl]-1H-benzimidazole-5-carboxamide 10A: N,N-diethyl-3-nitro-4-{[2-(1-piperidinyl)ethyl]amino}benzamide.

Following general procedure 2B: A mixture of N,N-diethyl-4-fluoro-3-nitrobenzamide (1.0 g, 4.2 mmol), 2-(1-piperidinyl)ethanamine (0.564 mL, 3.96 mmol) in 80% aq. EtOH (30 mL) was heated at 85° C. for 10 hours. After the usual work-up, the crude mixture was dissolved in 1 N HCl (40 mL) and washed with CH$_2$Cl$_2$ (2×10 mL). The aqueous layer was basified with 5 N NaOH (10 mL) and extracted with CH$_2$Cl$_2$ (3×10 mL). The combined organic phases were dried over Na$_2$SO$_4$, filtered and concentrated in vacuo to provide the title compound (0.800 g, 57%) as a bright yellow solid which was used without further purification. $^1$H-NMR (CDCl$_3$): δ 8.64 (br s, 1H), 8.25 (d, J=2.4 Hz, 1H), 7.53 (d, J=8.8 Hz, 1H), 6.82 (d, J=8.8 Hz, 1H), 3.41 (br s, 4H), 3.35 (br s, 2H), 2.64 (br s, 2H), 2.53 (br s, 4H), 1.61 (br s, 4H), 1.44 (br s, 2H), 1.19 (t, J=7.0 Hz, 6H).

10B: 3-amino-N,N-diethyl-4-{[2-(1-piperidinyl)ethyl]amino}benzamide.

Following general procedure 2C: A mixture of N,N-diethyl-3-nitro-4-{[2-(1-piperidinyl)ethyl]amino}benzamide (0.800 g, 2.30 mmol) and 10% Pd/C in EtOAc (30 mL) was hydrogenated for 24 hours at 30 psi. Usual work-up provided the title compound (0.724 g, 99%) which was used without further purification.

10C: 2-(4-Ethoxybenzyl)-N,N-diethyl-1-[2-(1-piperidinyl)ethyl]-1H-benzimidazole-5-carboxamide.

Following general procedure 2D: A solution of 1 M (4-ethoxyphenyl)acetyl chloride in toluene (0.095 mL, 0.095 mmol) was added to 3-amino-N,N-diethyl-4-{[2-(1-piperidinyl)ethyl]amino}benzamide (0.027 g, 0.856 mmol) in toluene (1.0 mL). After 20 minutes, one drop of HCl conc. was added and the mixture was heated at 85° C. overnight. After work-up, the crude product was purified by reverse-phase HPLC to provide the title compound as a TFA salt (0.026 g, 39%). $^1$H-NMR (CD$_3$OD): δ 7.89 (d, J=8.0 Hz, 1H), 7.70 (s, 1H), 7.52 (d, J=8.4 Hz, 1H), 7.27 (d, J=7.6 Hz, 2H), 6.96 (d, J=7.2 Hz, 2H), 4.52 (s, 2H), 4.02 (q, J=7.6 Hz, 2H), 3.56 (br s, 4H), 3.34 (t, J=7.6 Hz, 2H), 3.28 (br s, 4H), 3.00 (br s, 2H), 1.88 (br s, 4H), 1.53 (br s, 2H), 1.36 (t, J=6.4 Hz, 3H), 1.25 (br s, 3H), 1.11 (br s, 3H). MS (ESI) (M+H)$^+$=463. Anal. Calcd for C$_{28}$H$_{38}$N$_4$O$_2$+2.6 TFA+0.5H$_2$O: C, 51.92; H, 5.46; N, 7.29. Found: C, 51.94; H, 5.43; N, 7.25.

Example 11

1-[2-(Dimethylamino)-1-methylethyl]-2-(4-ethoxybenzyl)-N,N-diethyl-1H-benzimidazole-5-carboxamide 11A: 4-{[2-(dimethylamino)-1-methylethyl]amino}-N,N-diethyl-3-nitrobenzamide.

A mixture of N,N-diethyl-4-fluoro-3-nitrobenzamide (0.500 g, 2.08 mmol), N$^1$,N$^1$-dimethyl-1,2-propanediamine (0.636 g, 6.24 mmol), DIPEA (2.2 mL, 12.5 mmol) and DMF (12 mL) was stirred 4 hours at room temperature. The reaction was then concentrated in vacuo, the residue was dissolved in 2 N NaOH (30 mL) and extracted with CH$_2$Cl$_2$ (3×40 mL). The combined organic phases were washed with brine (10 mL) dried over MgSO$_4$, filtered, and concentrated in vacuo. The crude reaction mixture was purified by silica gel column chromatography (100% CH$_2$Cl$_2$ to 5% MeOH/CH$_2$Cl$_2$) to provide the title compound (0.621 g, 93%) as a bright yellow solid. $^1$H-NMR (CDCl$_3$): δ 8.33 (d, J=6.4 Hz, 1H), 8.27 (d, J=2.0 Hz, 1H), 7.55 (dd, J=8.8 Hz, J=2.0 Hz, 1H), 6.91 (d, J=9.6 Hz, 1H), 3.79 (heptet, J=7.2 Hz, 1H), 3.45 (br d, J=5.2 Hz, 4H), 2.55 (dd, J=12.0 Hz, J=7.6 Hz, 1H), 2.39 (dd, J=12.4 Hz, J=5.8 Hz, 1H), 2.29 (s, 6H), 1.69 (br s, 1H), 1.31 (d, J=6.8 Hz, 2H), 1.22 (t, J=7.4 Hz, 6H). MS (ESI) (M+H)$^+$=323.

11B: 3-amino-4-{[2-(dimethylamino)-1-methylethyl]amino}-N,N-diethylbenzamide.

Following general procedure 2C: A mixture of 4-{[2-(dimethylamino)-1-methylethyl]amino}-N,N-diethyl-3-nitrobenzamide (0.516 g, 1.60 mmol) and 10% Pd/C in EtOAc (20 mL) was hydrogenated overnight at 35 psi. Usual work-up provided the title compound (0.408 g, 87%) which was used without further purification. $^1$H-NMR (CDCl$_3$): δ 6.82 (dd, J=8.0 Hz, J=2.0 Hz, 1H), 6.77 (d, J=2.4 Hz, 1H), 6.62 (d, J=8.0 Hz, 1H), 3.52–336 (m, 6H), 2.52 (dd, J=12.0 Hz, J=9.6 Hz, 2H), 2.28–2.19 (m, 7H), 1.17 (m, 8H). MS (ESI) (M+H)$^+$=293.

11C: 1-[2-(Dimethylamino)-1-methylethyl]-2-(4-ethoxybenzyl)-N,N-diethyl-1H-benzimidazole-5-carboxamide.

Following general procedure 2D: A solution of 1 M (4-ethoxyphenyl)acetyl chloride in toluene (0.095 mL, 0.095 mmol) was added to 3-amino-4-{[2-(dimethylamino)-1-methylethyl]amino}-N,N-diethylbenzamide (0.025 g, 0.0856 mmol) in toluene (1.0 mL). After 20 minutes, one drop of conc. HCl was added and the mixture was heated at 85° C. overnight. After work-up, the crude product was purified by reverse-phase HPLC to provide the title compound as a TFA salt (0.024 g, 38%). $^1$H-NMR (CD$_3$OD): δ 7.96 (d, J=8.4 Hz, 1H), 7.72 (s, 1H), 7.47 (d, J=7.6 Hz, 2H), 7.24 (m, 2H), 6.94 (m, 2H), 5.20 (br s, 1H), 4.50 (s, 2H), 4.03–3.95 (m, 3H), 3.77 (dd, J=14.0 Hz, J=5.6 Hz, 1H), 3.56 (br s, 2H), 3.28 (m, 2H), 2.81 (s, 6H), 1.56 (d, J=6.8 Hz, 3H), 1.35 (t, J=6.4 Hz, 3H), 1.25 (br s, 3H), 1.14 (br s, 3H). MS (ESI) (M+H)$^+$=437. Anal. Calcd for C$_{26}$H$_{36}$N$_4$O$_2$+2.5 TFA+0.7H$_2$O: C, 50.71; H, 5.48; N, 7.63. Found: C, 50.76; H, 5.46; N, 7.61.

Example 12

1-(Cyclopropylmethyl)-2-(4-ethoxybenzyl)-N,N-diethyl-1H-benzimidazole-5-carboxamide 12A: 4-[(Cyclopropylmethyl)amino]-N,N-diethyl-3-nitrobenzamide.

Following general procedure 2B: N,N-diethyl-4-fluoro-3-nitrobenzamide (0.823 g, 3.42 mmol) and cyclopropylmethanamine (0.39 mL, 4.50 mmol) in 80% aqueous ethanol (17 mL) were stirred at 85° C. for 16 h. The crude product (1.00 g), an orange solid, was used in subsequent steps. $^1$H-NMR (CD$_3$OD): δ 8.23 (d, J=2.0 Hz, 1H), 7.55 (dd, J=9.2 Hz, J=2.0 Hz, 1H), 7.09 (d, J=9.2 Hz, 1H), 3.47 (br s, 3H), 3.31 (q, J=2.0 Hz, 2H), 3.27 (d, J=6.4 Hz, 2H), 1.23 (overlapping t and m, J=7.0 Hz, 7H), 0.68–0.60 (m, 2H), 0.40–0.34 (m, 2H). MS (ESI) (M+H)$^+$=292.

12B: 3-Amino-4-[(cyclopropylmethyl)amino]-N,N-diethylbenzamide.

Following general procedure 2C, 4-[(cyclopropylmethyl)amino]-N,N-diethyl-3-nitrobenzamide (1.00 g) was hydrogenated for 24 h to give the title compound (0.889 g) as a greenish-tan solid. The crude product was used in subsequent steps. $^1$H-NMR (CD$_3$OD): δ 6.72–6.78 (m, 2H), 6.58 (d, J=8.4 Hz, 1H), 3.43 (br s, 4H), 2.99 (d, J=6.4 Hz, 2H), 1.18 (overlapping br t and m, J=6.4 Hz, 7H), 0.59–0.52 (m, 2H), 0.30–0.24 (m, 2H). MS (ESI) (M+H)$^+$=262.

12C: 1-(Cyclopropylmethyl)-2-(4-ethoxybenzyl)-N,N-diethyl-1H-benzimidazole-5-carboxamide.

Following general procedure 2D: (4-ethoxyphenyl)acetyl chloride (0.109 g, 0.547 mmol) was added 3-amino-4-[(cyclopropylmethyl)amino]-N,N-diethylbenzamide (0.130 g, 0.497 mmol) in acetic acid (2 mL) and the mixture was stirred at 90° C. overnight. After work-up, the crude product was purified by reverse-phase HPLC to provide the title compound as a TFA salt (0.042 g, 14%) as an oil. $^1$H-NMR (DMSO-d$_6$): δ 7.59 (d, J=8.4 Hz, 1H), 7.30 (s, 1H), 7.08 (d, J=7.2 Hz, 1H), 6.91 (d, J=9.2 Hz, 2H), 6.53 (d, J=8.4 Hz, 2H), 4.14 (s, 2H), 3.97 (d, J=7.2 Hz, 2H), 3.60 (q, J=6.4 Hz, 2H), 3.04 (br s, 2H), 2.80 (br s, 2H), 0.90 (t, J=6.4 Hz, 3H), 0.78 (br m, 7H), 0.10–0.03 (m, 4H). MS (ESI) (M+H)$^+$=406. Anal. Calcd for C$_{25}$H$_{31}$N$_3$O$_2$+1.9 TFA: C, 55.60; H, 5.33; N, 6.75. Found: C, 55.51; H, 5.25; N, 6.74.

Example 13

1-(Cyclopropylmethyl)-2-[(6-ethoxy-3-pyridinyl)methyl]-N,N-diethyl-1H-benzimidazole-5-carboxamide 13A: (6-ethoxy-3-pyridinyl)acetic Acid.

To a stirred solution of (6-chloro-3-pyridinyl)acetic acid (0.094 g, 0.545 mmol) in EtOH (1.6 mL) was added 3.1 M EtONa in EtOH (0.7 mL, 2.17 mmol) and the reaction mixture was stirred at 100° C. room temperature for 24 hours after which an excess of NaH (60% dispersion in oil) was added together with 1 mL EtOH and heating at 100° C. was continued for 96 h. The solvent was evaporated in vacuo and the residue was taken up into diethyl ether (5 mL). The organic phase was washed with diluted HCl (2×2 mL) and brine (2 mL), dried over MgSO$_4$, filtered, and concentrated in vacuo to provide the title compound (0.081 g, 82%) as a pale brown solid, which was used without further purification. $^1$H NMR (CDCl$_3$): δ 10.06 (br s, 1H), 8.06 (s, 1H), 7.55 (d, J=9.2 Hz, 1H), 6.72 (d, J=8.4 Hz, 1H), 4.30 (q, J=6.1 Hz, 2H), 3.58 (s, 2H) 1.38 (t, J=8.0, 3H). MS (ESI) (M+H)$^+$=182.

13B: 1-(Cyclopropylmethyl)-2-[(6-ethoxy-3-pyridinyl)methyl]-N,N-diethyl-1H-benzimidazole-5-carboxamide.

To a stirred solution of (6-ethoxy-3-pyridinyl)acetic acid (0.081 g, 0.448 mmol) in DMF (2 mL) was added O-(7-azabenzotriazol-1-yl)-N,N,N',N'-tetramethyluronium hexafluorophosphate (HATU) (0.178 g, 0.468 mmol) and DIPEA (0.156 mL, 0.895 mmol) and the reaction mixture was stirred at room temperature for 10 min. 3-amino-4-[(cyclopropylmethyl)amino]-N,N-diethylbenzamide (0.111 g, 0.448 mmol) was added and the resulting mixture was stirred 1 hour at room temperature. The mixture was diluted with EtOAc (15 mL), washed with saturated NaHCO$_3$ (8 mL) and then brine (8 mL), dried over MgSO$_4$ and concentrated in vacuo to give a crude amide which was used without further purification.

The above crude intermediate was dissolved in acetic acid (5 mL) and the mixture was heated at 90° C. overnight. The reaction mixture was concentrated and the residue was taken up into EtOAc (15 mL). The organic phase was washed with 1 N NaOH (2×8 mL) and then brine (8 mL), dried over MgSO$_4$ and concentrated in vacuo. The crude product was purified by silica gel column chromatography (2% MeOH/EtOAc) to provide the title compound (0.111 g, 65%) as a pale brown solid. $^1$H-NMR (CDCl$_3$): δ 8.05 (s, 1H), 7.75 (s, 1H), 7.49 (d, J=8.4 Hz, 1H), 7.38–7.30 (m, 2H), 6.68 (d, J=8.4 Hz, 1H), 4.32 (qd, J=7.2 Hz, J=2.2 Hz, 2H), 4.25 (s, 2H), 3.55 (br s, 2H), 3.38 (br s, 2H), 1.38 (td, J=6.8 Hz, J=2.0 Hz, 3H), 1.22 (br s, 6H), 1.12–1.03 (m, 1H), 0.60–0.54 (m, 2H), 0.33–0.28 (m, 2H). MS (ESI) (M+H)$^+$=407. Anal. Calcd for C$_{24}$H$_{28}$N$_4$O$_2$+0.2H$_2$O: C, 70.63; H, 7.01; N, 13.73. Found: C, 70.83; H, 7.50; N, 13.67.

Example 14

1-[2-(Dimethylamino)ethyl]-2-[2-(4-ethoxyphenyl)ethyl]-N,N-diethyl-1H-benzimidazole-5-carboxamide 14A: 4-{[2-(Dimethylamino)ethyl]amino}-N,N-diethyl-3-nitrobenzamide.

Following general procedure 2B, N,N-diethyl-4-fluoro-3-nitrobenzamide (0.534 g, 2.22 mmol) and N$^1$,N$^1$-dimethyl- 1,2-ethanediamine (0.22 mL, 2.02 mmol) were stirred at 85° C. for 14 h. The crude product was purified through dissolution in 1 N HCl and extraction with Et$_2$O (2×15 mL). The aqueous phase was adjusted to pH 11 with 5 N NaOH and then extracted with CH$_2$Cl$_2$ (4×15 mL). The combined CH$_2$Cl$_2$ phases were dried over MgSO$_4$, filtered, and concentrated in vacuo to provide the title compound (0.560 g, 82%) as an orange oil. $^1$H-NMR (CD$_3$OD): δ 8.22 (d, J=2.8 Hz, 1H), 7.56 (dd, J=8.4 Hz, J=2.8 Hz, 1H), 7.09 (d, J=8.4 Hz, 1H), 3.53–3.40 (overlapping t, J=6.4 Hz, and br s, 6H), 2.67 (t, J=6.4 Hz, 2H), 2.33 (s, 6H), 1.22 (t, J=7.6 Hz, 6H). MS (ESI) (M+H)$^+$=309

14B: 3-Amino-4-{[2-(dimethylamino)ethyl]amino}-N,N-diethylbenzamide.

Following general procedure 2C, 4-{[2-(dimethylamino)ethyl]amino}-N,N-diethyl-3-nitrobenzamide (0.560 g, 1.82 mmol) was hydrogenated for 3 h to give the title compound (0.531 g) as a greenish-tan solid. The crude product was used in subsequent steps. $^1$H-NMR (CD$_3$OD): δ 6.77, 6.76 (overlapping s and dd, J=6.4 Hz, J=2.0 Hz, 2H), 6.61 (d, J=8.4 Hz, 1H), 3.45 (br s, 4H), 3.29 (t, J=6.4 Hz, 2H), 2.66 (t, J=6.4 Hz, 2H), 2.34 (s, 6H), 1.19 (br t, J=6.8 Hz, 6H). MS (ESI) (M+H)$^+$=279

14C: 1-[2-(Dimethylamino)ethyl]-2-[2-(4-ethoxyphenyl) ethyl]-N,N-diethyl-1H-benzimidazole-5-carboxamide.

Following procedure 13B, 3-(4-ethoxyphenyl)propanoic acid (0.0386 g, 0.198 mmol), HATU (0.0756 g, 0.199 mmol), DIPEA (0.047 mL, 0.27 mmol), and 4-{[2-(dimethylamino)ethyl]amino}-N,N-diethyl-3-aminobenzamide (0.0503 g, 0.180 mmol) were combined. The crude product was purified by column chromatography (9:1 CH$_2$Cl$_2$:MeOH) to provide the title compound (0.0284 g, 36%). $^1$H-NMR (CD$_3$OD): δ 7.64 (s, 1H), 7.53 (d, J=8.4 Hz, 1H), 7.29 (d, J=8.4 Hz, 1H), 7.06 (d, J=8.4 Hz, 2H), 6.78 (d, J=8.4 Hz, 2H), 4.14 (t, J=8.0 Hz, 2H), 3.96 (q, J=7.2 Hz, 2H), 3.57 (br s, 2H), 3.35 (br s, 2H), 3.21–3.10 (m, 4H), 2.43 (t, J=7.6 Hz, 2H), 2.26 (s, 6H), 1.34 (t, J=7.2 Hz, 3H), 1.26, 1.16 (2 overlapping br s, 6H). $^{13}$-NMR (CD$_3$OD): δ 174.03, 159.16, 158.09, 142.67, 136.55, 133.78, 132.24, 130.54, 122.10, 117.34, 115.65, 111.44, 64.43, 58.74, 45.80, 45.16, 42.64, 41.00, 34.46, 30.53, 15.18, 14.43, 13.12. MS (ESI) (M+H)$^+$=437. The HCl salt was prepared using HCl in Et$_2$O. A white solid was obtained after lyophilization. Anal. Calcd for C$_{26}$H$_{36}$N$_4$O$_2$.2.8 HCl.2.2H$_2$O: C, 54.00; H, 7.53; N, 9.69. Found: C, 54.12; H, 7.53; N, 9.36.

Example 15

1-(Cyclopropylmethyl)-2-[2-(4-ethoxyphenyl)ethyl]-N,N-diethyl-1H-benzimidazole-5-carboxamide Following general procedure 13B, 3-(4-ethoxyphenyl) propanoic acid (0.0409 g, 0.211 mmol), HATU (0.0801 g, 0.211 mmol), DIPEA (0.050 mL, 0.29 mmol), and 3-amino-4-[(cyclopropylmethyl)amino]-N,N-diethylbenzamide (0.0500 g, 0.191 mmol) were combined. The crude product was purified by column chromatography (19:1 CH$_2$Cl$_2$: MeOH) to provide the title compound (0.0457 g, 57%). $^1$H-NMR (CD$_3$OD): δ 7.64 (s, 1H), 7.55 (d, 8.4 Hz, 1H), 7.27 (d, J=8.4 Hz, 1H), 7.08 (d, J=8.4 Hz, 2H), 6.77 (d, J=8.4 Hz, 2H), 3.97 (d, J=7.2 Hz, 2H), 3.95 (q, J=6.8 Hz, 2H), 3.57 (br s; 2H), 3.34 (br s, 2H), 3.23-3.07 (m, 4H), 1.34 (t, J=6.4 Hz, 3H), 1.36–1.02 (overlapping 2×br s and m, 7H), 0.55–0.46 (m, 2H), 0.40–0.32 (m, 2H). $^{13}$C-NMR (CD$_3$OD): δ 174.08, 159.08, 157.72, 142.60, 136.95, 133.70, 132.03, 130.46, 121.97, 117.21, 115.59, 111.83, 64.41, 48.69, 45.15, 40.98, 34.38, 30.54, 15.18, 14.43, 13.12, 12.15, 4.54. MS (ESI) (M+H)$^+$=420. The HCl salt was prepared using HCl in Et$_2$O. A white solid was obtained after lyophilization. Anal. Calcd for C$_{26}$H$_{33}$N$_3$O$_2$.1.0HCl.0.8H$_2$O: C, 66.38; H, 7.63; N, 8.93. Found: C, 66.35; H, 7.60; N, 8.81.

Example 16

2-(4-Ethoxybenzyl)-N,N-diethyl-1-isopentyl-1H-benzimidazole-5-carboxamide

16A: N,N-Diethyl-4-(isopentylamino)-3-nitrobenzamide.

Following general procedure 2B, N,N-diethyl-4-fluoro-3-nitrobenzamide (1.077 g, 4.48 mmol) and 3-methyl-1-butanamine (0.68 mL, 5.83 mmol) were stirred at 85° C. for 14 h to provide the title compound (1.425 g) as an orange oil. The crude product was used in subsequent steps. $^1$H-NMR (CD$_3$OD): δ 8.22 (d, J=2.0 Hz, 1H), 7.56 (dd, J=9.2 Hz, J=2.0 Hz, 1H), 7.09 (d, J=9.2 Hz, 1H), 3.52–3.40 (br m, 6H), 1.83–1.72 (m, 1H), 1.64 (q, J=7.6 Hz, 2H), 1.23 (t, J=7.6 Hz, 6H), 1.01 (d, J=6.8 Hz, 6H). MS (ESI) (M+H)$^+$=308.

16B: 3-Amino-N,N-diethyl-4-(isopentylamino)benzamide.

Following general procedure 2C, N,N-diethyl-4-(isopentylamino)-3-nitrobenzamide (1.425 g, 4.64 mmol) was hydrogenated for 41 h to give the title compound (1.312 g) as a deep blue solid. The crude product was used in subsequent steps. $^1$H-NMR (CD$_3$OD): δ 6.78–6.74 (m, 2H), 6.58 (d, J=8.4 Hz, 1H), 3.45 (br s, 4H), 3.17 (t, J=7.6 Hz, 2H), 1.83–1.72 (m, 1H), 1.59 (q, J=7.2 Hz, 2H), 1.19 (t, J=6.4 Hz, 6H), 0.98 (d, J=6.4 Hz, 6H). MS (ESI) (M+H)$^+$=278

16C: 2-(4-Ethoxybenzyl)-N,N-diethyl-1-isopentyl-1H-benzimidazole-5-carboxamide.

Following general procedure 13B, (4-ethoxyphenyl)acetic acid (0.110 g, 0.612 mmol), HATU (0.233 g, 0.611 mmol), DIPEA (0.15 m, 0.86 mmol), and 3-amino-N,N-diethyl-4-(isopentylamino)benzamide (0.154 g, 0.556 mmol) were combined. The crude product was purified by column chromatography (19:1 CH$_2$Cl$_2$:MeOH) to provide the title compound (0.211 g, 90%). $^1$H-NMR (CD$_3$OD): δ 7.67 (s, 1H), 7.50 (d, J=8.4 Hz, 1H), 7.30 (dd, J=8.4 Hz, J=2.0 Hz, 1H), 7.16 (d, J=9.2 Hz, 2H), 6.86 (d, J=8.4 Hz, 2H), 4.28 (s, 2H), 4.12 (m, 2H), 3.98 (q, J=7.6 Hz, 2H), 3.57 (br s, 2H), 3.34 (br s, 2H), 1.62–1.48 (m, 1H), 1.34 (t, J=7.6 Hz, 3H), 1.36–1.07 (overlapping 2×br s and m, 8H), 0.88 (d, J=6.8 Hz, 6H). MS (ES) (M+H)$^+$=422. Anal. Calcd for C$_{26}$H$_{35}$N$_3$O$_2$.1.7 TFA.0.2H$_2$O: C, 57.05; H, 6.04; N, 6.79. Found: C, 57.11; H, 6.09; N, 6.69.

Example 17

2-(4-Ethoxybenzyl)-N,N-diethyl-1-(4-pyridinylmethyl)-1H-benzimidazole-5-carboxamide 17A: N,N-Diethyl-3-nitro-4-[(4-pyridinylmethyl)amino] benzamide.

Following general procedure 2B, N,N-diethyl-4-fluoro-3-nitrobenzamide (0.272 g, 1.13 mmol) and 4-pyridinylmethanamine (0.11 mL, 1.12 mmol) were stirred at room temperature for 87 h. The crude product was purified by column chromatography (100% EtOAc, then 9:1 CH$_2$Cl$_2$:MeOH) to provide the title compound (0.181 g, 60%). $^1$H-NMR (CD$_3$OD): δ 8.49 (d, J=6.4 Hz, 2H), 8.27 (d, J=2.8 Hz, 1H), 7.50–7.42 (m, 3H), 6.87 (d, J=8.4 Hz, 1H), 4.77 (s, 2H), 3.44 (br s, 4H), 1.21 (t, J=7.2 Hz; 6H). MS (ESI) (M+H)$^+$=329

17B: 3-Amino-N,N-diethyl-4-[(4-pyridinylmethyl)amino]benzamide.

Following general procedure 2C, N,N-diethyl-3-nitro-4-[(4-pyridinylmethyl)-amino]benzamide (0.181 g, 0.551 mmol) was hydrogenated for 20 h to give the title compound (0.172 g) as a viscous brown oil. The crude product was used in subsequent steps. $^1$H-NMR (CD$_3$OD): δ 8.45 (d, J=6.8 Hz, 2H), 7.46 (d, J=6.4 Hz, 2H), 6.79 (d, J=2.0 Hz, 1H), 6.64 (dd, J=7.2 Hz, J=2.0 Hz, 1H), 6.36 (d, J=8.4 Hz, 1H), 4.51 (s, 2H), 3.42 (br s, 4H), 1.17 (br t, 6H). MS (ESI) (M+H)+ 299

17C: 2-(4-Ethoxybenzyl)-N,N-diethyl-1-(4-pyridinylmethyl)-1H-benzimidazole-5-carboxamide.

Following general 13B, (4-ethoxyphenyl)acetic acid (0.0364 g, 0.202 mmol), HATU (0.0768 g, 0.202 mmol), DIPEA (0.048 mL, 0.28 mmol), and 3-amino-N,N-diethyl-4-[(4-pyridinylmethyl)amino]benzamide (0.0548 g, 0.184 mmol) were combined. The crude product was purified by reverse phase MPLC (gradient 10–50% CH$_3$CN in H$_2$O) to provide the title compound (0.0459 g, 36%) as its TFA salt. This material was lyophilized from H$_2$O/dioxane to produce a white solid. $^1$H-NMR (CD$_3$OD): δ 8.60 (br s, 2H), 7.87 (s, 1H), 7.70 (d, J=8.4 Hz, 1H), 7.52 (dd, J=8.4 Hz, J=2.0 Hz, 1H), 7.42 (d, J=5.6 Hz, 2H), 7.13 (d, J=8.4 Hz, 2H), 6.71 (d, J=9.6 Hz, 2H), 6.06 (s, 2H), 4.54 (s, 2H), 3.93 (q, J=7.2 Hz, 2H), 3.59 (br s, 2H), 3.31 (br s, 2H), 1.35 (t, J=6.8 Hz, 3H), 1.38–1.04 (2×br s, 6H). MS (ESI) (M+H)+443. Anal. Calcd for C$_{27}$H$_{30}$N$_4$O$_2$.2.1 TFA. 0.8H$_2$O: C, 53.81; H, 4.88; N, 8.04. Found: C, 53.74; H, 4.89; N, 8.07.

Example 18

2-(4-Ethoxybenzoyl)-N,N-diethyl-1-isopentyl-1-benzimidazole-5-carboxamide

MnO$_2$ (0.641 g, 7.37 mmol) was added to a stirred solution of 2-(4-ethoxybenzyl)-N,N-diethyl-1-isopentyl-1H-benzimidazole-5-carboxamide (0.211 g, 0.500 mmol) in dry dioxane (4 mL) under an atmosphere of N$_2$. The reaction was heated to 50° C. After 64 h, an additional portion of MnO$_2$ (0.600 g, 6.90 mmol) was added and heating was continued at 50° C. for another 24 h. The reaction was cooled to room temperature, diluted with CH$_2$Cl$_2$, and filtered through diatomaceous earth. The solids were washed well with additional CH$_2$Cl$_2$, and the filtrate was concentrated to provide the crude product. Purification by column chromatography (1:1 EtOAc:Heptane) afforded the title compound (0.139 g, 64%) as a viscous, colorless oil. $^1$H-NMR (CD$_3$OD): δ 8.19 (d, J=9.6 Hz, 2H), 7.83 (s, 1H), 7.72 (d, J=8.4 Hz, 1H), 7.48 (dd, J=8.4 Hz, J=1.6 Hz, 1H), 7.01 (d, J=9.2 Hz, 2H), 4.53 (dd, J=7.6 Hz, J=7.2 Hz, 2H), 4.13 (q, J=6.4 Hz, 2H), 3.58 (br s, 2H), 3.36 (br s, 2H), 1.78–1.70 (m, 2H), 1.72–10.56 (m, 1H), 1.41 (t, J=7.2 Hz, 3H), 1.34–1.10 (2×br s, 6H), 0.94 (d, J=6.8 Hz, 6H). $^{13}$C-NMR (CD$_3$OD): δ 185.72, 173.32, 165.47, 149.57, 142.00, 137.18, 134.65, 133.57, 130.19, 124.88, 119.93, 115.31, 112.75, 65.10, 45.12, 44.94, 41.00, 40.13, 27.18, 22.79, 14.99, 14.46, 13.12. MS (ESI) (M+H)+=436. Anal. Calcd for C$_{26}$H$_{33}$N$_3$O$_3$. .0.5H$_2$O: C, 70.24; H, 7.71; N, 9.45. Found: C, 70.40; H, 7.64; N, 8.97.

Example 19

2-(4-Ethoxybenzoyl)-N,N-diethyl-1-isopentyl-1H-benzimidazole-5-carbothioamide

Lawesson's reagent (0.0963 g, 0.238 mmol) was added to a stirred solution of 2-(4-ethoxybenzoyl)-N,N-diethyl-1-isopentyl-1H-benzimidazole-5-carboxamide (0.0451 g, 0.104 mmol) in dry toluene (5 mL) under an atmosphere of N$_2$. The reaction was heated to reflux for 0.5 h, and then cooled to room temperature and concentrated. The residue was purified by column chromatography (3:1 Hexanes:EtOAc) to provide the title compound (0.0137 g, 29%) as a glassy yellow solid. $^1$H-NMR (CD$_3$OD): δ 8.19 (d, J=9.2 Hz, 2H), 7.67 (d, J=8.4 Hz, 1H), 7.64 (s, 1H), 7.36 (d, J=8.4 Hz, 1H), 7.06 (d, J=9.2 Hz, 2l), 4.55 (dd, J=8.4 Hz, J=7.2 Hz, 2H), 4.17 (q, J=7.6 Hz, 4H), 3.53 (q, J=7.6 Hz, 2H), 1.80–1.71 (m, 2H), 1.71–1.58 (m, 1H), 1.44 (t, J=7.6 Hz, 3H), 1.41 (t, J=7.6 Hz, 3H), 1.17 (t, J=7.6 Hz, 3H), 0.97 (d, J=6.4 Hz, 6H). $^{13}$C-NMR (CD$_3$OD): δ 201.23, 185.95, 165.57, 149.55, 141.87, 141.18, 136.28, 134.64, 130.31, 124.56, 118.20, 115.41, 112.36, 65.15, 47.48, 44.89, 40.18, 27.20, 22.77, 14.95, 14.07, 11.44. MS (ESI) (M+H)+=452. Anal. Calcd for C$_{26}$H$_{33}$N$_3$O$_2$S.0.3H$_2$O: C, 68.33; H, 7.41; N, 9.19. Found: C, 68.44; H, 7.52; N, 9.01.

Example 20

N-Cyclohexyl-1-(cyclopropylmethyl)-2-(4-ethoxybenzyl)-N-methyl-1H-benzimidazole-5-carboxamide 20A: 4-[(Cyclopropylmethyl)amino]-3-nitrobenzonitrile.

Following the general procedure 2B, 733 mg (4.42 mmol) of 4-fluro-3-nitrobenzonitrile in 80% aqueous ethanol (20 mL) was added cyclopropylmethylamine (377 mg, 5.3 mmol) at room temperature. The mixture was stirred at 60° C. for 3 h before work-up. The crude product (920 mg, 96%) was used for the next step without further purification. $^1$H NMR (400 MHz, CDCl$_3$): δ 8.52 (s, 1H), 8.51–8.47 (br, 1H), 7.59 (d, J=8.4 Hz, 1H), 6.90 (d, J=8.4 Hz, 1H), 3.22–3.20 (m, 2H), 1.25–1.15 (m, 1H), 0.73–0.59 (m, 2H), 0.42–0.35 (m, 2H). MS (ESI) [2×(M+H)+]: 436.

20B: 3-amino-4-[(Cyclopropylmethyl)amino]benzonitrile.

Following the general procedure 2C, crude 4-[(cyclopropylmethyl)-amino]-3-nitrobenzonitrile (920 mg, 4.24 mmol) was hydrogenated for 2 h (35 psi) in 40 mL of EtOAc to yield 750 mg crude product (95%) and was used for the next step without further purification. MS (ESI) (M+H)+=188.

20C: 1-(Cyclopropylmethyl)-2-(4-ethoxybenzyl)-1H-benzimidazole-5-carbonitrile.

Following the general procedure 2D, the freshly prepared (4-ethoxyphenyl)acetyl chloride (from 793 mg of acid, 4.4 mmol) and crude 3-amino-4-[(cyclopropylmethyl)amino]benzonitrile (750 mg, 4.01 mmol) were heated in acetic acid (HOAc) overnight. After work-up, the crude residue was purified by silica gel column chromatography to afford pure product (1.04 g, 78%) as an off-white solid. $^1$H NMR (400 MHz, CDCl$_3$): δ 8.08 (s, 1H), 7.50 (d, J=8.4 Hz, 1H), 7.38 (d, J=8.4 Hz, 1H), 7.14 (d, J=8.4 Hz, 2H), 6.84 (d, J=8.4 Hz, 2H), 4.29 (s, 2H), 4.01 (d, J=7.6 Hz, 2H), 3.96 (q, J=7.6 Hz, 2H), 1.39 (t, J=7.6 Hz, 3H), 1.04–1.00 (m, 1H), 0.58–0.53 (m, 2H), 0.29–0.25 (m, 2H). MS (ESI) (M+H)+=332. Anal. Calcd for C$_{21}$H$_{21}$N$_3$O.0.1H$_2$O: C, 75.50; H, 6.41; N, 12.61. Found: C, 75.76; H, 6.72; N, 12.45.

20D: 1-(Cyclopropylmethyl)-2-(4-ethoxybenzyl)-1H-benzimidazole-5-carboxylic acid.

To a solution of 1-(cyclopropylmethyl)-2-(4-ethoxybenzyl)-1H-benzimidazole-5-carbonitrile (500 mg, 1.51 mmol) in 1:1 EtOH:H$_2$O (16 mL) was added KOH (338 mg, 6.04 mmol). The resulting mixture was refluxed for 36 h. The mixture was acidified with 1 N HCl to pH~6.0, the precipitate was collected by filtration to give white solids (520 mg, 99%) which was used for the next step without further purification. The analytically pure compound was obtained by recrystallization (from EtOH:H$_2$O). $^1$H NMR (400 MHz, CD$_3$OD): δ 8.25 (s, 1H), 7.89 (d, J=8.4 Hz, 1H), 7.47 (d, J=8.4 Hz, 1H), 7.18 (d, J=8.2 Hz, 2H), 6.82 (d, J=8.2 Hz, 2H), 4.28 (s, 2H), 4.06 (d, J=6.8 Hz, 2H), 3.89 (q, J=7.6 Hz, 2H), 1.32 (t, J=7.6 Hz, 3H), 1.06–0.92 (m, 1H), 0.50–0.48 (m, 2H), 0.32–0.26 (m, 2H). MS (ESI) (M+H)$^+$=351. Anal. Calcd for C$_{21}$H$_{22}$N$_2$O$_3$.0.7HCl: C, 67.09; H, 6.09; N, 7.45. Found: C, 66.98; H, 6.31; N, 7.09.

20E: N-Cyclohexyl-1-(cyclopropylmethyl)-2-(4-ethoxybenzyl)-N-methyl-1H-benzimidazole-5-carboxamide 1-(Cyclopropylmethyl)-2-(4-ethoxybenzyl)-1H-benzimidazole-5-carboxylic acid (80 mg, 0.228 mmol) was dissolved in DMF (2 mL) and then HATU (104 mg, 0.274 mmol) was added followed by DIPEA (48 μL, 0.274 mmol). After stirring for 10 min; cyclohexylmethyl amine (0.456 mmol) was added and the resulting mixture was stirred overnight. The mixture was diluted with EtOAc (50 mL), washed with saturated NaHCO$_3$ (2×10 mL) and then H$_2$O (2×10 mL), dried over MgSO$_4$, and concentrated to give a crude amide. The crude residue was purified by silica gel column chromatography to give pure product which was treated with 1 M HCl solution in diethyl ether to form a HCl salt as white solids (93 mg, 78%). $^1$H NMR (400 MHz, CD$_3$OD): δ 7.66 (s, 1H), 7.58 (d, J=8.0 Hz, 1H), 7.30 (d, J=8.0 Hz, 1H), 7.16 (d, J=8.6 Hz, 2H), 6.84 (d, J=8.6 Hz, 2H), 4.30 (s, 2H), 4.10–4.04 (m, 5H), 3.96 (q, J=7.6 Hz, 2H), 3.66–3.54 (m, 1H), 1.90–1.50 (m, 10H), 1.33 (t, J=7.6 Hz, 3H), 1.10–0.98 (m, 1H), 0.50–0.42 (m, 2H), 0.32–0.27 (m, 2H). MS (ESI) (M+H)$^+$=446. Anal. Calcd for C$_{28}$H$_{35}$N$_3$O$_2$.2.2HCl: C, 63.96; H, 7.13; N, 7.99. Found: C, 64.11; H, 7.24; N, 7.73.

Example 21

1-(Cyclopropylmethyl)-2-(4-ethoxybenzyl)-5-(1-pyrrolidinylcarbonyl)-1H-benzimidazole Following the general procedure 20E, 1-(cyclopropylmethyl)-2-(4-ethoxybenzyl)-1H-benzimidazole-5-carboxylic acid (80 mg, 0.228 mmol) was dissolved in DMF (2 mL) and then HATU (104 mg, 0.274 mmol) was added followed by DIPEA (48 μL, 0.274 mmol), After being stirred for 10 min, pyrrolidine (0.456 mmol) was added and the resulting mixture was stirred overnight. The crude residue after work-up was purified by silica gel column chromatography to give pure product which was treated with 1 M HCl solution in diethyl ether to form a HCl salt as white solids (82 mg, 79%). 1H N (400 MHz, CD$_3$OD): δ 7.85 (s, 1H), 7.59 (d, J=8.6 Hz, 1H), 7.48 (d, J=8.6 Hz, 1H), 7.18 (d, J=8.1 Hz, 2H), 6.87 (d, J=8.1 Hz, 2H), 4.32 (s, 2H), 4.07 (d, J=6.8 Hz, 2H), 4.00 (q, J=7.6 Hz, 2H), 3.64 (t, J=. 7.2 Hz, 2H), 3.53 (t, J=7.2 Hz, 2H), 2.06–1.96 (m, 2H), 1.96–1.85 (m, 2H), 1.36 (t, J=7.6 Hz, 3H), 1.10–1.04 (m, 1H), 0.52–0.46 (m, 2H), 0.34–0.28 (m, 2H). MS (ESI) (M+H)$^+$=404. Anal. Calcd for C$_{25}$H$_{29}$N$_3$O$_2$.1.5HCl: C, 65.53; H, 6.71; N, 9.17. Found: C, 65.48; H, 6.77; N, 8.75.

Example 22

1-(Cyclopropylmethyl)-2-(4-ethoxybenzyl)-5-(1-pyrrolidinylcarbothioyl)-1H-benzimidazole To a solution of free base 1-(cyclopropylmethyl)-2-(4-ethoxybenzyl)-5-(1-pyrrolidinylcarbonyl)-1H-benzimidazole (Example 21, from 80 mg 1-(cyclopropylmethyl)-2-(4-ethoxybenzyl)-1H-benzimidazole-5-carboxylic acid) in pyridine (2 mL) was added P$_2$S$_5$ (507 mg, 1.14 mmol). The mixture was heated at 100° C. for 24 h and cooled to room temperature. After being decanted, the supernatant was concentrated and the residue was diluted with EtOAc (20 mL), washed with 1 N NaOH (2×10 mL) and then H$_2$O (2×10 mL). The organic layer was dried over MgSO$_4$ and was evaporated. The crude residue was purified by silica gel column chromatography to give an oil (59 mg, 62% for 2 steps). $^1$H NMR (400 MHz, CD$_3$OD): δ 7.70 (s, 1H), 7.39 (d, J=8.0 Hz, 1H), 7.28 (d, J=8.0 Hz, 1H), 7.12 (d, J=8.4 Hz, 2H), 6.81 (d, J=8.4 Hz, 2H), 4.27 (s, 2H), 4.08–3.95 (m, 4H), 3.89 (d, J=6.8 Hz, 2H), 3.57 (t, J=7.2 Hz, 2H), 2.14–2.03 (m, 2H), 2.00–1.92 (m, 2H), 1.38 (t, J=7.2 Hz, 3H), 1.06–0.98 (m, 1H), 0.54–0.48 (m, 2H), 0.28–0.22 (m, 2H). MS (ESI) (M+H)$^+$=420.

Example 23

1-(Cyclopropylmethyl)-2-[(5-ethoxy-2-pyridinyl)methyl]-(1-pyrrolidinylcarbonyl)-1H-benzimidazole

23A: [5-(Benzyloxy)-2-pyridinyl]acetic Acid.

To a solution of 1.45 g (6.46 mmol) [5-(benzyloxy)-2-pyridinyl]acetonitrile (obtained in 6 steps from 6-methyl-3-pyridinol, see: W. M. Golebiewski and J. T. Wrobel, *Bull. Pol. Acad. Sci.*, 1990, 38, 17) in MeOH (9 mL) was added 25% NaOH (3 mL). The reaction mixture was stirred at reflux for 48 h. After being cooled, most of the MeOH was removed in vacuo, water (10 mL) was added and the aqueous solution was washed with diethyl ether (2×10 mL) followed by acidification (pH ~6.0). The mixture was extracted with EtOAc (3×20 mL), dried over MgSO$_4$ and concentrated to give pale yellow crystals (1.4 g, 89%). MS (ESI) (M+H)$^+$=244.

23B: 2-{[5-(Benzyloxy)-2-pyridinyl]methyl}-1-(cyclopropylmethyl)-1H-benzimidazole-5-carbonitrile.

Following the general procedure 13B, 360 mg (1.48 mmol) of [5-(benzyloxy)-2-pyridinyl]acetic acid was coupled with 3-amino-4-[(Cyclopropylmethyl)amino]benzonitrile using HATU. The resulting intermediate was heated in HOAc (20 mL) at 90° C. overnight. After being concentrated, the crude residue was purified by silica gel column chromatography to afford the pure product (230 mg, 40% for 2 steps) as an oil. MS (ESI) (M+H)$^+$=395.

23C: 1-(cyclopropylmethyl)-2-[(5-hydroxy-2-pyridinyl)methyl]-1H-benzimidazole-5-carbonitrile.

To a solution of 2-{[5-(benzyloxy)-2-pyridinyl]methyl}-1-(cyclopropylmethyl)-1H-benzimidazole-5-carbonitrile (200 mg, 0.51 mmol) in EtOH (10 mL) was added 10% Pd/C (20 mg). The mixture was hydrogenated overnight (40 psi). After filtration and concentration, the crude product was obtained as a pale yellow oil (120 mg, 77%) which was used in the next step without further purification. MS (ESI) (M+H)$^+$=305.

23D: 1-(Cyclopropylmethyl)-2-[(5-ethoxy-2-pyridinyl)methyl]-1H-benzimidazole-5-carbonitrile.

To a solution of 1-(cyclopropylmethyl)-2-[(5-hydroxy-2-pyridinyl)methyl]-1H-benzimidazole-5-carbonitrile (120 mg, 0.394 mmol) in DMSO (1 mL) was added MeONa (25% in MeOH, 0.47 mmol). After being stirred at room temperature for 30 min, MeOH was removed in vacuo and EtI (0.47 mmol) was added, and the resulting mixture was stirred at room temperature overnight. The solution was diluted with $H_2O$ (10 mL), extracted with EtOAc (2×20 mL), washed with $H_2O$ (2×10 mL), and lastly dried over $MgSO_4$. The residue obtained after evaporation was purified by silica gel column chromatography to give the pure product as an oil (84 mg, 64%). $^1$H NMR (400 MHz, $CDCl_3$): δ 8.19 (d, J=3.0 Hz, 1H), 8.04 (s, 1H), 7.49 (d, J=8.4 Hz, 1H), 7.42 (d, J=8.4 Hz, 1H), 7.24 (d, J=8.8 Hz, 1H), 7.13 (dd, J=10.0 Hz, J=2.8 Hz, 1H), 4.47 (s, 2H), 4.15 (d, J=6.8 Hz, 2H), 4.04 (q, J=7.0 Hz, 2H), 1.41 (t, J=7.0 Hz, 3H), 1.14–1.08 (m, 1H), 0.60–0.54 (m, 2H), 0.36–0.30 (m, 2H). MS (ES) $(M+H)^+$=333.

23E: 1-(cyclopropylmethyl)-2-[(5-ethoxy-2-pyridinyl)methyl]-1H-benzimidazole-5-carboxylic acid.

To a solution 1-(cyclopropylmethyl)-2-[(5-ethoxy-2-pyridinyl)methyl]-1H-benzimidazole-5-carbonitrile (400 mg, 1.203 mmol) in 1:1 EtOH:$H_2O$ (12 mL) was added KOH (269 mg, 4.81 mmol). The resulting mixture was refluxed for 36 h. The mixture was acidified with 1 N HCl to pH~6.0. The precipitate (397 mg, 94%) was used in the subsequent step without further purification. MS (ESI) $(M+H)^+$=352.

23F: 1-(cyclopropylmethyl)-2-[(5-ethoxy-2-pyridinyl)methyl]-5-(1-pyrrolidinyl-carbonyl)-1H-benzimidazole.

Following the general procedure 20E, 1-(cyclopropylmethyl)-2-[(5-ethoxy-2-pyridinyl)methyl]-1H-benzimidazole-5-carboxylic acid (80 mg, 0.228 mmol) was dissolved in DMF (2 mL) and HATU (104 mg, 0.274 mmol) was added followed by DIPEA (48 µl, 0.274 mmol), After being stirred for 10 min, pyrrolidine was added and the resulting mixture was stirred overnight. The crude residue obtained after work-up was purified using reverse phase preparative HPLC to give a TFA salt as white solids (42 mg, 37%). $^1$H NMR (400 MHz, $CD_3OD$): δ 8.18 (d, J=2.8 Hz, 1H), 7.98 (d, J=9.2 Hz, 1H), 7.87 (s, 1H), 7.72 (dd, J=9.2 Hz, J=2.0 Hz, 1H), 7.52 (d, J=9.2 Hz, 1H), 7.46 (dd, J=9.2 Hz, J=2.8 Hz, 1H), 4.89 (s, 2H), 4.43 (d, J=6.8 Hz, 2H), 4.09 (q, J=7.2 Hz, 2H), 3.60 (t, J=7.6 Hz, 2H), 3.44 (t, J=7.6 Hz, 2H), 2.02–1.94 (m, 2H), 1.92–1.86 (m, 2H), 1.37 (t, J=7.2 Hz, 3H), 1.30–1.22 (m, 1H), 0.64– 0.58 (m, 2H), 0.48–0.44 (m, 2H). MS (ESI) $(M+H)^+$=405. Anal. Calcd for $C_{24}H_{28}N_4O_2 \cdot 0.8TFA \cdot 0.2H_2O$: C, 55.32; H, 5.12; N, 9.49. Found: C, 55.30; H, 4.91; N, 9.23.

Example 24

1-(Cyclopropylmethyl)-2-(4-ethoxybenzyl)-5-(4-morpholinylmethyl)-1H-benzimidazole 24A: 1-(cyclopropylmethyl)-2-(4-ethoxybenzyl)-1H-benzimidazole-5-carbaldehyde.

To a solution of 1-(cyclopropylmethyl)-2-(4-ethoxybenzyl)-1H-benzimidazole-5-carbonitrile (0.049 g, 0.149 mmol) in 50% aqueous formic acid (1 mL) was added a catalytic amount of Raney nickel (50% suspension in water) and the resulting mixture was heated at 90° C. for 6 hours. The mixture was filtered through a short pad of diatomaceous earth and washed with EtOAc. The solvent was evaporated in vacuo and the residue was taken up into EtOAc (5 mL). The organic phase was washed with 1 N NaOH (2×2 mL) and brine (2 mL), dried over $MgSO_4$, filtered, and concentrated in vacuo. The crude product was purified by silica gel column chromatography (40% EtOAc/hexanes) to provide the title compound (0.041 g, 82%) as a white solid. $^1$H NMR (acetone-$d_6$): δ 10.16 (s, 1H), 8.29 (s, 1H), 7.90 (d, J=8.4 Hz, 1H), 7.76 (d, J=8.4 Hz, 1H), 7.34 (d, J=8.4 Hz, 2H), 6.94 (d, J=8.4 Hz, 2H), 4.44 (s, 2H), 4.24 (d, J=6.4 Hz, 2H) 4.07 (q, J=6.8 Hz, 2H), 1.40 (t, J=7.0 Hz, 3H), 1.27–1.14 (m, 1H), 0.58–0.49 (m, 2H), 0.48–0.38 (m, 2H). MS (ESI) $(M+H)^+$=335.

24B: 1-(Cyclopropylmethyl)-2-(4-ethoxybenzyl)-5-(4-morpholinylmethyl)-1H-benzimidazole.

To a solution 1-(cyclopropylmethyl)-2-(4-ethoxybenzyl)-1H-benzimidazole-5-carbaldehyde (0.077 g, 0.231 mmol) and acetic acid (0.135 mL, 0.236 mmol) in tetrahydrofuran (THF) (0.25 mL) was added sodium triacetoxyborohydride (0.245 g, 0.268 mmol) and the resulting mixture was stirred at room temperature for 6 hours. Water (2 mL) and 1 N HCl (5 mL) were added and the mixture was stirred 10 minutes before being washed with EtOAc (2×5 mL). The aqueous layer was basified with 5 N NaOH (5 mL) and extracted with EtOAc (3×10 mL). The combined organic phases were washed with brine (5 mL), dried over $MgSO_4$, filtered, and concentrated in vacuo. The crude product was purified by silica gel column chromatography (5% MeOH/EtOAc) to provide the title compound (0.0445 g, 47%) which was dissolved in 1 M HCl in diethyl ether to provide, after evaporation of the solvent, the HCl salt an oil. $^1$H NMR (free base, $CDCl_3$): δ 7.68 (s, 1H), 7.28–7.23 (m, 2H), 7.14 (d, J=8.4 Hz, 2H), 6.81 (d, J=8.4 Hz, 2H), 4.26 (s, 2H), 3.98 (q, J=7.2 Hz, 2H), 3.88 (d, 6.4Hz, 2H), 3.72–3.65 (m, 4H) 3.63 (s, 2H), 2.53–2.44 (m, 4H), 1.38 (t, J=8.6 Hz, 3H), 1.07–1.00 (m, 1H), 0.53–0.48 (m, 2H), 0.29–0.22 (m, 2H). MS (ESI) $(M+H)^+$=406.

Example 25

1-[1-(cyclopropylmethyl)-2-(4-ethoxybenzyl)-1H-benzimidazol-5-yl]ethanone

25A: 1-[1-(cyclopropylmethyl)-2-(4-ethoxybenzyl)-1H-benzimidazol-5-yl]ethanol.

To a solution 1-(cyclopropylmethyl)-2-(4-ethoxybenzyl)-0.1H-benzimidazole-5-carbaldehyde (2.32 g, 6.94 mmol) in THF (60 mL) at 0° C. was added 3 M methyl magnesium bromide in THF (13.9 mL, 41.7 mmol) and the resulting mixture was stirred at 0° C. for 90 minutes. Water (50 mL) was added and the mixture was stirred 10 minutes before being extracted with EtOAc (3×100 mL). The combined organic phases were washed with brine (50 mL), dried over $MgSO_4$, filtered, and concentrated in vacuo: $CH_2Cl_2$ (5 mL) was added to the crude product, the resulting suspension was filtered, the solid was washed with $CH_2Cl_2$ (2 mL) and dried to provide the title compound (1.915 g, 79%) as a white solid. $^1$H NMR ($CDCl_3$): δ 7.74 (s, 1H), 7.31 (s, 2H), 7.12 (d, J=8.4 Hz, 2H), 6.79 (d, J=8.0 Hz, 2H), 5.03 (q, J=6.3 Hz, 2H), 4.27 (s, 2H), 3.98 (q, J=6.8 Hz, 2H) 3.90 (d, J=6.4 Hz, 2H), 2.33 (br s, 1H), 1.56 (d, J=6.4 Hz, 3H), 1.38 (t, J=7.0 Hz, 3H), 1.05–0.99 (m, 1H), 0.53–0.48 (m, 2H), 0.26–0.23 (m, 2H). MS (ESI) $(M+H)^+$=351. Anal. Calcd for $C_{22}H_{26}N_2O_2$: C, 75.40; H, 7.48; N, 7.99. Found: C, 75.22; H, 7.32; N, 7.99.

25B: 1-[1-(cyclopropylmethyl)-2-(4-ethoxybenzyl)-1H-benzimidazol-5-yl]ethanone.

To a mixture 1-[1-(cyclopropylmethyl)-2-(4-ethoxybenzyl)-1H-benzimidazol-5-yl]ethanol (1.35 g, 3.86 mmol), N-methylmorpholine-N-oxide (0.497 g, 4.24 mmol) and 4 Å molecular sieves (2.0 g) in $CH_2Cl_2$ (10 mL) was added tetrapropylammonium perruthenate (0.068 g, 0.193 mmol) and the resulting mixture was stirred at room temperature for 90 minutes. N-methylmorpholine-N-oxide (0.124 g, 1.06 mmol) and acetonitrile (1 mL) were added and the mixture was stirred at room temperature overnight. The solvent was concentrated in vacuo and the crude product was purified by silica gel column chromatography (30% EtOAc/hexanes to 60% EtOAc/hexanes) to provide the title compound (0.880 g, 65%) as a white solid. $^1$H NMR ($CDCl_3$): δ 8.34 (s, 1H), 7.94 (dd, J=8.4 Hz, J=2.0 Hz, 1H), 7.35 (d, J=8.4 Hz, 1H), 7.15 (d, J=8.4 Hz, 2H), 6.91 (dd, J=6.4 Hz, J=2.0 Hz, 2H), 4.29 (s, 2H), 3.98 (q, J=7.2 Hz, 2H) 3.41 (d, J=6.8 Hz, 2H), 2.67 (s, 3H), 1.38 (t, J=7.0 Hz, 3H), 1.07–1.00 (m, 1H), 0.55–0.51 (m, 2H), 0.29–0.26 (m, 2H). $^{13}$C NMR ($CDCl_3$): δ 198.71, 159.01, 156.43, 143.29, 140.01, 132.68, 130.44, 128.67, 123.50, 121.95, 115.83, 110.73, 64.38, 49.23, 34.63, 27.63, 15.76, 11.99, 5.20. MS (ESI) $(M+H)^+$=349. Anal. Calcd for $C_{22}H_{24}N_2O_2$+0.1H2O: C, 75.44, H, 6.96; N, 8.00. Found: C, 75.48; H, 7.13; N, 8.01.

Example 26

Methyl-1-(cyclopropylmethyl)-2-(4-ethoxybenzyl)-1H-benzimidazol-5-yl carbamate

26A: Methyl 4-fluoro-3-nitrophenylcarbamate.

To a stirred solution of 4-fluoro-3-nitro-aniline (10.30 g, 65.97 mmol), DIPEA (15.00 mL, 86.11 mmol) in $CH_2Cl_2$ (150 mL) was added dropwise methyl chloroformate (6.86 g, 72.59 mmol) at 0° C. The reaction was allowed to warm to room temperature and then stirred at room temperature overnight. The mixture was diluted with $CH_2Cl_2$ (100 mL), washed with 3 N HCl (50 mL), brine (20 mL), and dried over sodium sulfate. Removal of solvent afforded crude carbamate as light brown solid (13.03 g, 92%).

26B: Methyl 4-[(cyclopropylmethyl)amino]-3-nitrophenylcarbamate

Following general procedure 2B: To methyl 4-fluoro-3-nitrophenylcarbamate (6.50 g, 30.35 mmol, from previous step) in 80% aqueous ethanol (100 mL) was added cyclopropanemethylamine (5.00 mL, 57,65 mmol) at room temperature. The reaction mixture was heated at 60° C. overnight. After the usual work up, the crude product, which precipitated out, was collected (8.21 g). MS (ESI) $(M+H)^+$=266.

26C: Methyl 3-amino-4-[(cyclopropylmethyl)amino]phenylcarbamate.

Following general procedure 2C: methyl 4-[(cyclopropylmethyl)amino]-3-nitrophenylcarbamate (8.21 g) was hydrogenated in ethyl acetate (100 mL) catalyzed by 10% Pd/C (500 mg) at 15–25 psi $H_2$ for 1 h. The reaction mixture was filtered through diatomaceous earth, and removal of solvent gave the desired diamine (4.0 g, 56% for two steps). This material was used in the subsequent step without further purification. MS (ESI) $(M+H)^+$=236.

26D: Methyl-1-(cyclopropylmethyl)-2-(4-ethoxybenzyl)-1H-benzimidazol-5-ylcarbamate.

Following general procedure 13B: Methyl 3-amino-4-[(cyclopropylmethyl)amino]-phenylcarbamate (4.0 g, 17.0 mmol), DIPEA (5 mL), 4-ethoxyphenylacetic acid (3.06 g, 17.0 mmol) and HATU (7.10 g, 18.7 mmol) were combined. The desired product (3.34 g, 52%) precipitated out of the reaction mixture. $^1$HNMR (CDCl3): δ 7.65 (d, J=2.0 Hz, 1H), 7.37 (br., 1H), 7.26 (d, J=4 Hz), 7.12 (d, J=9.0 Hz, 2H), 6.81 (d, J=9.0 Hz, 2H), 6.74 (br., 1H), 4.25 (s, 2H), 3.98 (q, J=7.4 Hz, 2H), 3.87 (d, J=7.2 Hz, 2H), 3.79 (s, 3H), 1.38 (t, J=7.4 Hz, 3H), 1.05–0.97 (m, 1H), 0.52–0.47 (m, 2H), 0.25–0.20 (m, 2H). MS (ESI) $(M+H)^+$=380.

Example 27

N-[1-(cyclopropylmethyl)-[2-(4-ethoxybenzyl)-1H-benzimidazol-5-yl]-N,5-dimethyl-3-isoxazolecarboxamide

27A: 1-(cyclopropylmethyl)-2-(4-ethoxybenzyl)-N-methyl-1H-benzimidazol-5-amine.

Methyl-1-(cyclopropylmethyl)-2-(4-ethoxybenzyl)-1H-benzimidazol-5-ylcarbamate (1.65 g, 4.35 mmol) was added portionwise to a cold (0° C.) solution of $AlH_3$ (~0.3 M), which was freshly prepared by adding dropwise conc. $H_2SO_4$ (0.80 g, 8.10 mmol) to 1 M $LiAlH_4$ THF solution (16 ml, 16 mmol) in THF (30 mL) at 0° C. The reaction mixture was stirred at room temperature overnight, and subsequently quenched carefully by adding EtOAc (5 mL), $H_2O$ (3 mL) and $Et_2O$ (100 mL), and then $Na_2SO_4.5H_2O$ (10 g). The reaction mixture was stirred until a clear solution was produced, and the solid was filtered off. The filtrate was dried over $Na_2SO_4$ and concentrated in vacuo to afford desired compound (1.21 g). The crude product was used for next step without further purification.

27B: N-[1-(cyclopropylmethyl)-2-(4-ethoxybenzyl)-1H-benzimidazol-5-yl]-N,5-dimethyl-3-isoxazolecarboxamide.

To a solution of 1-(cyclopropylmethyl)-2-(4-ethoxybenzyl)-N-methyl-1H-benzimidazol-5-amine (100 mg, 0.30 mmol) and $Et_3N$ (200 mg, 0.20 mmol) in $CH_2Cl_2$ (5 mL) was added 5-methyl-3-isoxazolecarbonyl chloride (0.1 mL) at room temperature. The reaction mixture was stirred at room temperature overnight and quenched with saturated $NaHCO_3$ (1 mL). The mixture was diluted with $Et_2O$ (30 mL), washed with saturated $NaHCO_3$, and then brine, and finally dried over $Na_2SO_4$. Following concentration, the resulting residue was purified by preparative HPLC to give desired material as the TFA salt (40 mg, 24%). The TFA salt was dissolved in $H_2O$ (10 mL) and neutralized with saturated $NaHCO_3$, extracted with $Et_2O$ (2×20 mL). The combined ethereal solution was washed with brine, dried over $Na_2SO_4$, and concentrated. The free base was converted to its HCl salt (20 mg). $^1$HNMR ($CD_3OD$): δ 7.86 (br., 1H), 7.62 (br., 1H), 7.45 (br., 1H), 7.24 (d, J=8.4 Hz, 2H), 6.93 (d, J=8.4 Hz, 2H), 4.53 (s, 2H), 4.34 (d, J=6.8 Hz, 2H), 4.00 (q, J=7.0 Hz, 2H), 3.50 (s, 3H), 2.26 (s, 3H), 1.34 (t, J=7.0 Hz, 3H), 1.26–1.16 (m, 1H), 0.62–0.55 (m, 2M), 0.46–0.40 (m, 2H). MS (ESI) $(M+H)^+$=445. Anal. Calcd. for $C_{26}H_{28}N_4O_3.1.15HCl$: C, 64.19; H, 5.92; N, 11.51. Found: C, 64.59; H, 5.74; N, 10.97.

Example 28

Isopropyl-1-(cyclopropylmethyl)-2-(4-ethoxybenzyl)-1H-benzimidazol-5-yl-methyl)carbamate

To a solution of 1-(cyclopropylmethyl)-2-(4-ethoxybenzyl)-N-methyl-1H-benzimidazol-5-amine (67 mg, 0.20 mmol) and $Et_3N$ (0.1 mL) in $CH_2Cl_2$ (3 mL) was added isopropyl chloroformate (1 M in toluene, 0.24 mL, 0.24 mmol) at room temperature. The reaction mixture was stirred at room temperature overnight, and quenched with saturated NaHCO$_3$ (1 mL). The mixture was diluted with Et$_2$O (30 mL), washed with saturated NaHCO$_3$ and brine, dried over Na$_2$SO$_4$ and then concentrated. The resulting residue was purified by preparative HPLC to give TFA salt (10 mg, 9%). $^1$HNMR (CD$_3$OD): δ 7.87 (d, J=8.4 Hz, 1H), 7.62 (d, J=1.6 Hz, 1H), 7.50 (dd, J=1.6, 8.4 Hz, 1H), 7.24 (d, J=8.4 Hz, 2H), 6.93 (d, J=8.4 Hz, 2H), 4.95–4.85 (m, 1H), 4.54 (s, 2H), 4.35 (d, J=7.2 Hz, 2H), 4.01 (q, J=6.8 Hz, 2H), 3.31 (s, 3H), 1.343 (t, J=6.8 Hz, 3H), 1.27–1.19 (m, 1H), 1.19 (d, J=5.6 Hz, 6H), 0:63–0.56 (m, 2H), 0.47–0.42 (m, 2H). MS (ESI) (M+H)$^+$=422. Anal. Calcd. for C$_{25}$H$_3$]N$_3$O$_3$.1.35TFA.0.05H$_2$O: C, 57.72; H, 5.67; N, 7.29. Found: C, 57.68; H, 5.33; N, 7.23.

Example 29

(2S)-N-[1-(cyclopropylmethyl)-2-(4-ethoxybenzyl)-1H-benzimidazol-5-yl]-N,1-dimethyl-2-pyrrolidinecarboxamide To a stirred solution of 1-(cyclopropylmethyl)-2-(4-ethoxybenzyl)-N-methyl-1H-benzimidazol-5-amine (80 mg, 0.24 mmol) in DMF (3 ml) was added DIPEA (0.2 ml) and (2S)-1-methyl-2-pyrrolidinecarboxylic acid (80 mg, 0.62 mmol). The reaction mixture was stirred at room temperature for 5 min, and then HATU (280 mg, 0.73 mmol) was added. The reaction mixture was then stirred at room temperature overnight. Saturated NaHCO$_3$ (1 ml) and H$_2$O (20 ml) were added and the mixture was extracted with EtOAc (2×20 ml). The combined extracts were washed with saturated NaHCO$_3$ (5 ml) and brine, dried over Na$_2$SO$_4$, and concentrated in vacuo to give a crude amide which was purified by preparative HPLC to give its TFA salt (18 mg, 13%). MS (ESI) (M+H)$^+$=447.

Example 30

N'-tert-butyl-N-[1-(cyclopropylmethyl)-2-(4-ethoxybenzyl)-1H-benzimidazol-5-yl]-N-methylurea tert-Butylisocyanate (0.1 mL) was added to a solution of 1-(cyclopropylmethyl)-2-(4-ethoxybenzyl)-N-methyl-1H-benzimidazol-5-amine (34 mg, 0.10 mmol) in ethylene chloride (5 mL), and the reaction mixture was then heated at 60° C. overnight. The crude product was purified by flash chromatography on silica gel (EtOAc) to give desired urea (26 mg, 59%). $^1$HNMR (CDCl$_3$): Free base δ 7.61 (d, J=2.0 Hz, 1H), 7.33 (d, J=8.4 Hz, 1H), 7.16 (d, J=8.4 Hz, 2H), 7.10 (dd, J=2.0, 8.4 Hz, 1H), 6.83 (d, J=8.4 Hz, 2H), 4.28 (s, 1H), 4.27 (s, 2H), 4.00 (q; J=7.0 Hz, 2H), 3.93 (d, J=6.8 Hz, 2H), 3.26 (s, 3H), 1.40 (t, J=7.0 Hz, 3H), 1.28–1.20 (m, 1H), 1.25 (s, 9H), 0.58–0.53 (m, 2H), 0.31–0.26 (m, 2H). MS (ESI) (M+H)$^+$=435. The HCl salt was prepared using HCl in diethyl ether.

Anal. Calcd for C$_{26}$H$_{34}$N$_4$O$_2$.1.20HCl.1.10C$_2$H$_6$O: C, 64.03; H, 7.96; N, 10.59. Found: C, 64.10; H, 7.53; N, 10.30.

Example 31

N-[1-(Cyclopropylmethyl)2-(4-ethoxybenzyl)-1H-benzimidazol-5-yl]-N'-(2-methoxyphenyl)-N-methylthiourea 1-Isothiocyanato-2-methoxybenzene (100 mg, 0.61 mmol) was added to a solution of 1-(cyclopropylmethyl)-2-(4-ethoxybenzyl)-N-methyl-1H-benzimidazol-5-amine (100 mmol, 0.30 mmol) in DMF (5 mL). The reaction mixture was heated at 50° C. overnight. The crude product isolated following removal of the solvent was purified by chromatography on silica gel (EtOAc/CH$_2$Cl$_2$ 1:1) giving the desired product (85 mg, 57%) $^1$HNMR (CDCl$_3$): free base δ 8.26 (dd, J=2.0, 8.4 Hz, 1H), 7.74 (d, J=2.0 Hz, 1H), 7.50 (s, 1H), 7.43 (d, J=8.4 Hz, 1H), 7.20 (dd, J=1.6, 8.4 Hz, 1H), 7.15 (d, J=8.4 Hz, 2H), 7.08–7.02 (m, 1H), 6.98–6.92 (m, 1H), 6.83 (d, J=8.4 Hz, 2H), 6.75 (d, J=8.4 Hz, 1H), 4.29 (s, 2H), 4.00 (q, J=7.0 Hz, 2H), 3.96 (d, J=6.8 Hz, 2H), 3.80 (s, 3H), 3.58 (s, 3H), 1.37 (t, J=7.0 Hz, 3H), 1.10–1.00 (m, 1H), 0.59–0.52 (m, 2H), 0.32–0.25 (m, 2H). MS (ESI) (M+H)$^+$=501.

Example 32

N-Allyl-N-[1-(cyclopropylmethyl)-2-(4-ethoxybenzyl)-1H-benzimidazol-5-yl]acetamide 32A: N-(4-fluoro-3-nitrophenyl)acetamide 4-Fluoro-3-nitro-aniline (45.0 g) was added portionwise to acetic anhydride (150 mL) at room temperature. The reaction mixture was stirred at room temperature for 2 h. The desired product precipitated and it was collected and dried in vacuo (42.0 g, 70%).

32B: N-{4-[(cyclopropylmethyl)amino]-3-nitrophenyl}acetamide.

Following general procedure 2B: To a solution of N-(4-fluoro-3-nitrophenyl)acetamide (15.4 g, 77.7 mmol) in 80% aqueous ethanol (150 mL) was added cyclopropanemethylamine (10 mL) at room temperature. The reaction mixture was heated to reflux overnight. After cooling to room temperature, H$_2$O (300 mL) was added and the desired product precipitated out as an orange solid (18 g, 92%).

32C: N-{3-amino-4-[(cyclopropylmethyl)amino]phenyl}acetamide.

Following general procedure 2C: N-{4-[(cyclopropylmethyl)amino]-3-nitrophenyl}acetamide (7.0 g, 28 mmol) was hydrogenated in ethyl acetate (300 mL) with 10% Pd/C (0.8 g) at 25 psi H$_2$ in Parr shaker. After work up, isolated the desired product (5.5 g, 89%).

32D: N-[1-(cyclopropylmethyl)-2-(4-ethoxybenzyl)-1H-benzimidazol-5-yl]acetamide.

Following procedure 13B, N-{3-amino-4-[(cyclopropylmethyl)amino]phenyl}acetamide (5.50 g, 25.11 mmol), DIPEA (6.50 ml, 37.5 mmol), 4-ethoxyphenylacetic acid (5.40 g, 30.0 mmol) and HATU (11.40 g, 30.0 mmol) in DMF (100 ml) were stirred at room temperature overnight. Isolated the desired product (4.5 g, 86%).

$^1$HNMR (CD$_3$OD): δ 7.89 (s, 1H), 7.44–7.36 (m, 2H), 7.13 (d, J=8.4 Hz, 2H), 6.83 (d, J=8.4 Hz, 2H), 4.25 (s, 2H), 4.03–3.94 (m, 4H), 2.14 (s, 3H), 1.34 (t, J=7.0 Hz, 3H), 1.06–0.96 (m, 1H), 0.48–0.41 (m, 2H), 0.29–0.22 (m, 2H). MS (ESI) (M+H)$^+$=364. Anal. Calcd for C$_{22}$H$_{25}$N$_3$O$_2$.1.5H$_2$O: C, 67.67; H, 7.23; N, 10.76. Found: C, 67.50; H, 7.12; N, 10.65.

32E: N-allyl-N-[1-(cyclopropylmethyl)-2-(4-ethoxybenzyl)-1H-benzimidazol-5-yl]acetamide.

Allyl bromide (0.3 mL) was added to a well-stirred two phase solution of 50% KOH (5 mL), N-[1-(cyclopropylmethyl)-2-(4-ethoxybenzyl)-1H-benzimidazol-5-yl]acetamide (545 mg, 1.50 mmol) and n-Bu$_4$NBr (64 mg, 0.2 mmol) in CH$_2$Cl$_2$ (15 mL) at room temperature under nitrogen. The reaction mixture was stirred at room temperature for 2 h, and then diluted with H₂O (30 mL), extracted with CH₂Cl₂ (2×50 mL). The extracts were combined and washed with saturated NaHCO₃, brine, dried over Na₂SO₄. Removal of solvent gave a yellowish residue (530 mg) which was purified by flash chromatography on silica gel (MeOH/CH₂Cl₂, 1:10) to afford product (510 mg, 84%).

¹HNMR (CDCl₃): δ 7.54 (d, J=2.0 Hz, 1H), 7.31 (d, J=8.4 Hz, 1H), 7.16 (d, J=8.4 Hz, 2H), 7.02 (dd, J=2.0, 8.4 Hz, 1H), 6.84 (d, J=8.4 Hz, 2H), 45.98–5.84 (m, 1H), 5.12–5.04 (m, 2H), 4.34 (d, J=5.6 Hz, 2H), 4.27 (s, 2H), 4.01 (q, J=7.6 Hz, 2H), 3.93 (d, J=6.4 Hz, 2H), 1.88 (s, 3H), 1.39 (t, J=7.6 Hz, 3H), 1.10–1.00 (m, 1H), 0.59–0.52 (m, 2H), 0.31–0.26 (m, 2H). MS (ESI) (M+H)⁺=404. The HCl salt was prepared using HCl in diethyl ether. Anal. Calcd for C₂₅H₂₉N₃O₂.HCl.1.5H₂O: C, 64.24; H, 7.07; N, 8.99. Found: C, 63.96; H, 6.80; N, 8.84.

Example 33

N-Allyl-1-(cyclopropylmethyl)2-(4-ethoxybenzyl)-1H-benzimidazol-5-amine.

To a solution N-allyl-N-[1-(cyclopropylmethyl)-2-(4-ethoxybenzyl)-1H-benzimidazol-5-yl]acetamide (510 mg) in EtOH (20 mL) was added 20% KOH (20 mL). The reaction mixture was heated to reflux overnight, and then allowed to cool to room temperature. The mixture was concentrated in vacuo to around 20 mL, and extracted with CH₂Cl₂ (2×100 mL). The combined extracts were washed with brine, dried over Na₂SO₄ and concentrated in vacuo. The residue was purified by chromatography on silica gel (CH₂Cl₂:MeOH 25:1) to give light yellow oil (400 mg, 87%).

¹HNMR (CD₃OD): δ 8.03 (br., 1H), 7.64 (br., 1H), 7.54 (br., 1H), 7.28 (d, J=8.4 Hz, 2H), 6.96 (d, J=8.4 Hz, 2H), 6.03–5.92 (m, 1H), 5.43 (d, J=24.8 Hz, 1H), 5.40 (d, J=18.8 Hz, 1H), 4.59 (s, 2H), 4.41 (d, J=7.6 Hz, 2H), 4.04 (d, J=6.4 Hz, 2H), 4.03 (q, J=6.4 Hz, 2H), 1.36 (t, J=6.4 Hz, 3H), 1.30–1.18 (m, 1H), 0.66–0.58 (m, 2H), 0.50–0.42 (m, 2H). MS (ESI) (M+H)⁺=362. The HCl salt was prepared using HCl in diethyl ether. Anal. Calcd. For C₂₃H₂₇N₃O.2HCl.1.25H₂O: C, 60.46; H, 6.89; N, 9.19. Found: C, 60.53; H, 6.64; N, 8.89.

Example 34

1-[1-(cyclopropylmethyl)-2-(4-ethoxybenzyl)-1H-benzimidazol-5-yl]-2-pyrrolidinone 34A: 1-(Cyclopropylmethyl)-2-(4-ethoxybenzyl)-1H-benzimidazol-5-amine.

A solution of N-[1-(cyclopropylmethyl)-2-(4-ethoxybenzyl)-1H-benzimidazol-5-yl-acetamide (727 mg, 2 mmol) in 1:1 20% KOH:EtOH (20 mL) was stirred at reflux overnight. After being cooled, the mixture was acidified with 1 N HCl to pH~6.0, and the precipitate was collected by filtration to give the desired product as a pale yellow solid 611 mg (95%). MS (ESI) (M+H)⁺=322.

34B: 1-[1-(cyclopropylmethyl)-2-(4-ethoxybenzyl)-1H-benzimidazol-5-yl]-2-pyrrolidinone.

To 1-(Cyclopropylmethyl)-2-(4-ethoxybenzyl)-1H-benzimidazol-5-amine (72 mg, 0.22 mmol) and DIPEA (150 μL) in CH₂Cl₂ (3 mL) was added 4-bromobutyryl chloride (40 μL, 0.35 mmol). The reaction was stirred at room temperature for 3 h, then 50% KOH (3 mL) and n-Bu₄NBr (5 mg) were added to the reaction mixture. The reaction was vigorously stirred for 4 h, diluted with H₂O (10 mL), and extracted with CH₂Cl₂ (2×20 mL). The combined extracts were washed with H₂O, then brine, dried over Na₂SO₄, and concentrated in vacuo to give the crude lactam which was purified by preparative TLC, and subsequently by preparative. HPLC to afford desired products the TFA salt (11 mg, 10%). ¹HNMR(CD₃OD): δ 8.14 (d, J=2.0 Hz, 1H), 7.91 (d, J=9.2 Hz, 1H), 7.80 (dd, J=2.0, 9.2 Hz, 1H), 7.26 (d, J=9.2 Hz, 2H), 6.95 (d, J=9.2 Hz, 2H), 4.56 (s, 2H), 4.37 (d, J=6.4 Hz, 2H), 4.03 (t, J=7.6 Hz, 2H), 4.01 (q, J=6.8 Hz, 2H), 2.63 (t, J=8.4 Hz, 2H), 2.20 (tt, J=7.6, 8.4 Hz, 2H), 1.36 (t, J=6.8 Hz, 3H), 1.28–1.18 (m, 1H), 0.64–0.57 (m, 2H), 0.49–0.42 (m, 2H). MS (ESI) (M+H)⁺=390. Anal. Calcd for C₂₄H₂₇N₃O₂.TFA.0.1H₂O: C, 61.80; H, 5.63; N, 8.32. Found: C, 61.75; H, 5.30; N, 7.99.

Example 35

3-(Cyclopropylmethyl)-2-(4-ethoxybenzyl)-N,N-diethyl-3H-imidazo[4,5-b]pyridine-6-carboxamide 35A: 6-[(cyclopropylmethyl)amino]-5-nitronicotinic Acid.

Cyclopropanemethylamine (1.70 g, 23.90 mmol) was added to a solution of 6-chloro-5-nitronicotinic acid (1.12 g, 5.53 mmol) in MeOH (25 mL) at room temperature. The reaction mixture was stirred at room temperature for 2 h and concentrated in vacuo. The residue was dissolved in H₂O (20 mL), and the solution was acidified by adding 3N HCl until pH=3. The mixture was extracted with EtOAc and CH₂Cl₂ (2×100 mL) and the combined extracts were washed with brine, dried over Na₂SO₄, concentrated in vacuo to give a bright yellow solid (1.30 g) which was used in the following reaction without further purification.

35B: Methyl 6-[(cyclopropylmethyl)amino]-5-nitronicotinate.

6-[(cyclopropylmethyl)amino]-5-nitronicotinic acid (1.30 g) was dissolved in MeOH/toluene (1:1, 60 mL), and TMSCHN₂(2 M in hexane, 6 mL) was added dropwise. The reaction mixture was stirred at room temperature overnight, and concentrated in vacuo to give crude methyl ester (1.5 g) which was used for next step without purification.

35C: Methyl 5-amino-6-[(cyclopropylmethyl)amino]nicotinate.

Following general procedure 2C: Methyl 6-[(cyclopropylmethyl)amino]-5-nitronicotinate (1.5 g) was hydrogenated in ethyl acetate (50 mL) with 10% Pd/C (100 mg) at 20 psi H₂ in Parr shaker for 2 h. The reaction mixture was filtered through diatomaceous earth and the solvent removed to give the diamine (1.12 g) which was used without additional purification in the next step.

35D: Methyl 3-(cyclopropylmethyl)-2-(4-ethoxybenzyl)-3H-imidazo[4,5-b]pyridine-6-carboxylate.

Following general procedure 13B: Combined methyl 5-amino-6-[(cyclopropylmethyl)amino]nicotinate (950 mg, 4.3 mmol), DIPEA (1.1 ml), 4-ethoxyphenylacetic acid (850 mg, 4.72 mmol) and HATU (1.80, 4.74 mmol) in DMF (15 mL). The crude product was purified by flash chromatography on silica gel (EtOAc) to produce the desired product (530 mg, 34%).

¹HNMR (CDCl₃): δ 9.00 (d, J=2.0 Hz, 1H), 8.61 (d, J=2.0 Hz, 1H), 7.17 (d, J=8.0 Hz, 2H), 6.84 (d, J=8.0 Hz, 2H), 4.33 (s, 2H), 4.06 (d, J=7.2 Hz, 2H), 4.00 (q, J=7.0 Hz, 2H), 3.97 (s, 3H), 1.39 (t, J=7.0 Hz, 3H), 1.16–1.06 (m, 1H), 0.52–0.45 (m, 2H), 0.44–0.38 (m, 2H).

35E: 3-(cyclopropylmethyl)-2-(4-ethoxybenzyl)-3H-imidazo[4,5-b]pyridine-6-carboxylic acid.

To a solution of methyl 3-(cyclopropylmethyl)-2-(4-ethoxybenzyl)-3H-imidazo[4,5-b]pyridine-6-carboxylate (260 mg, 0.71 mmol) in THF/MeOH (1:1, 6 ml) was added 1 N NaOH (3 ml, 3 mmol). The reaction mixture was stirred at room temperature for 3 h, and concentrated in vacuo. The residue was dissolved in $H_2O$ (10 ml), and acidified by adding 1 N HCl solution to pH5. The solid was collected (230 mg), and the filtrate was extracted with EtOAc (2×50 ml). The extracts were dried over $Na_2SO_4$ and concentrated in vacuo to afford an additional crop of product (20 mg). The desired acid was produced in quantitative yield.

hu 1HNMR ($CD_3OD$): δ 8.93 (d, J=1.6 Hz, 1H), 8.50 (d, J=1.6 Hz, 1H), 7.15 (d, J=9.2 Hz, 2H), 6.82 (d, J=9.2 Hz, 2H), 4.33 (s, 2H), 4.11 (d, J=6.4 Hz, 2H), 3.95 (q, J=7.2 Hz, 2H), 1.31 (t, J=7.2 Hz, 3H), 1.16–1.03 (m, 1H), 0.43–0.32 (m, 4H).

35F: 3-(cyclopropylmethyl)-2-(4-ethoxybenzyl)-N,N-diethyl-3H-imidazo[4,5-b]pyridine-6-carboxamide.

To a stirred solution of 3-(cyclopropylmethyl)-2-(4-ethoxybenzyl)-3H-imidazo[4,5-b]pyridine-6-carboxylic acid (150 mg, 0.43 mmol) in DMF (5 ml) was added DIPEA (0.12 ml, 0.69 mmol) and diethylamine (60 μL, 0.58 mmol). The reaction mixture was stirred at room temperature for 5 min, and then HATU (200 mg, 0.53 mmol) was added. The reaction mixture was stirred at room temperature overnight and subsequently poured in ice water (20 ml) with stirring. The mixture was extracted with EtOAc (100 ml) and the extract was washed with $H_2O$ (20 ml), dried with $Na_2SO_4$, and concentrated in vacuo. The residue was purified by flash chromatography on silica gel (EtOAc/MeOH, 20:1) to give desired amide (115 mg, 64%) which was converted to the corresponding HCl salt using HCl in diethyl ether with methanol as co-solvent. $^1$HNMR ($CD_3OD$): δ 8.46 (d, J=2.0 Hz, 1H), 8.04 (d, J=2.0 Hz, 1H), 7.21 (d, J=8.4 Hz, 2H), 6.88 (d, J=8.4 Hz, 2H), 4.46 (s, 2H), 4.24 (d, J=7.2 Hz, 2H), 3.98 (q, J=7.0 Hz, 2H), 3.57 (br, 2H), 3.32 (br, 2H), 1.33 (t, J=7.0 Hz, 3H), 1.32–1.10 (m, 7H), 0.56–0.44 (m, 4H). MS (ESI) $(M+H)^+$=423. Anal. Calcd for $C_{24}H_{30}N_4O_2$·HCl·0.20$CH_3OH$: C, 64.68; H., 7.07; N, 12.48. Found: C, 65.07; H, 7.13; N, 12.13.

Example 36

N-Cyclopentyl-1-(cyclopropylmethyl)-2-(4-ethoxybenzyl)-1H-benzimidazole-5-sulfonamide 36A: 1-(Cyclopropylmethyl)-2-(4-ethoxybenzyl)-1H-benzimidazole-5-sulfonyl chloride.

To a mixture of conc. HCl (0.6 mL) and HOAc (0.18 mL) was added 1-(cyclopropylmethyl)-2-(4-ethoxybenzyl)-1H-benzimidazol-5-amine (193 mg, 0.6 mmol). The resulting mixture was stirred and cooled to <–10° C., and then a solution of $NaNO_2$ (44.8 mg, 0.65 mmol) in $H_2O$ (0.65 mL) was added slowly and the mixture was stirred between –10° C. and –5° C. for 45 min. In a separate flask, $SO_2$ was bubbled for 30 min into acetic acid (0.6 mL). CuCl (15 mg) was then added and more $SO_2$ was bubbled until the yellow-green suspension became blue-green. The mixture containing the copper was then cooled to <10° C., and the diazotization mixture was added dropwise with stirring. After all the diazonium salt were added, the mixture was poured into ice water (1:1, 4 mL) and then extracted with dichloromethane (3×15 mL), washed with $H_2O$ (2×10 mL), dried over $MgSO_4$ and concentrated to give an yellow oil (190 mg, 78%), which was used in the subsequent reaction soon after formation and without further purification. MS (ESI) $(M+H)^+$=405.

36B: N-Cyclopentyl-1-(cyclopropylmethyl)-2-(4-ethoxybenzyl)-1H-benzimidazole-5-sulfonamide.

To a crude solution of 1-(cyclopropylmethyl)-2-(4-ethoxybenzyl)-1H-benzimidazole-5-sulfonyl chloride (from 0.2 mmol of aniline precursor) in dichloromethane (4 mL) was added cyclopentyl amine (0.4 mmol) followed by pyridine (0.5 mL). The resulting mixture was stirred at room temperature overnight. Water (10 mL) was added and the mixture was extracted with $CH_2Cl_2$ (2×10 mL), dried over $MgSO_4$ and concentrated. The residue was purified by silica gel column chromatography to give the pure product which was treated with 1 M HCl solution in diethyl ether to form the HCl salt (62 mg, 81%). $^1$H NMR (400 MHz, $CD_3OD$): δ 8.29 (s, 1H), 7.78 (d, J=8.0 Hz, 1H), 7.42 (d, J=8.0 Hz, 1H), 7.16 (d, J=8.4 Hz, 2H), 6.84 (d, J=8.4 Hz, 2H), 4.32 (s, 2H), 4.02–3.94 (m, 4H), 3.62–3.58 (m, 1H), 1.80–1.74 (m, 2H), 1.64–1.56 (m, 2H), 1.50–1.42 (m, 2H), 1.39 (t, J=8.2 Hz, 3H), 1.42–1.34 (m, 2H), 1.08–1.00 (m, 1H), 0.58–0.54 (m, 2H), 0.30–0.25 (m, 2H). MS (ESI) $(M+H)^+$=454. Anal. Calcd for $C_{25}H_{31}N_3O_3S$·0.3HCl: C, 64.64; H, 6.79; N, 9.05. Found: C, 64.45; H, 6.97; N, 8.66.

Example 37

1-(Cyclopropylmethyl)-2-(4-ethoxybenzyl)-5-[(4-methyl-1-piperazinyl)sulfonyl]-1H-benzimidazole Following general procedure 36B: Used 1-(cyclopropylmethyl)-2-(4-ethoxybenzyl)-1H-benzimidazole-5-sulfonyl chloride (from 0.2 mmol of aniline precursor), 1-methylpiperazine (0.4 mmol) pyridine (0.5 mL) in $CH_2Cl_2$ (4 mL). The resulting mixture was stirred at room temperature overnight. Isolated the desired product as the HCl salt after column chromatography and treatment with 1 M HCl solution in diethyl ether (59 mg, 75%). $^1$H NMR (400 MHz, $CD_3OD$): δ 8.02 (s, 1H), 7.71 (d, J=8.6 Hz, 1H), 7.64 (d, J=8.6 Hz, 1H), 7.13 (d, J=8.8 Hz, 2H), 6.83 (d, J=8.8 Hz, 2H), 4.80 (s, 3H), 4.31 (s, 2H), 4.10 (d, J=7.2 Hz, 2H), 3.95 (q, J=8.0 Hz, 2H), 3.04–2.96 (m, 4H), 2.50–2.44 (m, 4H), 1.32 (t, J=8.0 Hz, 3H), 1.08–0.98 (m, 1H), 0.47–0.43 (m, 2H), 0.31–0.26 (m, 2H). MS (ESI) $(M+1)^+$: 469. Anal. Calcd for $C_{25}H_{32}N_4O_3S$·2.7HCl·0.4$H_2O$: C, 52.29; H, 6.23; N, 9.76. Found: C, 52.54; H, 6.21; N. 8.67.

Example 38

1-(Cyclopropylmethyl)-2-(4-ethoxybenzyl)-N-ethyl-1H-benzimidazole-5-sulfonamide

Following general procedure 36B: Used 1-(cyclopropylmethyl)-2-(4-ethoxybenzyl)-1H-benzimidazole-5-sulfonyl chloride (from 0.2 mmol of aniline precursor), ethyl amine (2M solution in THF, 0.4 mmol) and pyridine (0.5 mL) in $CH_2Cl_2$ (4 mL). The resulting mixture was stirred at room temperature overnight. Isolated the desired product as the HCl salt after column chromatography and treatment with 1 M HCl solution in diethyl ether (61 mg, 87%). $^1$H NMR (400 MHz, $CD_3OD$): δ 8.28 (s, 1H), 7.78 (d, J=8.0 Hz, 1H), 7.42 (d, J=8.0 Hz, 1H), 7.15 (d, J=8.8 Hz, 2H), 6.83 (d, J=8.8 Hz, 2H), 4.32 (s, 2H), 4.02–3.93 (m, 4H), 3.06–2.98 (m, 2H), 1.38 (t, J=7.6 Hz, 3H), 1.10 (t, J=8.0 Hz, 3H), 1.07–1.00 (m, 1H), 0.55–0.52 (m, 2H), 0.30–0.24 (m, 2H).

MS (ESI) (M+H)+=414. Anal. Calcd for $C_{12}H_{27}N_3O_3S.1.1HCl$: C, 58.25; H, 6.24; N, 9.26. Found: C, 58.19; H, 6.73; N, 8.62.

Example 39

2-(4-Ethoxyanilino)-N,N-diethyl-1-isopentyl-1H-benzimidazole-5-carboxamide

A solution of methyl 4-ethoxyphenyldithiocarbamate (0.0274 g, 0.121 mmol) in DMF (0.2 mL) was added to a mixture of 3-amino-N,N-diethyl-4-(isopentylamino)benzamide (0.0334 g, 0.120 mmol) and red mercury(II) oxide (0.0261 g, 0.121 mmol) in DMF (0.2 mL). The resulting suspension was stirred vigorously for 5.5 h, and an additional portion of red mercury(II) oxide (0.0130 g, 0.0600 mmol) was added. After stirring an additional 16 h, the reaction was diluted with 9:1 $CH_2Cl_2$:MeOH, loaded onto a small plug of silica gel, and eluted with the same solvent system. The eluant was concentrated, and the residue was purified by reverse phase HPLC (gradient 20–70% $CH_3CN$ in $H_2O$) to provide the title compound (0.0287 g, 45%) as its TFA salt. This material was lyophilized from $H_2O$/dioxane to produce a white solid. $^1$H-NMR ($CD_3OD$): δ 7.60 (d, J=8.4 Hz, 1H), 7.44–7.38 (2 overlapping d; 3H), 7.35 (s, 1H), 7.11 (d, J=9.2 Hz, 2H), 4.32 (br t, J=7.2 Hz, 2H), 4.12 (q, J=7.6 Hz, 2H), 3.56 (br s, 2H), 3.32 (br s, 2H), 1.85–1.76 (br m, 3H), 1.43 (t, 7.6 Hz, 3H), 1.25 (br s, 3H), 1.14 (br s, 3H), 1.08 (d, J=6.4 Hz, 6H). $^{13}$C-NMR($CD_3OD$): δ 172.51, 160.57, 151.15, 134.20, 132.87, 130.29, 128.70, 128.44, 123.46, 117.18, 111.54, 111.23, 65.02, 45.07, 43.16, 41.13, 37.49, 27.26, 22.76, 15.07, 14.35, 13.07. Anal. Calcd for MS (ESI) (M+H)+=423.

TABLE 2

Biological data on Examples 40–62.

| Ex. No | hCB2 IC$_{50}$ (nM) | hCB2 EC$_{50}$ (nM) | Emax (%) |
|---|---|---|---|
| 40 | 2.8 | 1.2 | 74 |
| 41 | 100 | 21 | 52 |
| 42 | 23 | 5 | 76 |
| 43 | 26 | 2.8 | 100 |
| 44 | 18 | 1.7 | 106 |
| 45 | 448 | 123 | 101 |
| 46 | 100 | 69 | 70 |
| 47 | 3.3 | 1.4 | 70 |
| 48 | 27 | 9 | 33 |
| 49 | 32 | 6.8 | 67 |
| 50 | 832 | — | — |
| 52 | 22 | 7.8 | 41 |
| 53 | 36 | 6.7 | 46 |
| 54 | 15.5 | 3.4 | 66 |
| 55 | 715 | — | — |
| 56 | 5.4 | 1.5 | 88 |
| 57 | 9.5 | 2.8 | 72 |
| 59 | 328 | 64 | 67 |
| 60 | 970 | — | — |
| 61 | Ki hCB2-Sf9 (n = 2): 11.4 | — | — |
| 62 | Ki hCB2-Sf9 (n = 2): 4.5 | — | — |

For Nos. 61 and 62, the $K_i$ has been measured from 2 compounds made in a plate.

Example 40

2-[(4-Ethoxyphenyl)methyl]-N,N-diethyl-1-(3-thienylmethyl)-1H-benzimidazole-5-carboxamide 40A: N,N-Diethyl-3-fluoro-4-nitro-benzamide 3-Fluoro-4-nitrobenzoic acid (5.0 g, 27.0 mmol) was refluxed in a mixture of 2:1 $CH_2Cl_2$/$SOCl_2$ (150 mL) overnight. The solvent was concentrated and the residue dissolved in $CH_2Cl_2$ (50 mL). Another $CH_2Cl_2$ solution (50 mL) of diethylamine (3.35 mL, 1.2 eq) and triethylamine (7.5 mL, 2 eq) was then added dropwise to the cold stirring solution (0° C.) of the acid chloride. The solution was stirred at rt for 1 h. The solution was then washed with 5% $KHSO_4$ solution, saturated $NaHCO_3$ solution, brine and dried over anhydrous $MgSO_4$. The crude product was purified by flash chromatography using 2:1/hex:EtOAc on silica gel to afford the title compound (5.10 g, 79% yield); $^1$H NMR (400 MHz, $CDCl_3$) δ 8.12 (m, 1H), 7.29 (m, 2H), 3.56 (br d, 2H), 3.23 (br d, 2H), 1.27 (br s, 3H), 1.15 (br s, 3H).

40B: 3-Amino-N,N-diethyl-4-nitro-benzamide

N,N-Diethyl-3-fluoro-4-nitro-benzamide (5.1 g, 21.2 mmol) was refluxed in a 2:1 mixture of $NH_4OH$/EtOH (150 mL) for 48 h. The solution was cooled to rt and the solvent concentrated. The solution was then extracted (3×) with EtOAc. The combined organic phases were washed with brine and dried over anhydrous $MgSO_4$. The crude product was crystallized from EtOAc/hexanes to give the title compound (4.35 g, 86% yield). $^1$H NMR (400 MHz, $CD_3OD$) δ 8.12 (d, J=8.8 Hz, 1H), 6.92 (s, 1H), 6.56 (d, J=8.8 Hz, 1H), 3.51 (q, J=7.2 Hz, 2H), 3.28 (m, 2H), 1.23 (t, J=7.2 Hz, 3H), 1.13 (t, J=7.2 Hz, 3H).

40C: N-[5-[(Diethylamino)carbonyl]-2-nitrophenyl]4-ethoxy-benzeneacetamide

To a stirring toluene solution (100 mL) of 3-amino-N,N-diethyl-4-nitro-benzamide (1.00 g, 4.21 mmol) were added 4-ethoxyphenylacetyl chloride (1.25 g, 1.5 eq) and zinc dust (415 mg, 1.5 eq). The solution was stirred at rt overnight. Another 0.5 eq of acid chloride and zinc dust were then added and the solution stirred at rt for another 24 h. The solution was then filtered through celite and rinsed with EtOAc. The organic phase was washed with saturated $NaHCO_3$ solution, brine and dried over anhydrous $MgSO_4$. The crude product was purified by flash chromatography using 1:1/hex:EtOAc on silica gel to furnish the desired product (1.52 g, 90% yield). $^1$H NMR (400 MHz, $CDCl_3$) d 8.81 (s, 1H), 8.20 (d, J=8.8 Hz, 1H), 7.26 (m, 3H), 7.15 (d, J=8.8 Hz, 1H), 6.94 (d, J=8.4 Hz, 2H), 4.06 (q, J=7.2 Hz, 2H), 3.75 (s, 2H), 3.54 (q, J=6.8 Hz, 2H), 3.24 (q, J=6.8 Hz, 2H), 1.59 (br s, 1H), 1.42 (t, J=6.8 Hz, 3H), 1.25 (t, J=6.8 Hz, 3H), 1.16 (t, J=6.8 Hz, 3H).

40D: N-[2-Amino-5-[(diethylamino)carbonyl]phenyl]-4-ethoxy-benzeneacetamide

N-[5-[(Diethylamino)carbonyl]-2-nitrophenyl]4-ethoxy-benzeneacetamide (1.00 g, 2.50 mmol) was dissolved in EtOAc (50 mL) containing a catalytic amount of 10% Pd/C. The solution was shaken under $H_2$ atmosphere (35 psi) at rt overnight. The solution was filtered through celite and the solvent was concentrated. LC/MS analysis showed that the title compound was pure enough (>95%) and could directly be used for next step. Yield: 927 mg (99%); $^1$HNMR (400 MHz, $CDCl_3$) δ 7.54 (s, 1H), 7.25 (d, J=7.6 Hz, 2H), 7.07 (s, 1H), 7.01 (d, J=8.0 Hz, 1H), 6.91 (d, J=7.2 Hz, 2H), 6.66 (d, J=8.4 Hz, 1H), 4.04 (q, J=6.8 Hz, 2H), 3.69 (s, 2H), 3.39 (br s, 4H), 1.42 (t, J=6.8 Hz, 3H), 1.15 (br s, 6H).

40E: 2-[(4-Ethoxyphenyl)methyl]-N,N-diethyl-1-(3-thienylmethyl)-1H-benzimidazole-5-carboxamide N-[2-Amino-5-[(diethylamino)carbonyl]phenyl]-4-ethoxy-benzeneacetamide (100 mg, 0.271 mmol) was dissolved in 3 mL of 2:1 mixture of DCE:AcOH. Thiophene-3-carboxaldehyde (37 mL, 1.5 eq) was added and the solution was stirred at rt for 15 min. The borane/pyridine complex solution (55 mL, 2 eq) was added and the solution was stirred at rt for 1 h. A few drops of concentrated HCl (5 drops) were added and the solution stirred at 85° C. for 3 h. The solution was cooled to rt and the solvent was concentrated. The crude product was directly purified by reversed-phase chromatography (C-18 column) using a gradient of 15–65% $CH_3CN/H_2O$ and then lyophilized. The title product was isolated as the corresponding TFA salt. Yield: 118 mg (78%). $^1$H NMR (400 MHz, $CD_3OD$) δ 7.78 (d, J=8.4 Hz, 1H), 7.70 (s, 1H), 7.48 (d, J=8.4 Hz 1H), 7.38 (m, 1H), 7.23 (s, 1H), 7.18 (d, J=7.2 Hz, 2H), 6.84 (m, 3H), 5.69 (s, 2H), 4.53 (s, 2H), 3.97 (q, J=7.2 Hz, 2H), 3.54 (br s, 2H), 3.27 (br s, 2H), 1.34 (t, J=7.2 Hz, 3H), 1.23 (br s, 3H), 1.10 (br s, 3H); MS (ESI) $(M+H)^+$=448.32; Anal. Calcd for $C_{26}H_{29}N_3O_2S$+1.7 TFA+0.1$H_2O$: C, 54.90; H, 4.84; N, 6.53. Found: C, 54.88; H, 4.86; N, 6.53.

Example 41

2-[(4-Ethoxyphenyl)methyl]-N,N-diethyl-1-[(2R)-2-pyrrolidinylmethyl]-1H-benzimidazole-5-carboxamide Following the procedure 40E using N-[2-Amino-5-[(diethylamino)carbonyl]phenyl]-4-ethoxy-benzeneacetamide (100 mg, 0.270 mmol) and N-(tert-butoxycarbonyl)-D-prolinal (76 mL, 1.5 eq). The crude product was directly purified by reversed-phase chromatography (C-18 column) using a gradient of 5–50% $CH_3CN/H_2O$ and then lyophilized. The title product was isolated as the corresponding TFA salt. Yield: 86 mg (78%). $^1$H NMR (400 MHz, $CD_3OD$) δ 7.94 (d, J=8.8 Hz, 1H), 7.70 (s, 1H), 7.55 (d, J=8.4 Hz, 1H), 7.28 (d, J=8.8 Hz, 2H), 6.94 (d, J=8.8 Hz, 2H), 4.83 (d, J=7.2 Hz, 2H), 4.55 (s, 2H), 4.02 (q, J=7.2 Hz, 2H), 3.96 (m, 1H), 3.56 (br s. 2H), 3.48 (m, 1H), 3.27 (m, 3H), 2.24 (m, 1H), 2.14 (m, 1H), 2.04 (m, 1H), 1.87 (m, 1H), 1.36 (t, J=7.2 Hz, 3H), 1.26 (br s, 3H), 1.11 (br s, 3H); MS (ESI) $(M+H)^+$=435.45; Anal. Calcd for $C_{26}H_{34}N_4O_2$+2.2 TFA+1.6$H_2O$: C, 51.12; H, 5.56; N, 7.84. Found: C, 51.12; H, 5.62; N, 7.82.

Example 42

2-[(4-Ethoxyphenyl)methyl]-N,N-diethyl-1-[[(2S-tetrahydro-2-furanyl]methyl]-1H-benzimidazole-5-carboxamide A mixture of N,N-diethyl-4-fluoro-3-nitrobenzamide (120 mg, 0.500 mmol), triethylamine (0.105 mL, 1.5 eq) and S-(+)-tetrahydrofurylamine (55 mg, 1.1 eq) were stirred in 3 mL of EtOH at 85° C. for 3 h. The solution was cooled to rt and the solvent concentrated. The residue was dissolved in EtOAc and washed with saturated $NaHCO_3$ solution, brine and dried over anhydrous $MgSO_4$. The adduct was purified by flash chromatography using 3:1/hex:EtOAc on silica gel. Yield: 147 mg (92%). $^1$H NMR (400 MHz, $CDCl_3$) δ 8.35 (s, 1H), 8.25 (s, 1H), 7.53 (d, J=8.8 Hz, 1H), 6.89 (d, J=8.8 Hz, 1H), 4.17 (m, 1H), 3.92 (m, 1H), 3.82 (m, 1H), 2.08 (m, 5H), 2.05 (m, 1H), 1.93 (m, 2H), 1.69 (m, 2H), 1.19 (t, J=6.8 Hz, 3H).

This nitro compound (125 mg, 0.389 mmol) was then dissolved in 20 mL of EtOAc containing a catalytic amount of 10% Pd/C. The solution was shaken under $H_2$ atmosphere (40 psi) at rt for 6 h. The solution was filtered through celite and the solvent concentrated to give the desired aniline. Yield: 113 mg (99%); MS (ESI) $(M+H)^+$=292.31.

This aniline (113 mg, 0.388 mmol) along with 4-ethoxyphenylacetyl chloride (85 mg, 1.1 eq) were stirred in 2 mL of dichloroethane at rt for 30 min. A few drops of concentrated HCl (5 drops) were added and the solution stirred at 85° C. for 3 h. The solution was cooled to rt and the solvent concentrated. The crude product was directly purified by reversed-phase chromatography (C-18 column) using a gradient of 15–65% $CH_3CN/H_2O$ and then lyophilized affording the title compound. The product was isolated as the corresponding TFA salt. Yield: 148 mg (69%); $^1$H NMR (400 MHz, $CD_3OD$) δ 7.99 (d, J=8.4 Hz, 1H), 7.68 (s, 1H), 7.58 (d, J=8.8 Hz, 1H), 7.28 (d, J=8.8 Hz, 2H), 6.97 (d, J=8.4 Hz, 2H), 4.70 (d, J=14.8 Hz, 1H), 4.60 (s, 2H), 4.51 (m, 1H), 4.21 (m, 1H), 4.02 (q, J=7.2 Hz, 2H), 3.89 (m, 1H), 3.73 (m, 1H), 3.57 (br d, 2H), 3.27 (br s, 2H), 2.18 (m, 1H), 1.97 (m, 2H), 1.76 (m, 1H), 1.36 (t, J=7.2 Hz, 3H), 1.26 (br s, 3H), 1.11 (br s, 3H); MS (ESI) $(M+H)^+$=436.43; Anal. Calcd for $C_{26}H_{33}N_3O_3$+2.5 TFA+0.4$H_2O$: C, 52.64; H, 5.23; N, 6.06. Found: C, 52.59; H, 5.08; N, 6.33.

Example 43

2-[(4-Ethoxyphenyl)methyl]-N,N-diethyl-1-[[(2R)-1-methyl-2-pyrrolidinyl]methyl]-1H-benzimidazole-5-carboxamide N-[2-Amino-5-[(diethylamino)carbonyl]phenyl]-4-ethoxy-benzeneacetamide (85 mg, 0.230 mmol) and N-(tert-butoxycarbonyl)-D-prolinal (0.06 mL, 1.5 eq) were coupled and cyclized following the procedure in example 40E. The solvent was then concentrated. The residue was dissolved in MeOH and 37% formaldehyde in water (formalin) (few drops, excess) was added, followed by sodium cyanoborohydride (43 mg, 3 eq). The solution was then stirred at rt for 1 h. The crude product was directly purified by reversed-phase chromatography (C-18 column) using a gradient of 15–65% $CH_3CN/H_2O$ and then lyophilized affording the title compound (46 mg, 36% yield) as the corresponding TFA salt; $^1$H NMR (400 MHz, $CD_3OD$) δ 7.80 (d, J=8.8 Hz, 1H), 7.69 (s, 1H), 7.48 (d, J=8.4 Hz, 1H), 7.22 (d, J=8.8 Hz, 2H), 6.92 (d, J=8.4 Hz, 2H), 4.85 (m, 1H), 4.66 (m, 1H), 4.49 (s, 2H), 4.01 (q, J=7.2 Hz, 2H), 3.78 (br s, 2H), 3.56 (br s, 2H), 3.27 (br s, 3H), 2.95 (s, 3H), 2.02 (m, 3H), 1.85 (m, 1H), 1.35 (t, J=7.2 Hz, 3H), 1.25 (br s, 3H), 1.11 (br s, 3H); MS (ESI) $(M+H)^+$=449.45; Anal. Calcd for $C_{27}H_{36}N_4O_2$+2.4 TFA+1.1$H_2O$: C, 51.47; H, 5.51; N, 7.55. Found: C, 51.46; H, 5.43; N, 7.67.

Examples 44 and 45

2-[(4-Ethoxyphenyl)methyl]-N,N-diethyl-1-[[(2R)-1-methyl-2-piperidinyl methyl]-1H-benzimidazole-5-carboxamide and 2-[(4-ethoxyphenyl)methyl]-N,N-diethyl-1-[[(2S)-1-methyl-2-piperidinyl]methyl]-1H-benzimidazole-5-carboxamide Following the procedure in example 40E. N-[2-Amino-5-[(diethylamino)carbonyl]phenyl]-4-ethoxy-benzeneacetamide (70 mg, 0.189 mmol) and 2-N-(tert-butoxycarbonyl)-1-piperidinecarboxaldehyde (52 mg, 1.5 eq). The crude product was then dissolved in MeOH (3 mL) containing a few drops of glacial acetic acid. An excess of 37% HCHO/H₂O was added followed by NaCNBH₃ (24 mg, 2 eq). The solution was stirred at rt for 30 min. The solvent was concentrated and the crude product was directly purified by reversed-phase chromatography (C-18 column) using a gradient of 5–50% CH₃CN/H₂O and then lyophilized affording the desired product as a mixture of two enantiomers. The product was isolated as the corresponding TFA salt. Yield: 53 mg (50%). The two enantiomers were separated by chiral chromatography using a Chiral AD column with an isocratic eluent of 30% iPrOH/hexanes containing 0.1% diethylamine to give the two enantiomers 2-[(4-ethoxyphenyl)methyl]-N, N-diethyl-1-[[(2R)-1-methyl-2-piperidinyl]methyl]-1H-benzimidazole-5-carboxamide (20 mg, 50%) and 2-[(4-ethoxyphenyl)methyl]-N,N-diethyl-1-[[(2S)-1-methyl-2-piperidinyl]methyl]-1H-benzimidazole-5-carboxamide (20 mg, 50%).

Enantiomer: 2-[(4-ethoxyphenyl)methyl]-N,N-diethyl-1-[[(2R)-1-methyl-2-piperidinyl]methyl]-1H-benzimidazole-5-carboxamide: $^1$H NMR (400 MHz, CD₃OD) δ 7.71 (br s, 1H), 7.68 (s, 1H), 7.43 (d, J=8.4 Hz, 1H), 7.21 (d, J=8.6 Hz, 2H), 6.92 (d, J=8.6 Hz, 2H), 4.85 (s, 2H), 4.42 (s, 2H), 3.97 (q, J=7.2 Hz, 2H), 3.55 (br s, 2H), 3.27 (m, 5H), 3.03 (s, 3H), 2.98 (br s, 1H), 1.85 (br s, 1H), 1.74 (m, 3H), 1.50 (br s, 1H), 1.34 (t, J=7.2 Hz, 3H), 1.25 (br s, 3H), 1.11 (br s, 3H). MS (ESI) (M+H)⁺=463.51; Anal. Calcd for $C_{28}H_{38}N_4O_2$+ 2.1TFA+0.6H₂O: C, 54.25; H, 5.84; N, 7.86. Found: C, 54.24; H, 5.69; N, 8.17. HPLC k': 1.99 (column: Chiral AD, gradient: 30% B in 25 min, flow 1 mL/min, 25° C.; Solvent A: 0.1% DEA in hexanes, Solvent B: 0.1% DEA in iPrOH).

Enantiomer: 2-[(4-ethoxyphenyl)methyl]-N,N-diethyl-1-[[(2S)-1-methyl-2-piperidinyl]methyl]-1H-benzimidazole-5-carboxamide: $^1$H NMR, MS and elemental analysis identical to its enantiomer; HPLC k': 4.97 (column: Chiral AD, gradient: 30% B in 25 min, flow 1 mL/min, 25° C.; Solvent A: 0.1% DEA in hexanes, Solvent B: 0.1% DEA in iPrOH).

Example 46

2-[(4-Ethoxyphenyl)hydroxymethyl]-N,N-diethyl-(3-methylbutyl)-1H-benzimidazole-5-carboxamide 2-(4-ethoxybenzoyl)-N,N-diethyl-1-(3-methylbutyl)-1H-benzimidazole-5-carboxamide (110 mg, 0.252 mmol) was dissolved in 3 mL of EtOH. NaBH₄ (12 mg, 1.2 eq) was added and the solution stirred at rt for 1 h. The solvent was concentrated and the residue dissolved in EtOAc. The organic phase was washed with saturated NaHCO₃ solution, brine and dried over anhydrous MgSO₄. The crude product was directly purified by reversed-phase chromatography (C-18 column) using a gradient of 10–65% CH₃CN/H₂O and then lyophilized affording the title compound. The product was isolated as the corresponding TFA salt. Yield: 102 mg (73%); $^1$H NMR (400 MHz, CD₃OD) δ 7.85 (br s, 2H), 7.62 (br s, 1H), 7.40 (br s, 2H), 7.01 (br s, 2H), 6.33 (br s, 1H), 4.29 (br s, 2H), 4.06 (br s, 2H), 3.62 (br s, 2H), 3.32 (br s, 2H), 1.55 (br, 2H), 1.38 (br s, 3H), 1.30 (br s, 3H), 1.17 (br s, 2H), 0.90 (s, 3H), 0.83 (s, 3H); MS (ESI) (M+H)⁺=438.30; Anal. Calcd for $C_{26}H_{35}N_3O_3$+1.2 TFA: C, 59.38; H, 6.35; N, 7.32. Found: C, 59.36; H, 5.97; N, 7.37.

Example 47

N-[2-[(4-Ethoxyphenyl)methyl]-1-(3-thienylmethyl) 1H-benzimidazol-5-yl]-N,3-dimethyl-butanamide 47A: Methyl (4-nitrophenyl)-carbamic acid, 1,1-dimethylethyl ester To a stirring solution of NaH (1.15 g, 1.5 eq, 60% in oil) in dry DMF (100 mL) was added a DMF solution (25 mL) of N-methyl-4-nitroaniline (3.00 g, 19.7 mmol) at 0° C. The solution was then stirred at 00° C. for 15 min. A DMF solution (50 mL) of di-tert-butyl dicarbonate (4.30 g, 1.2 eq) was then added and the solution was vigorously stirred at rt for 3 h. The solution was quenched by addition of saturated NH₄Cl solution and the solvent was concentrated. The residue was dissolved in EtOAc and washed with saturated NaHCO₃ solution, brine and dried over anhydrous MgSO₄. The crude product was purified by flash chromatography using 4:1/hex:EtOAc on silica gel to give 4.50 g (90% yield) of the desired product methyl(4-nitrophenyl)-carbamic acid, 1,1-dimethylethyl ester. $^1$H NMR (400 MHz, CDCl₃) δ 8.19 (d, J=8.8 Hz, 2H), 7.46 (d, J=8.8 Hz, 2H), 3.35 (s, 3H), 1.51 (s, 9H).

47B: (3-Amino-4-nitrophenyl)methyl-carbamic acid, 1,1-dimethylethyl ester

To a cold (0° C.) DMF solution (50 mL) of t-BuOK (9.0 g, 4.5 eq) and CuCl (176 mg, 0.1 eq) under N₂ was added a DMF (100 mL) solution of the methyl(4-nitrophenyl)-carbamic acid, 1,1-dimethylethyl ester (4:49 g, 17.8 mmol) and methoxylamine hydrochloride (1.85 g, 1.25 eq). The solution was let to warm up to rt over 1 h. The reaction mixture was then quenched with saturated NH₄Cl and the solvent was concentrated. The residue was diluted with water and extracted with EtOAc. The organic phase was washed with brine and dried over anhydrous MgSO₄. The crude product was purified by flash chromatography using 2:1/hex:EtOAc on silica gel to afford the desired product (3-Amino-4-nitrophenyl)methyl-carbamic acid, 1,1-dimethylethyl ester (1.10 g, 24% yield). $^1$H NMR (400 MHz, CDCl₃) δ 8.06 (d, J=9.2 Hz, 1H,), 6.78 (s, 1H), 6.67 (d, J=9.2 Hz 1H), 6.10 (br s, 2H), 3.28 (s, 3H), 1.50 (s, 9H).

47C: [3-[[(4-Ethoxyphenyl)acetyl]amino]-4-nitrophenyl] methyl-carbamic acid, 1,1-dimethylethyl ester To a stirring toluene solution (100 mL) of (3-Amino-4-nitrophenyl)methyl-carbamic acid, 1,1-dimethylethyl ester (1.10 g, 4.12 mmol) were added 4-ethoxyphenylacetyl chloride (980 mg, 1.2 eq) and zinc dust (400 mg, 1.5 eq). The solution was stirred at rt overnight. Another 0.5 eq of acid chloride and zinc dust were then added and the solution was stirred at rt for another 24 h. The solution was then filtered through celite and rinsed with EtOAc. The organic phase was washed with saturated NaHCO₃ solution, brine and dried over anhydrous MgSO₄. The crude product was purified by flash chromatography using 2:1/hex:EtOAc on silica gel to yield the desired product [3-[[(4-Ethoxyphenyl) acetyl]amino]-4-nitrophenyl]methyl-carbamic acid, 1,1-dimethylethyl ester (1.18 g, 67% yield); $^1$H NMR (400 MHz, CDCl₃) δ 8.77 (s, 1H), 8.11 (d, J=9.2 Hz, 1H), 7.22 (m, 3H), 6.93 (d, J=9.2 Hz, 2H), 4.40 (m, 2H), 3.75 (s, 2H), 3.33 (s, 3H), 1.50 (s, 9H), 1.42 (t, J=6.8 Hz, 3H).

47D: 4-Ethoxy-N-[5-(methylamino)-2-nitrophenyl]-benzeneacetamide

[3-[[(4-Ethoxyphenyl)acetyl]amino]-4-nitrophenyl]methyl-carbamic acid, 1,1-dimethylethyl ester (1.10 g, 2.56 mmol) was stirred in 15 mL of 1 M HCl/AcOH at rt for 2 h. The solvent was concentrated. The residue was dissolved in EtOAc and washed with saturated NaHCO₃ solution, brine and dried over anhydrous MgSO₄. The product was directly used for the next step. Yield 845 mg (99%); ¹H NMR (400 MHz, CDCl₃) δ 8.80 (d, 3=9.2 Hz, 1H), 8.02 (s, 1H), 7.25 (d, J=6.8 Hz, 2H), 6.91 (d, J=8.4 Hz, 2H), 6.22 (d, J=9.2 Hz, 1H), 4.74 (br d, 1H), 4.04 (q, J=7.2 Hz, 2H), 3.73 (s, 2H), 2.94 (s, 3H), 1.41 (t, J=7.2 Hz, 3H).

47E: 4-Ethoxy-N-[5-[methyl(3-methyl-1-oxobutyl)amino]-2-nitrophenyl]-benzeneacetamide To a 1:1/DCE:CH₃CN solution (50 mL) of 4-ethoxy-N-[5-(methylamino)-2-nitrophenyl]-benzeneacetamide (845 mg, 2.56 mmol) and DMAP (470 mg, 1.5 eq) was added isovaleryl chloride (0.47 mL, 1.5 eq). The solution was stirred at rt for 48 h. The solution was then washed with 5% KHSO₄, saturated NaHCO₃ solution, brine and dried over anhydrous MgSO₄. The crude product was purified by flash chromatography using 7:1/CH₂Cl₂:ether to give the desired product 4-ethoxy-N-[5-[methyl(3-methyl-1-oxobutyl)amino]-2-nitrophenyl]-benzeneacetamide (1.06 g, 99% yield); ¹H NMR (400 MHz, CDCl₃) δ 8.72 (s, 1H), 8.21 (d, J=8.8 Hz, 1H), 7.26 (m, 3H), 6.96 (m, 2H), 4.06 (m, 2H), 3.76 (s, 2H), 3.31 (s, 3H), 2.15 (m, 3H), 1.42 (t, J=7.2 Hz, 3H), 0.88 (d, J=6.8 Hz, 6H).

47F: 4-Ethoxy-N-[2-amino-5-[methyl(3-methyl-1-oxobutyl)amino]phenyl]-benzeneacetamide 4-Ethoxy-N-[5-[methyl(3-methyl-1-oxobutyl)amino]-2-nitrophenyl]-benzeneacetamide (1.05 g, 2.53 mmol) was dissolved in EtOAc (50 mL) containing a catalytic amount of 10% Pd/C. The solution was shaken under H₂ atmosphere (35 psi) at rt overnight. The solution was filtered through celite and the solvent concentrated. LC/MS analysis showed that title compound was pure (>95%) and could directly be used for next step. Yield: 965 mg (99%). ¹H NMR (400 MHz, CDCl₃) δ 7.23 (d, J=8.8 Hz, 2H), 7.12 (s, 1H), 7.00 (s, 1H), 6.93 (d, J=8.8 Hz, 1H), 6.78 (m, 2H), 4.01 (q, J=7.0 Hz, 2H), 3.69 (s, 2H), 3.13 (s, 3H), 2.05 (m, 1H), 1.93 (d, J=7.2 Hz, 2H), 1.39 (t, J=7.2 Hz, 3H), 0.78 (d, J=6.8 Hz, 6H).

47G: N-[2-[(4-Ethoxyphenyl)methyl]-1-(3-thienylmethyl)-1H-benzimidazol-5-yl]-N,3-dimethyl-butanamide Following the procedure in example 40E using 4-ethoxy-N-[2-amino-5-[methyl(3-methyl-1-oxobutyl)amino]phenyl]-benzeneacetamide (75 mg, 0.196 mmol) and thiophene-3-carboxaldehyde (26 mL, 1.5 eq). The crude product was directly purified by reversed-phase chromatography (C-18 column) using a gradient of 15–65% CH₃CN/H₂O and then lyophilized. The title compound was isolated as the corresponding TFA salt. Yield: 55 mg (50%); ¹H NMR (400 MHz, CD₃OD) δ 7.54 (m, 2H), 7.30 (d, J=4.8 Hz, 1H), 7.17 (d, J=8.4 Hz, 1H), 7.12 (d, J=8.4 Hz, 1H), 7.05 (s, 1H), 6.80 (d, J=8.8 Hz, 2H), 6.70 (d, J=5.2 Hz, 1H), 5.48 (s, 2H), 4.35 (s, 2H), 3.95 (q, J=7.2 Hz, 2H), 3.23 (s, 3H), 2.03 (br s, 1H), 1.94 (br s, 2H), 1.31 (t, J=7.2 Hz, 3H), 0.76 (br s, 6H); MS (ESI) (M+H)⁺=462.43; Anal. Calcd for C₂₇H₃₁N₃O₂S+0.7 TFA+0.5H₂O: C, 61.97; H, 5.99; N, 7.63. Found: C, 61.88; H, 6.03; N, 7.62.

Example 48

N-[2-[(4-Ethoxyphenyl)methyl]-1-[(2R)-2-pyrrolidinylmethyl]-1H-benzimidazol-5-yl]-N,3-dimethyl-butanamide Following the procedure in example 40E using 4-ethoxy-N-[2-amino-5-[methyl(3-methyl-1-oxobutyl)amino]phenyl]-benzeneacetamide (75 mg, 0.196 mmol) and N-(tert-butoxycarbonyl)-D-prolinal (55 mL, 1.5 eq). The crude product was directly purified by reversed-phase chromatography (C-18 column) using a gradient of 5–50% CH₃CN/H₂O and then lyophilized. The title compound was isolated as the corresponding TFA salt. Yield: 81 mg (73%); ¹H NMR (CD₃OD) δ 7.91 (d, J=8.8 Hz, 1H), 7.59 (s, 1H), 7.43 (d, J=8.8 Hz, 1H), 7.26 (d, J=8.8 Hz, 2H), 6.93 (d, J=8.8 Hz, 2H), 4.79 (d, J=7.2 Hz, 2H), 4.53 (s, 2H), 3.98 (q, J=7.2 Hz, 2H), 3.88 (m, 1H), 3.44 (m, 1H), 3.23 (s, 3H), 2.18 (m, 1H), 2.13 (m, 1H), 2.05 (m, 2H), 1.98 (m, 3H), 1.81 (m, 1H), 1.33 (t, J=7.2 Hz, 3H), 0.78 (br s, 6H); MS (ESI) (M+H)⁺=449.50; Anal. Calcd for C₂₇H₃₆N₄O₂+2.3 TFA+1.8H₂O: C, 51.06; H, 5.68; N, 7.54. Found: C, 51.06; H, 5.73; N, 7.26.

Example 49

N-[1-[[5-[(Acetyloxy)methyl]-2-furanyl]methyl]-2-[(4-ethoxyphenyl)methyl]-1H-benzimidazol-5-yl]-N,3-dimethyl-butanamide Following the procedure in example 40E. Using 4-ethoxy-N-[2-amino-5-[methyl(3-methyl-1-oxobutyl)amino]phenyl]-benzeneacetamide (75 mg, 0.196 mmol) and 5-[(acetyloxy)methyl]-2-furancarboxaldehyde (50 mg, 1.5 eq). The crude product was directly purified by reversed-phase chromatography (C-18 column) using a gradient of 15–65% CH₃CN/H₂O and then lyophilized. The title compound was isolated as the corresponding TFA salt. Yield: 63 mg (51%); ¹H NMR (400 MHz, CD₃OD) δ 8.01 (d, J=8.8 Hz, 1H), 7.64 (s, 1H), 7.49 (d, J=8.8 Hz, 1H), 7.27 (d, J=8.4 Hz, 2H), 6.94 (d, J=8.4 Hz, 2H), 6.50 (d, J=3.2 Hz, 1H), 6.39 (d, J=3.2 Hz, 1H), 5.75 (s, 2H), 4.92 (s, 2H), 4.68 (s, 2H), 4.00 (q, J=7.2 Hz, 2H), 3.27 (s, 3H), 2.02 (m, 1H), 1.96 (br s, 5H), 1.36 (t, J=7.2 Hz, 3H), 0.79 (s, 6H); MS (ESI) (M+H)⁺=518.49; Anal. Calcd for C₃₀H₃₅N₃O₅+1.6TFA+0.6H₂O: C, 56.10; H. 5.36; N, 5.91. Found: C, 56.14; H, 5.40; N, 5.95.

Example 50

N-[2-(Ethoxybenzyl)-1-[(2S)-2-pyrrolidinylmethyl]-1H-benzimidazol-5-yl]-N'-N-(1-isopropyl)urea 50A: N-[5-[methyl[[isopropylamino]carbonyl]amino]-2-nitrophenyl]4-ethoxy-benzeneacetamide A mixture of 4-ethoxy-N-[5-(methylamino)-2-nitrophenyl]-benzeneacetamide (2.20 g, 6.69 mmol) in 1,2-dichloroethane (100 mL) was stirred at room temperature under nitrogen as triphosgene (1.99 g, 6.69 mmol) and TEA (0.93 mL, 6.69 mmol) were added. After 30 minutes, DMAP (817 mg, 6.69 mmol), and isopropylamine (3.42 mL, 40.0 mmol) were added, and the contents were stirred for 16 hours at 45° C. The mixture was quenched with saturated aqueous NaHCO₃ (40 m L) and the layers were separated. The aqueous phase was extracted with dichloromethane (2×50 mL) and the organic layers were combined and washed with brine (50 mL), and dried with Na₂SO₄. The solids were filtered off and the filtrate concentrated in vacuo to a residue which was purified by column chromatography (75% EtOAc, 25% heptane on silica gel) to give the title compound (2.44 g, 88%), ¹HNMR (400 MHz, CDCl₃): δ 1.14 (d, J=6.4, 6H), 1.38 (t, J=7.1 Hz, 3H), 3.29 (s, 3H), 3.71 (s, 2H), 4.01 (q, J=7:1 Hz, 2H), 4.70 (s, 1H), 6.90 (d, J=8.8 Hz, 2H), 7.00 (dd, J=2.5, 9.2 Hz, 1H), 7.22 (d, J=8.8 Hz, 2H), 8.13 (d, J=9.2 Hz, 1H), 8.61 (d, J=2.5 Hz, 1H). MS (ESI) (M+H)$^+$ =415.

50B: N-[2-amino-5-[methyl[[isopropylamino]carbonyl] amino]phenyl]-4-ethoxy-benzeneacetamide A mixture of N-[5-[methyl[[isopropylamino]carbonyl] amino]-2-nitrophenyl]4-ethoxy-benzeneacetamide (190 mg, 0.46 mmol) and 10% Pd/C in EtOAc (5.0 mL) was hydrogenated for 4 hours at 30 psi. The contents were filtered through Celite, and the Celite was washed with EtOAc (2×10.0 mL). The solvent was removed in vacuo to provide the title compound (170 mg, 99%), which was used without further purification. $^1$HNMR (400 MHz, CDCl$_3$): δ 0.98 (d, J=6.5 Hz, 6H), 1.38 (t, J=7.1 Hz, 3H), 3.09 (s, 3H), 3.69 (s, 2H), 3.86 (spt, J=6.7 Hz, 1H), 3.99 (q, J=7.0 Hz, 2H), 4.11–4.13 (m, 1H), 6.71 (d, J=8.4 Hz, 1H), 6.82 (dd, J=2.4 Hz, J=8.4 Hz, 1H), 6.87 (d, J=8.6 Hz, 2H), 6.96 (d, J=2.3 Hz, 1H), 7.24 (d, J=8.6 Hz, 2H), 7.58 (s, 1H). MS (ESI) (M+H)$^+$=385.

50C: N-[2-(4-ethoxybenzyl)-1-[(2S)-2-pyrrolidinylmethyl]-1H-benzimidazol-5-yl]-N'-N-(1-isopropyl)urea Following the procedure in example 40E. A mixture of N-[2-amino-5-[methyl[[isopropylamino]carbonyl]amino] phenyl]-4-ethoxy-benzeneacetamide (83 mg, 0.22 mmol) and 2-(S)-N-Boc-prolinal (56 μL, 0.30 mmol) in a mixture of 1,2 dichloroethane/AcOH (2:1, 7.5 mL) was stirred at room temperature for 2.5 hours. BH$_3$. pyridine complex (43 μL, 0.42 mmol) was added via syringe and the contents were stirred for 16 hours. The mixture was heated to reflux for 6 hours. Usual work up gave a residue which was purified by reverse phase high pressure liquid chromatography (HPLC, C-18 column) to give the title compound as a trifluoroacetic acid (TFA) salt (25 mg, 26%). $^1$HNMR (400 MHz, MeOH-d$_4$): δ 1.08 (d, J=6.6 Hz, 6H), 1.36 (t, J=6.9 Hz, 3H), 1.75–1.85 (m, 1H), 1.96–2.05 (m, 1H), 2.10–2.20 (m, 2H), 3.26 (s, 3H), 3.44 (m, 1H), 3.85–3.93 (m, 2H), 4.01 (q, J=7.1 Hz, 2H), 4.47 (s, 2H), 4.70 (d, J=7.2 Hz, 2H), 6.93 (d, J=8.6 Hz, 2H), 7.24 (d, J=8.6 Hz, 2H), 7.38 (dd, J=2.0, J=8.8 Hz, 1H), 7.57 (d, J=2.0 Hz), 7.77 (d, J=8.6 Hz). MS (ESI) (M+H)$^+$=450.

Example 51

1-(Cyclopropylmethyl)-2-[1-(4-ethoxyphenyl)ethyl]-N-methyl-1H-benzimidazol-5-amine Method A:

51AA: 1-(cyclopropylmethyl)-2-[(4-ethoxyphenyl)methyl]-N-methyl-1H-benzimidazol-5-amine To a suspension of methyl [1-(cyclopropylmethyl)-2-[(4-ethoxyphenyl)methyl]-1H-benzimidazol-5-yl]carbamate (0.781 g, 2.06 mmol) in THF was added LAH (0.32 g, 8.43 mmol) at 0° C. The mixture was stirred for 1 h at 0° C. and 2.5 h at reflux, cooled town to −78° C., and quenched with MeOH (5 mL) and H$_2$O (5 mL). After adding Na$_2$SO$_4$ (10 g), the resulting mixture was stirred for 1 h at room temperature. After filtration and concentration, the residue was purified by MPLC using EtOAc on silica gel to give 641.7 mg (93%) of the title compound as an off-white solid. $^1$HNMR (CDCl$_3$): δ 0.22 (m, 2H), 0.48 (m, 2H), 1.26 (m, 1H), 1.38 (t, J=7.0 Hz, 3H), 2.89 (s, 3H), 3.83 (d, J=6.6 Hz, 2H), 3.98 (q, J=7.0 Hz, 2H), 4.23 (s, 2H), 6.64 (dd, J=8.6, 2.2 Hz, 1H), 6.80 (d, J=8.6 Hz, 2H), 6.99 (d, J=2.1 Hz, 1H), 7.13 (m, 3H). MS (ESI) (M+H)$^+$=336.42.

51AB: 1,1-dimethylethyl [1-(cyclopropylmethyl)-2-[(4-ethoxyphenyl)methyl]-1H-benzimidazol-5-yl]methyl carbamate A solution of 1-(cyclopropylmethyl)-2-[(4-ethoxyphenyl) methyl]-N-methyl-1H-benzimidazol-5-amine (816.9 mg, 2.44 mol) and Boc$_2$O (930.1 mg, 4.26 mmol) in THF (60 mL) was stirred over weekend at room temperature. Upon evaporation of the solvent, the residue was purified by MPLC using Hex/EtOAc (1:1) on silica gel to give 917.7 mg (87%) of the title compound as a white solid. MS (ESI) (M+H)$^+$=436.49.

51AC: 1,1-dimethylethyl,[1-(cyclopropylmethyl)-2-[1-(4-ethoxyphenyl)ethyl]-1H-benzimidazol-5-yl]methyl carbamate To a solution of 1,1-dimethylethyl [1-(cyclopropylmethyl)-2-[(4-ethoxyphenyl)methyl]-1H-benzimidazol-5-yl] methyl carbamate (654.3 mg, 1.50 mmol) in THF was added KHMDS (0.5 M, 4 mL, 2.0 mmol) at −78° C. After stirring for 40 min, MeI (283.9 mg, 2.0 mmol) was added. The mixture was stirred overnight at room temperature, quenched with MeOH (0.5 mL) and sat. NaHCO$_3$ (10 mL). Two phases were separated. The aqueous was extracted with EtOAc (3×30 ml). The combined organic phases were washed with brine (2×30 mL) and dried with Na$_2$SO$_4$. After concentration, the residue was purified by MPLC using Hex/EtOAc (1:1) on silica gel to give 541.3 mg (80%) of the desired product as a yellow syrup. MS (ESI) (N+H)$^+$ =450.44

51AD: 1-(cyclopropylmethyl)-2-[1-(4-ethoxyphenyl)ethyl]-N-methyl-1H-benzimidazol-5-amine A mixture of 1,1-dimethylethyl, [1-(cyclopropylmethyl)-2-[1-(4-ethoxyphenyl)ethyl]-1H-benzimidazol-5-yl]methyl carbamate (541.3 mg, 1.20 mmol) in 4N HCl/dioxane (20 mL) was stirred for 2.5 h at room temperature. Upon evaporation of the solvent, the residue was dissolved in water (30 mL), neutralized with 2 N NaOH and extracted with EtOAc (4×30 mL). The combined organic phases were washed with sat. NaHCO$_3$ and dried over Na$_2$SO$_4$. After filtration and concentration, 523.0 mg (100%) of the title compound as a syrup was obtained. MS (ESI) (M+H)$^+$ =350.35.

Method B:

51BA: Ethyl 4-ethoxyphenyl-2-propionate

To a solution of 4-hydroxyphenyl-2-propionic acid (5.83 g, 35.1 mmol) in DMF (100 mL) was added K$_2$CO$_3$ (12.12 g, 87.7 mmol) at 0° C. After stirring for 1 h, EtI (7.0 mL, 13.68 g, 87.7 mmol) was added. The mixture was stirred over weekend at room temperature which was diluted with water (400 mL) and extracted with EtOAc (4×100 mL). The combined organic phases were washed with water (2×100 mL) and brine (100 mL), and dried with Na$_2$SO$_4$. Upon filtration and concentration, the residue was purified by MPLC using Hex/EtOAc (4:1) on silica gel to give 7.61 g (98%) of the title compound as a colorless liquid. $^1$H-NMR (400 MHz, CDCl$_3$): δ 1.18 (t, J=7.2 Hz, 3H), 1.38 (t, J=7.0 Hz, 3H), 1.44 (d, J=7.0 Hz, 3H), 3.62 (q, J=7.0 Hz, 2H), 3.99 (q, J=7.1 Hz, 2H), 4.1 (m, 1H), 6.8 (m, 2H), 7.2 (m, 2H).

51BB: 4-ethoxyphenyl-2-propionic acid

To a solution of ethyl 4-ethoxyphenyl-2-propionate (1.33 g, 5.98 mmol) in 30 mL of THF-H$_2$O (7:3) was added LiOH (0.29 g, 12.0 mmol). The mixture was heated for 24 h at 40°

C., and diluted with water (20 mL). The aqueous phase was extracted with ether, acidified with 2 N HCl and then extracted with ether (4×20 mL). The combined organic phases were washed with brine and dried with $Na_2SO_4$. After filtration and concentration, 1.14 g (98%) of the title compound as a white solid was obtained. $^1$H-NMR (400 MHz, $CDCl_3$): δ 1.38 (t, J=7.0 Hz, 3H), 1.47 (d, J=7.2 Hz, 3H), 3.66 (q, J=7.2 Hz, 1H), 3.99 (q, J=7.0 Hz, 2H), 6.8 (m, 2H), 7.2 (m, 2H).

51 BC: N-[1-(cyclopropylmethyl)-2-[1-(4-ethoxyphenyl) ethyl]-1H-benzimidazol-5-yl]acetamide To a solution of N-[3-amino-4-[(cyclopropylmethyl) amino]phenyl]acetamide (1.28 g, 5.82 mmol) and 4-ethoxyphenyl-2-propionic acid (1.13 g, 5.82 mmol) in DMF (40 mL) was added DIPEA (1.52 mL, 1.13 g, 8.73 mmol) at room temperature. After stirring for 10 min, HATU (2.66 g, 6.98 mmol) was added in one portion. The mixture was stirred overnight at room temperature, concentrated to a small volume (10 mL), followed by addition of $H_2O$ (100 mL), which was extracted with EtOAC (4×50 mL). The combined organic phases were washed with brine and dried with $Na_2SO_4$. Upon filtration and evaporation, the residue was dissolved in acetic acid (40 mL) and then heated for 20 h at 100° C. After evaporation of the solvent, the residue was dissolved in EtOAc (200 mL), and washed with 10% $Na_2CO_3$ and dried with $Na_2SO_4$. After concentration, the crude product was purified by MPLC using EtOAc to give 2.14 g (97%) of the title compound as a light yellow solid. $^1$H-NMR (400 MHz, $CDCl_3$): d 0.11 (m, 1H), 0.27 (m, 1H), 0.47 (m, 2H), 0.94 (m, 1H), 1.38 (t, J=7.0 Hz, 3H), 1.81 (d, J=7.0 Hz, 3H), 2.21 (s, 3H), 3.76 (dd, J=15.0, 6.8 Hz, 1H), 3.86 (dd, J=15.0, 6.5 Hz, 1H), 3.97 (q, J=6.8 Hz, 2H), 4.28 (q, J=7.0 Hz, 1H), 6.79 (d, J=8.6 Hz, 2H), 7.10 (d, J=8.6 Hz, 2H), 7.23 (d, J=8.6 Hz, 1H), 7.43 (s, 1H), 7.53 (dd, J=8.6, 1.9 Hz, 1H), 7.78 (d, J=2.0 Hz, 1H). MS (ESI) (M+H)$^+$ =378.38.

51BD: N-[1-(cyclopropylmethyl)-2-[1-(4-ethoxyphenyl) ethyl]-1H-benzimidazol-5-yl]-N-methyl acetamide To a solution of N-[1-(cyclopropylmethyl)-2-[1-(4-ethoxyphenyl)ethyl]-1H-benzimidazol-5-yl]-acetamide (2.13 g, 5.64 mmol) in THF (100 mL) was added NaH (0.45 g, 11.28 mmol) at 0° C. After stirring for 2 h, iodomethane (1.60 g, 11.28 mmol) was added at room temperature. The mixture was stirred overnight, quenched with MeOH (2 mL) and diluted with ether (200 mL) which was washed with saturated solution of ammonium chloride (100 mL) and dried with $Na_2SO_4$. After filtration and evaporation, the title compound (2.43 g, 100%) as a crude product was obtained. MS (ES) (M+H)$^+$=392.40.

51BE: 1-(cyclopropylmethyl)-2-[1-(4-ethoxyphenyl)ethyl]-N-methyl-1H-benzimidazol-5-amine A mixture of N-[1-(cyclopropylmethyl)-2-[1-(4-ethoxyphenyl)ethyl]-1H-benzimidazol-5-yl]-N-methyl acetamide (2.43 g, 5.64 mmol) and 40% KOH (50 ml) in EtOH was heated for 20 h at reflux. After being cooled down, the mixture was concentrated to a small volume (50 mL) and diluted with $H_2O$ (50 mL) which was extracted with dichloromethane (4×50 mL). The combined organic phases were dried with $Na_2SO_4$. After filtration and evaporation of the solvent, the residue was purified by MPLC using EtOAc on silica gel to give 1.93 g (99%) of the title compound as an off-white solid. MS (ESI) (M+H)$^+$=350.37.

Example 52

N-[1-(Cyclopropylmethyl)-2-[1-(4-ethoxyphenyl) ethyl]-1H-benzimidazol-5-yl]-N,3-dimethyl-butanamide To a solution of 1-(cyclopropylmethyl)-2-[1-(4-ethoxyphenyl)ethyl]-N-methyl-1H-benzimidazol-5-amine (349.5 mg, 1.0 mmol) in MeCN (25 mL) was added DIPEA (258.5 mg, 2.0 mmol), DMAP (10 mg) and isovaleryl chloride (180.9 mg, 1.5 mmol) at 0° C. The reaction mixture was stirred overnight at room temperature which was quenched with $H_2O$ (150 mL) and extracted with EtOAc (4×50 mL). The combined organic phases were washed with brine and dried with $Na_2SO_4$. Upon filtration and evaporation of the solvent, the residue was purified by MPLC using EtOAc on silica gel to give 431.9 mg (99%) of the desired product as a colorless syrup, which was converted to a TFA salt as a white solid. $^1$HNMR (400 MHz, $CD_3OD$): δ 0.22 (m, 1H), 0.45 (m, 2H), 0.57 (m, 1H), 0.86 (d, J=5.9 Hz, 6H), 1.02 (m, 1H), 1.38 (t, J=7.0 Hz, 3H), 1.83 (d, J=7.0 Hz, 3H), 2.06 (m, 2H), 2.10 (m, 1H), 3.34 (s, 3H), 4.02 (m, 3H), 4.21 (dd, J=15.0, 6.6 Hz, 1H), 4.65 (q, J=7.0 Hz, 1H), 6.90 (d, J=8.6 Hz, 2H), 7.21 (d, J=8.6 Hz, 2H), 7.28 (d, J=8.4 Hz, 1H), 7.62 (s, 1H), 7.72 (d, J=8.6 Hz, 1H). MS (ESI) (M+H)$^+$=434.42 (M+1)$^+$. Anal: Calcd for $C_{27}H_{35}N_3O_2$+0.80TFA+0.90MeOH: C, 64.00; H, 7.17; N, 7.54. Found: C, 63.98; H, 7.02; N, 7.34.

Example 53, 54 and 55

(rac)-N-[1-(Cyclopropylmethyl)-2-[1-(4-ethoxyphenyl)ethyl]1H-benzimidazol-5-yl]-N-methyl-N'-(1-methylethyl)-urea, (−)-N-[1-(Cyclopropylmethyl)-2-[1-(4-ethoxyphenyl)ethyl]-1H-benzimidazol-5-yl]-N-methyl-N'-(1-methylethyl)-urea and (+)-N-[1-(Cyclopropylmethyl)-2-[1-(4-ethoxyphenyl)ethyl]-1H-benzimidazol-5-yl]-N-methyl-N'-(1-methylethyl)-urea To a solution of 1-(cyclopropylmethyl)-2-[1-(4-ethoxyphenyl)ethyl]-N-methyl-1H-benzimidazol-5-amine (523.0 mg, 1.20 mmol) in 1,2-dichloroethane (25 mL) was added isopropyl isocyanate (1.02 g, 12 mmol) at room temperature. The mixture was heated for 14 h at 60° C. After concentration, the residue was purified by MPLC using EtOAc on silica gel to give 477.9 mg (92%) of the desired product (racemic) as a light yellow solid, which was converted to a TFA salt as a white solid. $^1$HNMR (400 MHz, $CD_3OD$): δ 0.27 (m, 1H), 0.51 (m, 2H), 0.60 (m, 1H), 1.08 (m, 1H), 1.15 (d, J=6.4 Hz, 6H), 1.39 (t, J=7.0 Hz, 3H), 1.90 (d, J=7.1 Hz, 3H), 3.35 (s, 3H), 3.97 (sep, J=6.7 Hz, 1H), 4.04 (q, J=7.0 Hz, 2H), 4.26 (dd, J=14.8, 7.0 Hz, 1H), 4.38 (dd, J=15.0, 7.2 Hz, 1H), 4.89 (q, J=7.0 Hz, 1H), 6.97 (d, J=8.8 Hz, 2H), 7.26 (d, J=8.6 Hz, 2H), 7.52 (dd, J=8.6, 1.8 Hz, 1H), 7.71 (s, 1H), 7.91 (d, J=9.0 Hz, 1H). MS (ESI) (M+H)$^+$=: 435.44 (M+1)$^+$. Anal. Calcd for $C_{26}H_{34}N_4O_2$+1.20TFA+0.10H$_2$O: C, 59.51; H, 6.22; N, 9.77. Found: C, 59.64; H, 6.22; N, 9.53.

The racemic mixture (rac)-N-[1-(cyclopropylmethyl)-2-[1-(4-ethoxyphenyl)ethyl]-1H-benzimidazol-5-yl]-N-methyl-N'-(1-methylethyl)-urea was separated by AD-chiral column using hex/iPrOH (9:1).

Enantiomer: (−)-N-[1-(cyclopropylmethyl)-2-[1-(4-ethoxyphenyl)ethyl]-1H-benzimidazol-5-yl]-N-methyl-N-(1-methylethyl)-urea: 221.2 mg (40%), TFA salt, white solid. $[α]_D$ −11.7° (c 0.25, EtOH). $^1$HNMR (400 MHz, $CD_3OD$): δ 0.27

(m, 1H), 0.51 (m, 2H), 0.60 (m, 1H), 1.08 (m, 1H), 1.15 (dd, J=6.6, 1.6 Hz, 6H), 1.39 (t, J=7.0 Hz, 3H), 1.90 (d, J=7.2 Hz, 3H), 3.35 (s, 3H), 3.97 (sep, J=6.6 Hz, 1H), 4.04 (q, J=7.0 Hz, 2H), 4.26 (dd, J=15.2, 7.2 Hz, 1H), 4.39 (dd, J=15.0, 6.8 Hz, 1H), 4.90 (q, J=7.0 Hz, 1H), 6.97 (m, 2H), 7.25 (m, 2H), 7.51 (dd, J=8.8, 1.8 Hz, 1H), 7.71 (d, J=1.8 Hz, 1H), 7.91 (d, J=9.0 Hz, 1H). MS (ESI) (M+H)$^+$=435.47 (M+1)$^+$. Anal. Calcd for $C_{26}H_{34}N_4O_2$+1.10TFA+0.10$H_2O$: C, 60.29; H, 6.33; N, 9.97. Found: C, 60.33; H, 6.33; N, 10.02.

Enantiomer: (+)-N-[1-(Cyclopropylmethyl)-2-[1-(4-ethoxyphenyl)ethyl]-1H-benzimidazol-5-yl]-N-methyl-N-(1-methylethyl)-urea: 186.4 mg (34%), TFA salt, white solid. $[\alpha]_D$+12.2° (c 0.27, EtOH). $^1$HNMR (400 MHz, $CD_3OD$): δ 0.27 (m, 1H), 0.51 (m, 2H), 0.60 (m, 1H), 1.08 (m, 1H), 1.15 (dd, J=6.6, 1.6 Hz, 6H), 1.39 (t, J=7.0 Hz, 3H), 1.90 (d, J=7.2 Hz, 3H), 3.35 (s, 3H), 3.97 (sep, J=6.6 Hz, 1H), 4.04 (q, J=7.0 Hz, 2H), 4.26 (dd, J=15.0, 7.2 Hz, 1H), 4.39 (dd, J=15.0, 6.8 Hz, 1H), 4.90 (q, J=7.2 Hz, 1H), 6.97 (m, 2H), 7.26 (m, 2H), 7.51 (dd, J=9.0, 2.0 Hz, 1H), 7.71 (d, J=1.8, 1H), 7.91 (d, J=9.0 Hz, 1H). MS (ESI) (M+H)$^+$=435.46 (M+1)$^+$. Anal. Calcd for $C_{26}H_{34}N_4O_2$+1.10TFA+0.20$H_2O$: C, 60.10; H, 6.35; N, 9.94. Found: C, 60.02; H, 6.28; N, 10.07.

Example 56

N-[1-(Cyclohexylmethyl)-2-[1-(4-ethoxyphenyl)ethyl]-1H-benzimidazol-5-yl]-N-methyl-N'-(1-methylethyl)-urea 56A: [4-[(Cyclohexylmethyl)amino]-3-nitrophenyl]-methyl ester carbamic acid To a stirring mixture of methyl 4-fluoro-3-nitrophenylcarbamate (3 g, 14 mmol) in 4:1 ethanol:water (40 mL+10 mL) was added cyclohexylmethylamine (3.6 mL, 28 mmol) at room temperature. The reaction mixture was heated at 60° C. overnight, cooled to room temperature. Water (20 mL) was added to the mixture and a deep orange solid was precipitated from solution and collected as the desired product (6 g, 100%). MS (ESI) (M+H)$^+$: 308.32 (M+1)$^+$.

56B: [3-amino-4-[(cyclohexylmethyl)amino]phenyl]-methyl ester carbamic acid

[4-[(Cyclohexylmethyl)amino]-3-nitrophenyl]-methyl ester carbamic acid was hydrogenated in ethyl acetate catalyzed by 10% Pd/C at 30–40 psi for 6 hours. The reaction mixture was subjected to filtration through celite and the solvent was removed to afford the desired product as a dark purple solid (2.02 g, 37%). MS (ESI) (M+H)$^+$: 278.30 (M+1)$^+$.

56C: [1-(cyclohexylmethyl)-2-[1-(4-ethoxyphenyl)ethyl]-1H-benzimidazol-5-yl]-methyl ester carbamic acid To a stirring solution of [3-amino-4-[(cyclohexylmethyl)amino]phenyl]-methyl ester carbamic acid (2.02 g, 7.3 mmol), 4-ethoxy-α-methyl benzeneacetic acid (1.4 g, 7.3 mmol) and diisopropylethylamine (2.2 mL, 12.4 mmol) in dry DMF (24 mL) was added HATU (3.1 g, 8.1 mmol) in one portion, at room temperature. The solution was partitioned between $CH_2Cl_2$ and water and was extracted (3×30 mL). The combined organic layers were washed with brine (30 mL), dried over $Na_2SO_4$ and were subjected to filtration and concentration. The residue was dissolved in acetic acid (180 mL) and was heated at 80° C. overnight. The solvent was evaporated, the residue was dissolved in EtOAc (200 mL), washed with 2 N NaOH, brine and dried over $Na_2SO_4$.

The mixture was subjected to filtration and concentration to afford the title compound as a yellow foam (2.44 g, 77%). MS (ESI) (M+H)$^+$=436.42 (M+1)$^+$ 56D: 1-(cyclohexylmethyl)-2-[1-(4-ethoxyphenyl)ethyl]-N-methyl-1H-benzimidazol-5-amine To a solution of [1-(cyclohexylmethyl)-2-[1-(4-ethoxyphenyl)ethyl]-1H-benzimidazol-5-yl]-methyl ester carbamic acid (2.44 g, 5.6 mmol) in $Et_2O$-MeOH (100 mL, just enough MeOH to dissolve the compound) was added a 1 M solution of HCl in $Et_2O$, dropwise, until no further precipitate formed (6 mL). The solvent was removed in vacuo. The HCl salt was dissolved in dry $Et_2O$ (120 mL) and THF (60 mL), the mixture was cooled to 0° C. and $LiAlH_4$ (986 mg, 25.2 mmol) was added in one portion. The solution was warmed slowly to room temperature and was stirred overnight, followed by cooling to −78° C., quenching with MeOH (12 mL) and water (12 mL), warming to room temperature, addition of $Na_2SO_4$ (25 g) and stirring at room temperature for 3 hours. Filtration through celite, washing with EtOAc and concentration afforded the title compound as a brown foam (2.1 g, 96%). MS (ESI) (M+H)$^+$=392.46 (M+1)$^+$ 56E: N-[1-(cyclohexylmethyl)-2-[1-(4-ethoxyphenyl)ethyl]-1H-benzimidazol-5-yl]-N-methyl -N'-(1-methylethyl)urea To a solution of 1-(cyclohexylmethyl)-2-[1-(4-ethoxyphenyl)ethyl]-N-methyl-1H-benzimidazol- 5-amine (2.1 g, 5.4 mmol) in 1,2-dichloroethane (270 mL) was added isopropyl isocyanate (1.1 mL, 10.8 mmol) at room temperature and the reaction mixture was heated at 60° C. overnight. The solution was cooled to room temperature, the solvent was evaporated and the brown residue was purified by MPLC (EtOAc on silica gel) to afford the title compound as a beige foam (1.5 g, 58%). $^1$H NMR (400 MHz, $CD_3OD$) δ 0.95–1.18 (m, 11H), 1.36 (t, J =7.0 Hz, 3H), 1.41–1.68 (m, 6H), 1.82 (d, J=7.0 Hz, 2H), 3.31 (s, 3H), 3.89–3.95 (m, 1H), 4.01 (apq, J=7.0 Hz, 2H), 4.13–4.18 (m, 1H), 4.68 (q, J=7.2 Hz, 1H), 7.17–7.20 (m, 2H), 7.35 (dd, J=2.0, 8.8 Hz, 1H), 7.63 (d, J=2.0 Hz, 1H), 7.71 (d, J=8.8 Hz, 1H). MS (ESI) (M+H)$^+$=477.48 (M+1)$^+$. Anal. Calcd for $C_{29}H_{40}N_4O_2$+ 0.5HCl+0.8 $CH_3OH$: C, 68.76; H, 8.46; N, 10.26. Found: C, 68.75; H, 8.61; N, 10.98.

Example 57

2-[(4-Ethoxyphenyl)methyl]-N,N-diethyl-3-[(5-nitro-2-thienyl)methyl]-3H-imidazo[4,5-b]pyridine-6-carboxamide 57A: N,N-Diethyl-5-nitro-6-(2-propenylamino)-3-pyridinecarboxamide To a solution of 6-chloro-5-nitro-3-pyridinecarboxylic acid (4.72 g, 23.30 mmol) in methanol (70 mL) at room temperature was added allyl amine (5.25 mL, 70.0 mmol) and the mixture was stirred overnight. The reaction was then concentrated in vacuo and the residue taken up into water (100 mL). The solution was brought to pH 3 by addition of 1 M HCl aqueous solution. The resulting suspension was extracted with EtOAc (50 mL). The aqueous phase was back-extracted with additional EtOAc (2×50 mL). The organic phases were combined, dried with $MgSO_4$, and filtered. The solution was concentrated in vacuo providing 5-nitro-6-(2-propenylamino)-3-pyridinecarboxylic acid which was used without further purification.

This residue was then taken up in diethylamine (100 mL). To this solution was added HATU (9.30 g, 24.47 mmol). The mixture was stirred for 48 hours at room temperature. The reaction was then concentrated in vacuo and the residue taken up into NaHCO$_3$ saturated aqueous solution (100 mL) and EtOAc (100 mL). The phases were separated and the aqueous phase was back-extracted with additional EtOAc (2×50 mL). The organic phases were combined, dried with MgSO$_4$, filtered and concentrated in vacuo. The residue was purified using silica gel flash chromatography ([2% MeOH+ 1% NH$_4$OH aq] in CH$_2$Cl$_2$) to provide 4.83 g of the title compound NN-diethyl-5-nitro-6-(2-propenylamino)-3-pyridinecarboxamide (74.5% yield from 6-chloro-5-nitro-3-pyridinecarboxylic acid). $^1$H-NMR (400 MHz, CDCl$_3$): δ 1.26 (m, 6H), 3.28 (br s, 1H), 3.47 (m, 4H), 4.26 (m, 2H), 5.22 (m, 1H), 5.30 (m, 1H), 7.40 (d, J=8.2 Hz, 1H), 7.70 (d, J=8.2 Hz, 1H). MS (ESI) (M+H)$^+$: 279.

57B: 5-amino-N,N-diethyl-6-(2-propenylamino)-3-pyridinecarboxamide

To a solution of N,N-diethyl-5-nitro-6-(2-propenylamino)-3-pyridinecarboxamide (4.83 g, 17.25 mmol) in DMF (50 mL) at room temperature was added tin dichloride dihydrate (8.56 g, 37.95 mmol). The mixture was stirred overnight at 80° C. The reaction was brought to room temperature and concentrated in vacuo. The residue was taken up into NaHCO$_3$ saturated aqueous solution (100 mL) and EtOAc (100 mL). The suspension was filtered and the phases separated. The aqueous phase was back-extracted with additional EtOAc (100 mL). The organic phases were combined, dried with MgSO$_4$, filtered and concentrated in vacuo. The residue was purified using silica gel flash chromatography ([5% MeOH+1% NH$_4$OH aq] in CH$_2$Cl$_2$) to provide 2.10 g of the title compound 5-amino-N,N-diethyl-6-(2-propenylamino)-3-pyridinecarboxamide (49.0% yield from N,N-diethyl-5-nitro-6-(2-propenylamino)-3-pyridinecarboxamide). $^1$H-NMR (400 MHz, CDCl$_3$): δ 1.20 (t, J=7.2 Hz, 6H), 3.23 (br s, 1H), 3.45 (m,4H), 4.12 (m, 2H), 4.44 (br s, 2H), 5.17 (d, J=12.5 Hz, 1H), 5.26 (d, J=17.2 Hz, 1H), 6.04 (m, 1H), 7.00 (d, J=2.0 Hz, 1H), 7.83 (d, J=2.0 Hz, 1H). MS (ESI) (M+H)$^+$: 2.49.

57C: 5-[[(4-ethoxyphenyl)acetyl]amino]-N,N-diethyl-6-(2-propenylamino)-3-pyridinecarboxamide To a solution of 5-amino-N,N-diethyl-6-(2-propenylamino)-3-pyridinecarboxamide (1.61 g, 6.50 mmol) in dichloromethane (50 mL) at 0° C. was added 4-ethoxybenzeneacetyl chloride (1.35 g, 6.80 mmol). The mixture was stirred for 3 hours at room temperature. The reaction was then quenched with NaHCO$_3$ saturated aqueous solution (100 mL) and extracted with dichloromethane (50 mL). The aqueous phase was back-extracted with additional dichloromethane (2×50 mL). The organic phases were combined, dried with MgSO$_4$, filtered and concentrated in vacuo. The residue was purified using silica gel flash chromatography ([2% MeOH+0.5% NH$_4$OH aq] in CH$_2$Cl$_2$) to provide 1:69 g of the title compound 5-[[(4-ethoxyphenyl)acetyl]amino]-NN-diethyl-6-(2-propenylamino)-3-pyridinecarboxamide (63.3% yield from 5-amino-N,N-diethyl-6-(2-propenylamino)-3-pyridinecarboxamide). $^1$H-NMR (400 MHz, CDCl$_3$): δ 1.18 (t,J=7.2 Hz, 6H), 1.41 (t,J=7.8 Hz, 3H), 3.42 (br s, 1H), 3.69 (s, 2H), 4.02 (m, 8H), 5.13 (m, 2H), 5.92 (m, 1 H), 6.90 (m, 2H), 7.27 (m, 2H), 7.34 (m, 1H), 8.00 (m, 1H). MS (ES) (M+H)$^+$: 411.

57D: 6-amino-5-[[(4-ethoxyphenyl)acetyl]amino]-N,N-diethyl-3-pyridinecarboxamide To a degassed solution of 5-[[(4-ethoxyphenyl)acetyl] amino]-N,N-diethyl-6-(2-propenylamino)-3-pyridinecarboxamide (1.04 g, 2.53 mmol) in dichloromethane (20 mL) at room temperature was added palladium tetrakis (117 mg, 0.10 mmol), followed by acetic acid (580 μL, 10.14 mmol) and phenyl silane (625 μL, 5.07 mmol). The mixture was stirred for 6 hours. The reaction was then quenched with NaHCO$_3$ saturated aqueous solution (50 mL) and extracted with EtOAc (20 mL). The aqueous phase was back-extracted with additional dichloromethane (2×20 mL). The organic phases were combined, dried with MgSO$_4$, filtered and concentrated in vacuo. The residue was purified using silica gel flash chromatography ([3% MeOH+1% NH$_4$OHaq] in CH$_2$Cl$_2$) to provide 705 mg of the title compound 6-amino-5-[[(4-ethoxyphenyl)acetyl]amino]-N,N-diethyl-3-pyridinecarboxamide (75.2% yield from 5-[[(4-ethoxyphenyl) acetyl]amino]-N,N-diethyl-6-(2-propenylamino)-3-pyridinecarboxamide). $^1$H-NMR (400 MHz, CDCl$_3$): δ 1.18 (br s, 6H), 1.43 (t, J=7.0 Hz, 3H), 3.42 (br s, 4H), 3.69 (s, 2H), 4.04 (q, J=7.0 Hz, 2H), 4.73 (s, 2H), 6.91 (d, J=8.6 Hz, 2H), 7.26 (d, J=8.6 Hz, 2H), 7.38 (m, 1H), 7.78 (s, 1H), 7.95 (m, 1H). MS (ESI) (M+H)$^+$: 372.

57E: 2-[(4-ethoxyphenyl)methyl]-N,N-diethyl-3-[(5-nitro-2-thienyl)methyl]-3H-imidazo[4,5-b]pyridine-6-carboxamide To a solution of 6-amino-5-[[(4-ethoxyphenyl)acetyl] amino]-N,N-diethyl-3-pyridinecarboxamide (30 mg, 0.08 mmol) in dichloroethane (0.5 mL) and acetic acid (0.5 mL) at room temperature was added 5-nitro-2-thiophenecarboxaldehyde (19 mg, 0.12 mmol). The mixture was stirred for 4.5 hours. BH$_3$·pyridine (8.2 μL, 0.08 mmol) was added and the reaction brought to 84° C. After stirring overnight, the mixture was cooled to room temperature and 5-nitro-2-thiophenecarboxaldehyde (19 mg, 0.12 mmol) was added. The mixture was stirred for 5 hours. BH$_3$.pyridine (8.2 μL, 0.08 mmol) was added and the reaction brought to 84° C. After stirring overnight, the reaction was quenched with 1 M NaOH aqueous solution (20 mL) and extracted with EtOAc (20 mL). The aqueous phase was back-extracted with additional dichloromethane (2×20 mL). The organic phases were combined, dried with MgSO$_4$, filtered and concentrated in vacuo. The residue was purified using silica gel flash chromatography ([3% MEOH+0.5% NH$_4$OH aq] in CH$_2$Cl$_2$) to provide the title compound 2-[(4-ethoxyphenyl)methyl]-N,N-diethyl-3-[(5-nitro-2-thienyl)methyl]-3H-imidazo[ 4,5-b] pyridine-6-carboxamide (purity: >84% at 215 nm, >81% at 254 nm, >68% at 280 nm). $^1$H-NMR (400 MHz, CDCl$_3$): δ 1.23 (m, 6H), 1.40 (t, J=6.8 Hz, 3H), 3.36 (br s, 2H), 3.60 (br s, 2H), 3.98 (q, J=6.8 Hz, 2H), 4.29 (s, 2H), 4.84 (s, 2H), 6.80 (d, J=8.6 Hz, 2H), 7.07 (d, J=8.6 Hz, 2H), 7.66 (d, J=4.1 Hz, 1H), 7.77 (d, J=4.1 Hz, 1H), 8.03 (d, J=2.0 Hz, 1H), 8.03 (d, J=2.0 Hz, 1H). MS (ESI) (M+H)$^+$: 494.

Example 58

3-(Cyclopropylmethyl)-2-[(4-ethoxyphenyl)methyl]-N-methyl-3H-imidazo[4,5-b]pyridin-6-amine 58A: N-(cyclopropylmethyl)-3,5-dinitro-2-pyridinamine To a solution of 2-chloro-3,5-dinitro-pyridine (1.00 g, 4.91 mmol) in dichloromethane (10 mL), kept at room temperature with a water bath, was added dropwise cyclopropyl methylamine (852 mL, 9.83 mmol). Upon addition, an instant orange coloration was observed and precipitates were detected. The mixture was stirred for 1 hour. The reaction was quenched is with 1 M NaOH aqueous solution (10 mL) and extracted with EtOAc (20 mL). The organic phase was washed with brine, dried with MgSO$_4$, filtered and concentrated in vacuo. The process gave 1.117 g of the title compound N-(cyclopropylmethyl)-3,5-dinitro-2-pyridinamine (96% yield from 2-chloro-3,5-dinitro-pyridine), with purity>96% by HPLC analysis. The residue was used without further purification. $^1$H-NMR (400 MHz, CDCl$_3$): δ 0.36 (m, 2H), 0.66 (m, 2H), 1.18 (m, 1H), 3.61 (dd, J=5.3, 7.2 Hz, 2H), 8.85 (m, 1H), 9.23 (m, 21). MS (ESI) (M+H)$^+$: 239.

58B: N$^2$-(cyclopropylmethyl)-5-nitro-2,3-pyridinediamine

To a solution of N-(cyclopropylmethyl)-3,5-dinitro-2-pyridinamine (1.17 g, 4.92 mmol) in EtOAc (50 mL) at room temperature was added Pd/C (394 mg, 0.25 mmol, 10% grade). The mixture was placed in a Parr apparatus under 35 psi H$_2$. The mixture was shaken overnight. The reaction was filtered over Celite and concentrated in vacuo. The residue was purified using silica gel flash chromatography ([2.5% MeOH+1% NH$_4$OH aq] in CH$_2$Cl$_2$) to provide 792 mg of the title compound N$^2$-(cyclopropylmethyl)-5-nitro-2,3-pyridinediamine (77.3% yield from N-(cyclopropylmethyl)-3,5-dinitro-2-pyridinamine). $^1$H-NMR (400 MHz, CDCl$_3$): δ 0.31 (m, 2H), 0.61 (m, 2H), 1.14 (m, 1H), 3.34 (br s, 2H), 3.42 (dd, J=5.3, 7.2 Hz, 2H), 5.15 (br s, 1H), 7.62 (d, J=2.5 Hz, 1H), 8.73 (d, J=2.5 Hz, 2H). MS (ESI) (M+H)$^+$: 209.

58C: 3-(cyclopropylmethyl)-2-[(4-ethoxyphenyl)methyl]-6-nitro-3H-imidazo[4,5-b]pyridine To a solution of N$^2$-(cyclopropylmethyl)-5-nitro-2,3-pyridinediamine (792 mg, 3.80 mmol) in dichloromethane (50 mL) at room temperature was added 4-ethoxy-benzeneacetyl chloride (795 mg, 4.00 mmol). The mixture was stirred for 10 hours. The mixture was concentrated in vacuo and the residue dissolved in dichloroethane (25 mL) and acetic acid (25 mL). The mixture was stirred for 48 hours at 85° C. The reaction was then cooled to room temperature and brought to pH=10 by addition of 1 M NaOH aqueous solution. The mixture was extracted with EtOAc (50 mL). The aqueous phase was back-extracted with additional EtOAc (2×50 mL). The organic phases were combined, dried with MgSO$_4$, filtered and concentrated in vacuo. The residue was purified using silica gel flash chromatography ([2.5%. MeOH+0.5% NH$_4$OH aq] in CH$_2$Cl$_2$) to provide 1.02 g of the title compound 3-(cyclopropylmethyl)-2-[(4-ethoxyphenyl)methyl]-6-nitro-3H-imidazo[4,5-b]pyridine (76.0% yield from N$^2$-(cyclopropylmethyl)-5-nitro-2,3-pyridinediamine). $^1$H-NMR (400 MHz, CDCl$_3$): δ 0.44 (m, 2H), 0.52 (m, 2H), 1.10 (m, 1H), 1.40 (t, J=6.8 Hz, 3H), 4.01 (q, J=6.8 Hz, 2H), 4.10 (d, J=7.2 Hz, 2H), 4.35 (s, 2H), 6.86 (d, J=8.8 Hz, 2H), 7.18 (d, J=8.8 Hz, 2H), 8.80 (d, J=2.3 Hz, 1H) 9.26 (d, J=2.3 Hz, 1H). MS (ESI) (M+H)$^+$: 353.

58D: 3-(cyclopropylmethyl)-2-[(4-ethoxyphenyl)methyl]-3H-imidazo[4,5-b]pyridin-6-amine To a solution of 3-(cyclopropylmethyl)-2-[(4-ethoxyphenyl)methyl]-6-nitro-3H-imidazo[4,5-b]pyridine (1.35 g, 3.84 mmol) in EtOAc (20 mL) and acetic acid (1 mL) at room temperature was added Pd/C (308 mg, 10% grade). The mixture was placed in a Parr apparatus under 35 psi H$_2$. The mixture was shaken for 72 hours. The reaction was filtered over Celite. The filtrate was taken up into 1 M NaOH aqueous solution (25 mL) and EtOAc (50 mL) and the phases separated. The aqueous phase was back-extracted with additional EtOAc (2×50 mL). The organic phases were combined, dried with MgSO$_4$, filtered and concentrated in vacuo. The process gave 1.18 g of the title compound 3-(cyclopropylmethyl)-2-[(4-ethoxyphenyl)methyl]-3H-imidazo[4,5-b]pyridin-6-amine (95% yield from 3-(cyclopropylmethyl)-2-[(4-ethoxyphenyl)methyl]-6-nitro-3H-imidazo[4,5-b]pyridine), with purity>95% by HPLC analysis. The residue was used without further purification. $^1$H-NMR (400 MHz, CDCl$_3$): δ 0.35 (m, 2H), 0.46 (m, 2H), 1.11 (m, 1H), 1.39 (t, J=6.8 Hz, 3H), 3.26 (br s, 2H), 3.98 (m, 4H), 4.25 (s, 2H), 6.83 (d, J=8.8 Hz, 2H), 7.16 (d, J=8.8 Hz, 2H), 7.34 (d, J=2.3 Hz, 1H), 7.87 (d, J=2.3 Hz, 1H). MS (ESI) (M+H)$^+$: 323.

58E: [3-(cyclopropylmethyl)-2-[(4-ethoxyphenyl)methyl]-3H-imidazo[4,5-b]pyridin-6-yl]-carbamic acid methyl ester To a solution of 3-(cyclopropylmethyl)-2-[(4-ethoxyphenyl)methyl]-3H-imidazo[4,5-b]pyridin-6-amine (1.18 g, 3.66, mmol) in dichloromethane (20 mL) at 0° C. was added Hunig's base (869 μL, 4.99 mmol) followed by methyl chloroformate (326 μL, 4.22 mmol). The mixture was brought to room temperature and stirred overnight. The reaction was quenched with NH$_4$Cl saturated aqueous solution and extracted with dichloromethane (50 mL).

The aqueous phase was back-extracted with additional dichloromethane (2×50 mL). The organic phases were combined, dried with MgSO$_4$, filtered and concentrated in vacuo. The residue was purified using silica gel flash chromatography ([3 to 7% MeOH+1% NH$_4$OH aq] in CH$_2$Cl$_2$) to provide 1.02 g of the title compound [3-(cyclopropylmethyl)-2-[(4-ethoxyphenyl)methyl]-3H-imidazo[4,5-b]pyridin-6-yl]-carbamic acid methyl ester (73.3% yield from 3-(cyclopropylmethyl)-2-[(4-ethoxyphenyl)methyl]-3H-imidazo[4,5-b]pyridin-6-amine). $^1$H-NMR (400 MHz, CDCl$_3$): δ 0.38 (m, 2H), 0.45 (m, 2H), 1.11 (m, 1H), 1.39 (t, J=7.0 Hz, 3H), 3.81 (s, 3H), 4.00 (m, 4H), 4.29 (s, 2H), 6.69 (br s, 1H), 6.84 (d, J=8.6 Hz, 2H), 7.15 (d, J=8.6 Hz, 2H), 8.13 (br s, 1H), 8.26 (br s, 1H). MS (ESI) (M+H)$^+$: 381.

58F: 3-(cyclopropylmethyl)-2-[(4-ethoxyphenyl)methyl]-N-methyl-3H-imidazo[4,5-b]pyridin-6-amine To a solution of [3-(cyclopropylmethyl)-2-[(4-ethoxyphenyl)methyl]-3H-imidazo[4,5-b]pyridin-6-yl]-carbamic acid methyl ester (550 mg, 1.46 mmol) in dichloromethane (20 mL) at room temperature was added 1 M HCl in diethyl ether solution (3 mL). The mixture was stirred for 10 minutes and concentrated in vacuo. The residue was taken up into THF (5 mL) and diethyl ether (30 mL) and cooled to 0° C. LAH (137 mg, 3.61 mmol) was added to the solution. The mixture was stirred overnight. The reaction was then cooled to −78° C. and quenched with MeOH (3.20 mL) and water (3.20 mL). Na$_2$SO$_4$ was added to the mixture which was allowed to slowly warm up to room temperature. The mixture was filtered over Celite and concentrated in vacuo. The residue was purified using silica gel flash chromatography ([3.5% MeOH+0.5% NH$_4$OH aq] in CH$_2$Cl$_2$) to provide 445 mg of the title compound 3-(cyclopropylmethyl)-2-[(4-ethoxyphenyl)methyl]-N-methyl-3H-imidazo[4,5-b]pyridin-6-amine (90.6% yield from [3-(cyclopropylmethyl)-2-[(4-ethoxyphenyl)methyl]-3H-imidazo[4,5-b]pyridin-6-yl]-carbamic acid methyl ester). $^1$H-NMR (400 MHz, CDCl$_3$): δ 0.35 (m, 2H), 0.46 (m, 2H), 1.11 (m, 1H), 1.39 (t, J=7.0 Hz, 3H), 2.90 (s, 3H), 3.98 (m, 4H), 4.25 (s, 2H), 6.83 (d, J=8.8 Hz, 2H), 7.15 (d, J=8.8 Hz, 2H), 7.23 (d, J=2.5 Hz, 1H), 7.83 (d, J=2.5 Hz, 1H). MS (ESI) (M+H)$^+$: 337.

Example 59

N-[3-(Cyclopropylmethyl)-2-[(4-ethoxyphenyl)methyl]-3H-imidazo[4,5-b]pyridin-6-yl]-N,3-dimethyl-butanamide To a solution of 3-(cyclopropylmethyl)-2-[(4-ethoxyphenyl)methyl]-N-methyl-3H-imidazo[4,5-b]pyridin-6-amine (143.6 mg, 0.43 mmol) in dichloroethane (17 mL) at room temperature was added triethylamine (300 μL, 2.15 mmol) followed by isovaleryl chloride (156 μL, 1.28 mmol). The mixture was stirred overnight. The reaction was quenched with $Na_2CO_3$ saturated aqueous solution (10 mL) and extracted with EtOAc (25 mL). The aqueous phase was back-extracted with additional EtOAc (25 mL). The organic phases were combined, dried with $MgSO_4$, filtered and concentrated in vacuo. The residue was purified using preparative HPLC (C-18 column, 10 to 70% [0.1% TFA in AcCN solution] in 0.1% TFA aqueous solution) to provide 95.5 mg of the TFA salt of the title compound N-[3-(cyclopropylmethyl)-2-[(4-ethoxyphenyl)methyl]-3H-imidazo[4,5-b]pyridin-6-yl]-N,3-dimethyl-butanamide (41.5% yield from 3-(cyclopropylmethyl)-2-[(4-ethoxyphenyl)methyl]-N-methyl-3H-imidazo[4,5-b]pyridin-6-amine).
$^1$H-NMR (400 MHz, $d_3$-MeOD): δ 0.45 (m, 4H), 0.82 (m, 6H), 1.17 (m, 1H), 1.36 (t, J=7.0 Hz, 3H), 2.00 (m, 2H), 3.32 (s, 3H), 4.00 (t, J=7.0 Hz, 2H), 4.22 (d, J=7.2 Hz, 2H), 4.44 (s, 2H), 6.90 (d, J=8.6 Hz, 2H), 7.23 (d, J=8.6 Hz, 2H), 7.97 (d, J=2.15 Hz, 1H), 8.33 (br s, 1H). MS (ESI) (M+H)$^+$: 421.

Example 60

N-[3-(Cyclopropylmethyl)-2-[(4-ethoxyphenyl)methyl]-3H-imidazo[4,5-b]pyridin-6-yl]-N-methyl-N'-(1-methylethyl)-urea To a solution of 3-(cyclopropylmethyl)-2-[(4-ethoxyphenyl)methyl]-N-methyl-3H-imidazo[4,5-b]pyridin-6-amine (163.4 mg, 0.49 mmol) in DMF (20 mL) at room temperature was added isopropyl isocyanate (48 μL, 0.49 mmol). The mixture was stirred for 72 hours at 50° C. HPLC analysis of the reaction mixture indicated the presence of starting material. Hence, more isopropyl isocyanate (144 μL, 1.47 mmol) was added. The resulting mixture was stirred for 12 hours at 50° C. The reaction was then taken up into water (150 mL) and EtOAc (150 mL). The aqueous phase was back-extracted with additional EtOAc (100 mL). The organic phases were combined, dried with $MgSO_4$, filtered and concentrated in vacuo. The residue was purified using preparative HPLC (C-18 column, 10 to 70% [0.1% TFA in AcCN solution] in 0.1% TFA aqueous solution) to provide 92 mg of the TFA salt of the title compound N-[3-(cyclopropylmethyl)-2-[(4-ethoxyphenyl)methyl]-3H-imidazo[4,5-b]pyridin-6-yl]-N-methyl-N'-(1-methylethyl)-urea (35.0% yield from 3-(cyclopropylmethyl)-2-[(4-ethoxyphenyl)methyl]-N-methyl-3H-imidazo[4,5-b]pyridin-6-amine).
$^1$H-NMR (400 MHz, $d_3$-MeOD): δ 0.46 (m, 4H), 1.09 (d, J=6.6 Hz, 6H), 1.18 (m, 1H), 1.36 (t, J=7.0 Hz, 3H), 3.30 (s, 3H), 3.92 (m, 1H), 4.00 (t, J=7.0 Hz, 2H), 4.22 (d, J=7.2 Hz, 2H), 4.44 (s, 2H), 6.90 (d, J=8.6 Hz, 2H), 7.22 (d, J=8.6 Hz, 2H), 7.93 (d, J=2.2 Hz, 1H), 8.34 (d, J=2.2 Hz, 1H). MS (ESI) (M+H)$^+$: 422.

Example 61

N-[3-(Cyclopropylmethyl)-2-[(4-ethoxyphenyl)methyl]-3H-imidazo[4,5-b]pyridin-6-yl]-N-methyl-benzenesulfonamide To a solution of 3-(cyclopropylmethyl)-2-[(4-ethoxyphenyl)methyl]-N-methyl-3H-imidazo[4,5-b]pyridin-6-amine (237.0 mg, 0.70 mmol) in acetonitrile (5 mL) at room temperature was added triethylamine (196 μL, 1.41 mmol) followed by benzenesulfonyl chloride (156 mL, 0.92 mmol). The mixture was stirred overnight. The reaction mixture was concentrated in vacuo. The residue was dissolved into EtOAc (10 ml) and $Na_2CO_3$ saturated aqueous solution (10 mL). The phases were separated and the aqueous phase was back-extracted with additional EtOAc (10 mL). The organic phases were combined, dried with $MgSO_4$, filtered and concentrated in vacuo. The residue was purified using preparative HPLC (C-18 column, 20 to 80% [0.1% AcOH in AcCN solution] in 0.1% AcOH aqueous solution) to provide 63 mg of the AcOH salt of the title compound N-[3-(cyclopropylmethyl)-2-[(4-ethoxyphenyl)methyl]-3H-imidazo[4,5-b]pyridin-6-yl]-N-methyl-benzenesulfonamide (17% yield from 3-(cyclopropylmethyl)-2-[(4-ethoxyphenyl)methyl]-N-methyl-3H-imidazo[4,5-b]pyridin-6-amine).
$^1$H-NMR (400 MHz, $d_3$-MeOD): δ 0.37 (m, 2H), 0.42 (m, 2H), 1.10 (m, 1H), 1.35 (t, J=7.0 Hz, 3H), 3.31 (s, 3H), 3.99 (t, J=7.0 Hz, 2H), 4.10 (d, J=7.2 Hz, 2H), 4.32 (s, 2H), 6.86 (d, J=8.6 Hz, 2H), 7.17 (d, J=8.6 Hz, 2H), 7.55 (m, 2H), 7.57 (m, 2H), 7.59 (m, 1H), 7.70 (m, 1H), 8.11 (d, J=2.2 Hz, 1H). MS (ESI) (M+H)$^+$: 477.

Example 62

N-[3-(Cyclopropylmethyl)-2-[(4-ethoxyphenyl)methyl]-3H-imidazo[4,5-b]pyridin-6-yl]-N-methyl-2-thiophenesulfonamide To a solution of 3-(cyclopropylmethyl)-2-[(4-ethoxyphenyl)methyl]-N-methyl-3H-imidazo[4,5-b]pyridin-6-amine (250.0 mg, 0.74 mmol) in acetonitrile (5 mL) at room temperature was added triethylamine (207 mL, 1.49 mmol) followed by 2-thiophenesulfonyl chloride (176 μL, 0.96 mmol). The mixture was stirred overnight. The reaction mixture was concentrated in vacuo. The residue was dissolved into EtOAc (10 ml) and $Na_2CO_3$ saturated aqueous solution (10 mL). The phases were separated and the aqueous phase was back-extracted with additional EtOAc (10 mL). The organic phases were combined, dried with $MgSO_4$, filtered and concentrated in vacuo. The residue was purified using preparative HPLC (C-18 column, 20 to 80% [0.1% AcOH in AcCN solution] in 0.1% AcOH aqueous solution) to provide 72 mg of the AcOH salt of the title compound N-[3-(cyclopropylmethyl)-2-[(4-ethoxyphenyl)methyl]-3H-imidazo[4,5-b]pyridin-6-yl]-N-methyl-2-thiophenesulfonamide (18% yield from 3-(cyclopropylmethyl)-2-[(4-ethoxyphenyl)methyl]-N-methyl-3H-imidazo[4,5-b]pyridin-6-amine). $^1$H-NMR (400 MHz, $d_3$-MeOD): δ 0.37 (m, 2H), 0.43 (m, 2H), 1.10 (m, 1H), 1.35 (t, J=7.0 Hz, 3H), 3.32 (s, 3H), 3.99 (t, J=7.0 Hz, 2H), 4.10 (d, J=7.2 Hz, 2H), 4.32 (s, 2H), 6.86 (d, J=8.8 Hz, 2H), 7.17 (d, J=8.8 Hz, 2H), 7.20 (m, 1H), 7.44 (d, J=5.3 Hz, 1H), 7.61 (d, J=2.3 Hz, 1H), 7.85 (d, J=5.1 Hz, 1H), 8.15 (d, J=2.3 Hz, 1H). MS (ESI) (M+H)$^+$: 483.

TABLE 3

Other compounds of the invention

| Example # | Compound Name | MS (ESI) (M + H)+ |
|---|---|---|
| 63 | 1-[2-(dimethylamino)ethyl]-2-(4-ethoxybenzyl)-N,N-diethyl-1H-benzimidazole-5-carboxamide | 423 |
| 64 | 1-allyl-2-(4-ethoxybenzyl)-N,N-diethyl-1H-benzimidazole-5-carboxamide | 392 |
| 65 | 1-cyclopropyl-2-(4-ethoxybenzyl)-N,N-diethyl-1H-benzimidazole-5-carboxamide | 392 |
| 66 | 1-(cyclopropylmethyl)-2-(4-ethoxybenzyl)-N,N-diisopropyl-1H-benzimidazole-5-carboxamide | 434 |
| 67 | 2-(4-ethoxybenzyl)-N,N-diethyl-1-(2-pyridinylmethyl)-1H-benzimidazole-5-carboxamide | 443 |
| 68 | 1-(cyclopropylmethyl)-2-(4-ethoxybenzyl)-N,N-diethyl-1H-benzimidazole-5-sulfonamide | 442 |
| 69 | N-[1-(cyclopropylmethyl)-2-(4-ethoxybenzyl)-1H-benzimidazol-5-yl]-N-methylcyclobutanecarboxamide | 418 |
| 70 | methyl 1-(cyclopropylmethyl)-2-(4-ethoxybenzyl)-1H-benzimidazol-5-yl(3-methyl-2-butenyl)carbamate | 448 |
| 71 | 2-(4-ethoxybenzyl)-N,N-diethyl-3-isopentyl-3H-imidazo[4,5-b]pyridine-6-carboxamide | 423 |
| 72 | 1-(cyclopropylmethyl)-2-(4-ethoxybenzyl)-5-(4-morpholinylsulfonyl)-1H-benzimidazole | 456 |
| 73 | 5-(1-azetidinylsulfonyl)-1-(cyclopropylmethyl)-2-(4-ethoxybenzyl)-1H-benzimidazole | 426 |
| 74 | N-{[1-(cyclopropylmethyl)-2-(4-ethoxybenzyl)-1H-benzimidazol-5-yl]methyl}-N-ethylethanamine | 392 |
| 75 | N-[1-(cyclopropylmethyl)-2-(4-ethoxybenzyl)-1H-benzimidazol-5-yl]-N-ethylnicotinamide | 455 |
| 76 | N-[1-(cyclopropylmethyl)-2-(4-ethoxybenzyl)-1H-benzimidazol-5-yl]-N'-isopropyl-N-methylurea | 421 |
| 77 | 1-(cyclopropylmethyl)-2-[(5-ethoxy-2-pyridinyl)methyl]-N-ethyl-1H-benzimidazole-5-carboxamide | 379 |
| 78 | 1-(cyclopropylmethyl)-2-(4-ethoxybenzyl)-N-ethyl-1H-benzimidazole-5-carboxamide | 378 |
| 79 | 3-(cyclopropylmethyl)-2-(4-ethoxybenzyl)-6-(1-pyrrolidinylcarbonyl)-3H-imidazo[4,5-b]pyridine | 405 |
| 80 | 1-[(2-chloro-1,3-thiazol-4-yl)methyl]-2-(4-ethoxybenzyl)-N,N-diethyl-1H-benzimidazole-5-carboxamide | 483/485 |
| 81 | 2-(4-ethoxybenzyl)-N,N-diethyl-1-(1,3-thiazol-4-ylmethyl)-1H-benzimidazole-5-carboxamide | 449 |
| 82 | 2-(4-ethoxybenzyl)-N,N-diethyl-1-(2-quinolinylmethyl)-1H-benzimidazole-5-carboxamide | 493 |
| 83 | 2-(4-ethoxybenzyl)-N,N-diethyl-1-[3-(1H-imidazol-1-yl)propyl]-1H-benzimidazole-5-carboxamide | 460 |
| 84 | 1-[2-(dimethylamino)ethyl]-N,N-diethyl-2-[4-(trifluoromethoxy)benzyl]-1H-benzimidazole-5-carboxamide | 463 |
| 85 | N,N-diethyl-1-[2-(4-morpholinyl)ethyl]-2-[4-(trifluoromethoxy)benzyl]-1H-benzimidazole-5-carboxamide | 505 |
| 86 | N,N-diethyl-2-(4-isopropoxybenzyl)-1-[2-(4-morpholinyl)ethyl]-1H-benzimidazole-5-carboxamide | 479 |
| 87 | N,N-diethyl-1-[2-(1-piperidinyl)ethyl]-2-[4-(trifluoromethoxy)benzyl]-1H-benzimidazole-5-carboxamide | 503 |
| 88 | 2-[(E)-2-(4-ethoxyphenyl)ethenyl]-N,N-diethyl-1-[(1-ethyl-2-pyrrolidinyl)methyl]-1H-benzimidazole-5-carboxamide | 475 |
| 89 | N,N-diethyl-1-[(1-ethyl-2-pyrrolidinyl)methyl]-2-[4-(trifluoromethoxy)benzyl]-1H-benzimidazole-5-carboxamide | 503 |
| 90 | N-benzyl-1-(cyclopropylmethyl)-2-(4-ethoxybenzyl)-N-ethyl-1H-benzimidazole-5-carboxamide | 468 |
| 91 | 1-(cyclopropylmethyl)-2-(4-ethoxybenzyl)-N-[(2R)-tetrahydro-2-furanylmethyl]-1H-benzimidazole-5-carboxamide | 434 |
| 92 | 1-(cyclopropylmethyl)-2-(4-ethoxybenzyl)-5-[(4-phenyl-1-piperidinyl)carbonyl]-1H-benzimidazole | 494 |
| 93 | N'-tert-butyl-N-[1-(cyclopropylmethyl)-2-(4-ethoxybenzyl)-1H-benzimidazol-5-yl]-N-methylthiourea | 451 |
| 94 | N-allyl-N-[1-(cyclopropylmethyl)-2-(4-ethoxybenzyl)-1H-benzimidazol-5-yl]-1H-indole-2-carboxamide | 505 |
| 95 | N-[1-(cyclopropylmethyl)-2-(4-ethoxybenzyl)-1H-benzimidazol-5-yl]-N-methyl-2-propanesulfonamide | 442 |
| 96 | N-[1-(cyclopropylmethyl)-2-(4-ethoxybenzyl)-1H-benzimidazol-5-yl]-N-methylethanesulfonamide | 428 |
| 97 | 1-(cyclopropylmethyl)-2-(4-ethoxybenzyl)-5-{[4-(2-pyridinyl)-1-piperazinyl]carbothioyl}-1H-benzimidazole | 512 |
| 98 | 1-(cyclopropylmethyl)-2-(4-ethoxybenzyl)-5-{[4-(1-pyrrolidinyl)-1-piperidinyl]carbothioyl}-1H-benzimidazole | 503 |
| 99 | N-[3-(4-{[1-(cyclopropylmethyl)-2-(4-ethoxybenzyl)-1H-benzimidazol-5-yl]carbothioyl}-1-piperazinyl)propyl]-N,N-dimethylamine | 520 |
| 100 | 1-(cyclopropylmethyl)-2-(4-ethoxybenzyl)-N-[2-(3-pyridinyl)ethyl]-1H-benzimidazole-5-carbothioamide | 471 |
| 101 | 1-(cyclopropylmethyl)-N-[2-(dimethylamino)ethyl]-2-(4-ethoxybenzyl)-N-ethyl-1H-benzimidazole-5-carbothioamide | 465 |
| 102 | N-allyl-N-{[1-(cyclopropylmethyl)-2-(4-ethoxybenzyl)-1H-benzimidazol-5-yl]methyl}cyclopentanamine | 444 |
| 103 | 1-(cyclopropylmethyl)-2-(4-ethoxybenzyl)-N-(2-methoxyethyl)-1H-benzimidazole-5-sulfonamide | 444 |
| 104 | 5-[(4-acetyl-1-piperazinyl)sulfonyl]-1-(cyclopropylmethyl)-2-(4-ethoxybenzyl)-1H-benzimidazole | 497 |
| 105 | 1-(cyclopropylmethyl)-2-(4-ethoxybenzyl)-N-[2-(1-pyrrolidinyl)ethyl]-1H-benzimidazole-5-sulfonamide | 483 |
| 106 | 1-(cyclopropylmethyl)-N-(1,3-dioxolan-2-ylmethyl)-2-(4-ethoxybenzyl)-N-methyl-1H-benzimidazole-5-sulfonamide | 486 |
| 107 | 2-[[4-(cyclopropyloxy)phenyl]methyl]-N,N-diethyl-1-(3-methylbutyl)-1H-benzimidazole-5-carboxamide | |
| 108 | 2-[[4-(cyclobutyloxy)phenyl]methyl]-N,N-diethyl-1-(3-methylbutyl)-1H-benzimidazole-5-carboxamide | |
| 109 | 2-[[4-(cyclopentyloxy)phenyl]methyl]-N,N-diethyl-1-(3-methylbutyl)-1H-benzimidazole-5-carboxamide | |

Example 110

N-[1-(cyclopropylmethyl)-2-[(4-ethoxyphenyl)methyl]-1H-benzimidazol-5-yl]-N-methyl-1-piperidinecarboxaamide Into a solution of 1-(cyclopropylmethyl)-2-[1-(4-ethoxyphenyl)methyl]-N-methyl-1H-benzimidazol-5-amine (67.2 mg, 0.2 mmol, which was prepared according to a procedure described in Example 51AA), DIPEA (51.7 mg, 0.4 mmol) and DMAP (5 mg) in MeCN (8 mL) was added piperidine carbonyl chloride (44.3 mg, 0.3 mmol) at room temperature. The reaction mixture was heated for 24 h at reflux, quenched with H$_2$O (50 mL), and extracted with EtOAc (4×20 mL). The combined organic phases were washed with NaCl aqueous solution and dried over Na$_2$SO$_4$. Upon filtration and evaporation of the solvent, the residue was purified by MPLC using EtOAc on silica gel to give 75.2 mg (84%) of a colorless syrup, which was converted to a TFA salt as a white solid. $^1$H NMR (CD$_3$OD): δ0.51 (m, 2H), 0.66 (m, 2H), 1.28 (m, 1H), 1.41 (m, 7H), 1.55 (m, 2H), 3.28 (s, 3H), 3.34 (m, 4H), 4.07 (q, J=7.1 Hz, 2H), 4.39 (d, J=7.2 Hz, 2H), 4.57 (s, 2H), 7.01 (m, 2H), 7.30 (m, 2H), 7.39 (dd, J=9.0, 2.1 Hz, 1H), 7.44 (d, J=2.0 Hz, 1H), 7.90 (d, J=9.0 Hz, 1H). MS (ESI) (M+H)$^+$447.36. Anal. Calcd for C$_{27}$H$_{34}$N$_4$O$_2$+ 0.90TFA+0.60H$_2$O: C, 61.77; H, 6.50; N, 10.00. Found: C, 61:90; H, 6.65; N, 9.79.

Example 111

N-[1-(cyclopropylmethyl)-2-[(4-ethoxyphenyl)methyl]-1H-benzimidazol-5-yl]-N-methyl-1-pyrrolidinecarboxamide Into a solution of 1-(cyclopropylmethyl)-2-[1-(4-ethoxyphenyl)methyl]-N-methyl-1H-benzimidazol-5-amine (67.2 mg, 0.2 mmol, which was prepared according to a procedure described in Example 51AA), DIPEA (51.7 mg, 0.4 mmol)

and DMAP (5 mg) in MeCN (8 mL) was added pyrrolidine carbonyl chloride (40.1 mg, 0.3 mmol) at room temperature. The reaction mixture was heated for 24 h at reflux, quenched with H$_2$O (50 mL), and extracted with EtOAc (4×20 mL). The combined organic phases were washed with NaCl aqueous solution and dried over Na$_2$SO$_4$. Upon filtration and evaporation of the solvent, the residue was purified by MPLC using EtOAc on silica gel to give 79.4 mg (92%) of a colorless syrup, which was converted to a TFA salt, white solid. $^1$H NMR (CD$_3$OD): δ 0.50 (m, 2H), 0.65 (m, 2H), 1.29 (m, 1H), 1.41 (t, J=7.2 Hz, 3H), 1.75 (m, 4H), 3.28 (s, 3H), 3.34 (m, 4H), 4.07 (q, J=7.0 Hz, 2H), 4.39 (d, J=7.2 Hz, 2H), 4.58 (s, 2H), 7.01 (m, 2H), 7.31 (m, 2H), 7.43 (dd, J=9.0, 2.1 Hz, 1H), 7.48 (m, 1H), 7.91 (d, J=8.8 Hz, 1H). MS (ESI) (M+H)$^+$=433.34. Anal. Calcd for C$_{26}$H$_{32}$N$_4$O$_2$+0.90 TFA+0.20H$_2$O: C, 61.97; H, 6.23; N, 10.40. Found: C, 62.01; H, 6.20; N, 10.04.

What is claimed is:

1. A compound of formula I or a pharmaceutically acceptable salt thereof;

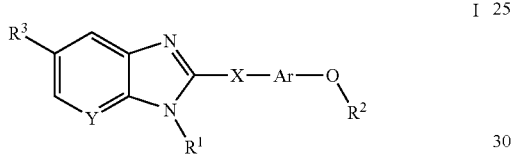

I wherein

R$^1$ is selected from the group consisting of —(C$_1$–C$_8$)alkyl, —(C$_2$–C$_8$)alkenyl, R$^4$$_2$N(C$_1$–C$_6$)alkyl-, R$^4$$_2$NC(=O)(C$_1$–C$_6$)alkyl-, R$^4$O(C$_1$–C$_6$)alkyl-, R$^4$OC(=O)(C$_1$–C$_6$)alkyl-, R$^4$C(=O)(C$_1$–C$_6$)alkyl-, R$^4$C(=O)NR$^4$(C$_1$–C$_6$)alkyl-, R$^4$$_2$NSO$_2$(C$_1$–C$_6$)alkyl-, R$^4$CSO$_2$NR$^4$(C$_1$–C$_6$)alkyl-, R$^4$$_2$NC(=O)NR$^4$(C$_1$–C$_6$)alkyl-, R$^4$$_2$NSO$_2$NR$^4$(C$_1$–C$_6$)alkyl-, aryl(C$_1$–C$_6$)alkyl, aroyl(C$_1$–C$_6$)alkyl, (C$_3$–C$_8$)heterocycloalkyl(C$_1$–C$_6$)alkyl, bicyclic heteroaryl (C$_1$–C$_6$)alkyl and bicyclic heteroaroyl(C$_1$–C$_6$)alkyl;

wherein said —(C$_2$–C$_8$)alkenyl, —(C$_1$–C$_8$)alkyl of R$^1$ are unsubstituted or substituted by one or more moieties independently selected from the group consisting of halogen, cyano, acetoxymethyl, and nitro;

Ar is an optionally substituted aryl moiety;

R$^2$ is —(C$_1$–C$_6$)alkyl, unsubstituted or substituted on 1–6 carbons by one or more fluorine substituents, or (C$_3$–C$_6$)cycloalkyl;

R$^3$ is selected from the group consisting of:

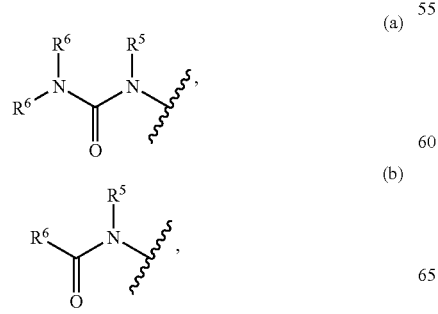

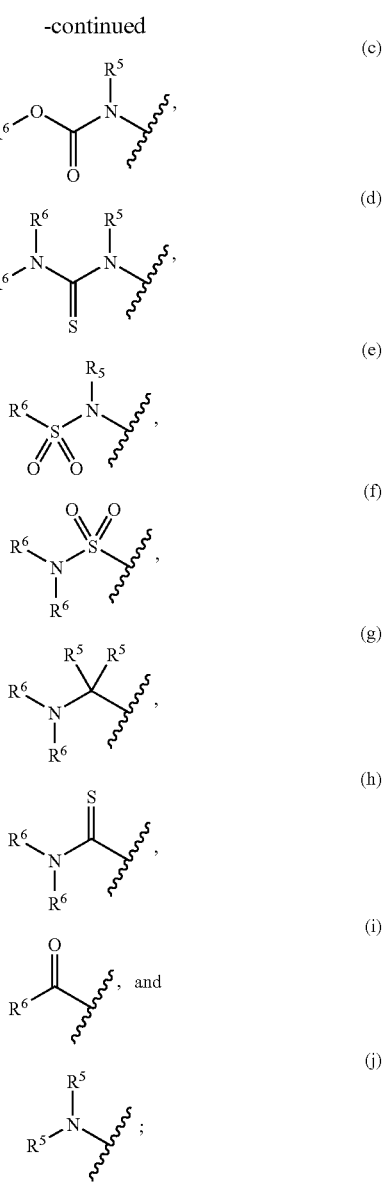

R$^4$ is a moiety independently selected from the group consisting of —H, —(C$_1$–C$_6$)alkyl, —(C$_2$–C$_6$) alkenyl and —(C$_2$–C$_6$)alkynyl;

R$^5$ moieties are independently selected from the group consisting of —H, —(C$_1$–C$_6$)alkyl, —(C$_2$–C$_6$)alkenyl and heterocyclyl;

R$^6$ moieties are independently selected from the group consisting of: —H, —(C$_1$–C$_6$)alkyl, —(C$_2$–C$_6$)alkenyl, —(C$_1$–C$_6$)alkanoyl, heterocyclyl, heterocyclyl (C$_1$–C$_3$)alkyl, aryl, aryl(C$_1$–C$_3$)alkyl, bicyclic heteroaryl, and bicyclic heteroaryl(C$_1$–C$_3$)alkyl; with a proviso that:

when R$^3$ is (b) or (i), R$^6$ is not —(C$_1$–C$_6$)alkyl;

when R$^3$ is (j), —R$^5$ are not both —H;

R$^5$ and R$^6$ may combine to form a 5–7 membered heterocycle;

X is selected from the group consisting of —C(R$^5$)$_2$—, —NR$^5$—, C(=O)—, —CH$_2$—CH$_2$—, —CH=CH—, —O—, —C(R)(R')—, and —S(O)$_n$— (where n=0, 1 or 2), where R and R'=(C$_1$–C$_6$)alkyl, OR", or H, and R"=H or (C$_1$–C$_6$)alkyl; and Y is CH; and wherein if $R^1$ represents $R^4{}_2N(C_1–C_6)$alkyl-, wherein both occurrences of $R^4$ represent —$(C_1–C_6)$alkyl, then $R^3$ is not acetyl, —$NH_2$, or acetamido.

2. A compound according to claim 1, wherein:

$R^1$ is selected from the group consisting of —$(C_1–C_8)$alkyl, —$(C_2–C_8)$alkenyl, aryl$(C_1–C_6)$alkyl, $R^4{}_2N(C_1–C_6)$alkyl-, $R^4O(C_1–C_6)$alkyl-, -heterocycloalkyl$(C_1–C_6)$alkyl (wherein the heterocyclyl is a 4- to 8-membered ring comprising one or more heteroatoms selected from nitrogen and oxygen), and heteroaryl$(C_1–C_6)$alkyl;

wherein aryl and heteroaryl $R^1$ moieties are unsubstituted or substituted by —$(C_1–C_6)$alkyl or halogen;

$R^2$ is selected from the group consisting of —$CH_3$, —$CH_2CH_3$, —$CH(CH_3)_2$, and $CF_3$;

$R^3$ is selected from the group consisting of:

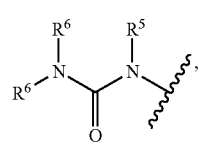
(a)

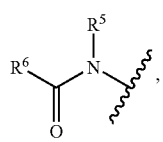
(b)

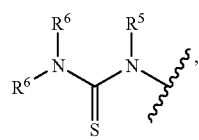
(d)

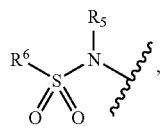
(e)

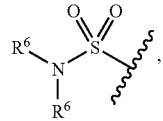
(f)

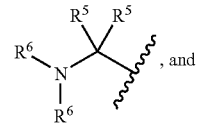
(g)
, and

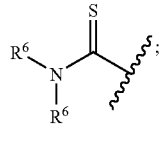
(h)
;

Ar is an aryl moiety; unsubstituted or substituted by one or more moieties independently selected from the group consisting of$(C_1–C_6)$alkyl, halogen, trifluoromethyl, cyano, nitro, hydroxy and —$OR^4$;

X is selected from the group consisting of —$CH_2$—, —$CH(CH_3)$—, —$C(CH_3)_2$—, —$CH(OH)$—, —$NH$—, —$N(CH_3)$—, —$CH_2CH_2$—, —$C(=O)$—, —$S$—, and —$O$—;

when Ar is a phenyl or six-membered heteroaromatic ring system, X is positioned on ring Ar in a 1,4 relationship with respect to the —$O$—$R^2$ group;

when Ar is a 5-membered heteroaromatic ring system, X is positioned on ring Ar in a 1,3 relationship with respect to the —$O$—$R^2$ group;

$R^4$ is independently selected from the group consisting of —H and —$(C_1–C_6)$alkyl;

$R^5$ is independently selected from the group consisting of —H, —$(C_1–C_6)$alkyl and —$(C_2–C_6)$alkenyl; and $R^6$ is independently selected from the group consisting of —H, —$(C_1–C_6)$alkyl, —$(C_2–C_6)$alkenyl, and heteroaryl;

wherein said heteroaryl is unsubstituted or substituted by —$(C_1–C_6)$alkyl.

3. A compound formula I,

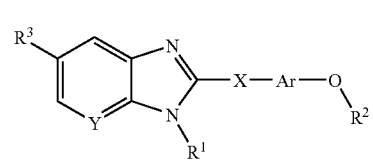
I wherein:

$R^1$ is selected from the group consisting of cyclopropylmethyl, ethyl, propyl, allyl, isopentyl, benzyl, methoxyethyl, dimethylaminoethyl, 4-pyridylmethyl, 2-pyridylmethyl, 1-pyrrolylmethyl, 1-morpholinoethyl, 5-(2-methylthiazolyl), cyclohexylmethyl, 2-pyrrolidylmethyl, N-methyl-2-pyrrolidylmethyl, 2-piperidylmethyl, N-methyl-2-piperidylmethyl, 3-thienylmethyl, 2-tetrahydrofuranylmethyl, (2-nitrothiophene-5-yl)methyl, (1-methyl-1H-imidazole-2-yl)methyl, (5-(acetoxymethyl)-2-furanyl)methyl, (2,3-dihydro -1H-isoindole-1-yl)methyl, and 5-(2-methylthiazolyl);

$R^2$ selected from the group consisting of —$CH_3$, —$CH_2CH_3$, —$CH(CH_3)_2$, and $CF_3$;

$R^3$ is selected from the group consisting of:

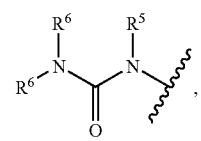
(a)

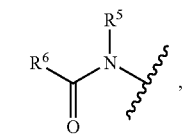
(b)

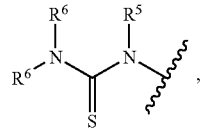
(d)

-continued

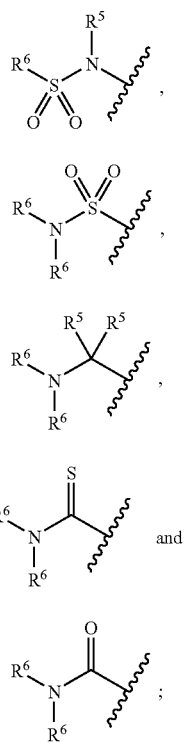

Y is CH;
R⁵ is selected from the group consisting of —H, —CH₃, —CH₂CH₃, —CH=CH₂ and —CH₂—CH=CH₂;

R⁶ is selected from the group consisting of —CH₃, —CH₂CH₃, —CH=CH₂, —CH₂—CH=CH₂, —CH₂—CH₂—CH=CH₂, —CH₂CH(CH₃)₂ and 5-methyl-3-isoxazole;

Ar is a phenyl or six-membered heteroaromatic ring system, either of which may be unsubstituted or substituted by one or more moieties independently selected from the group consisting of (C₁–C₆)alkyl, halogen, trifluoromethyl, cyano, nitro, hydroxy and —OR⁴;

X is selected from the group consisting of —CH₂—, —CH₂CH₂—, —S—, —O—, —CH(C₃)—, —C(CH₃)₂—, —CH(OH)—, —NH—, —N(CH₃)—, and —C(=O)—; and X is positioned on ring Ar in a 1,4 relationship with respect to the —O—R² group.

4. A compound according to claim 1, wherein:

R² is —CH₂CH₃;

Ar is unsubstituted phenyl or pyridyl;

X is selected from the group consisting of —CH₂—, —CH₂CH₂—, —S—, —CH(CH₃)—, —C(CH₃)2—, —CH(OH)—, —NH—, —N(CH₃)—, and —O—;

X is positioned on ring Ar in a 1,4 relationship with respect to the —O—R² group; and R⁴ is methyl.

5. A pharmaceutical composition comprising a compound according to claim 1 as an active ingredient in association with a pharmaceutically acceptable carrier.

6. A method for the therapy of pain in a warm-blooded animal, comprising administering to said animal in need of such therapy a therapeutically effective amount of a compound of the Formula I as described in claim 1.

* * * * *